US009314274B2

(12) United States Patent
Amstutz et al.

(10) Patent No.: US 9,314,274 B2
(45) Date of Patent: Apr. 19, 2016

(54) MINIMALLY INVASIVE SPINAL FIXATION SYSTEM INCLUDING VERTEBRAL ALIGNMENT FEATURES

(75) Inventors: Yann Amstutz, Oberdorf (CH); Didier Gonzalez, Oberdorf (CH); Michael Guetlin, Oberdorf (CH)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 13/479,657

(22) Filed: May 24, 2012

(65) Prior Publication Data

US 2012/0303062 A1   Nov. 29, 2012

Related U.S. Application Data

(60) Provisional application No. 61/490,689, filed on May 27, 2011.

(51) Int. Cl.
   *A61B 17/70*   (2006.01)
   *A61B 17/86*   (2006.01)

(52) U.S. Cl.
   CPC ......... *A61B 17/7038* (2013.01); *A61B 17/7041* (2013.01); *A61B 17/7083* (2013.01); *A61B 17/7091* (2013.01); *A61B 17/7082* (2013.01); *A61B 17/863* (2013.01)

(58) Field of Classification Search
   USPC ................................ 606/86 A, 246, 264–279
   See application file for complete search history.

(56) References Cited

U.S. PATENT DOCUMENTS

| | | | |
|---|---|---|---|
| 2,250,417 A | 7/1941 | Ettinger | |
| 2,373,478 A | 4/1945 | Kuhn | |
| 3,575,405 A | 4/1971 | Harding | |
| 4,335,715 A | 6/1982 | Kirkley | |
| 4,409,968 A | 10/1983 | Drummond | |
| 4,545,374 A | 10/1985 | Jacobson | |
| 4,733,657 A | 3/1988 | Kluger | |
| 4,827,918 A * | 5/1989 | Olerud | 606/258 |
| 4,957,495 A | 9/1990 | Kluger | |
| 5,015,247 A | 5/1991 | Michelson | |
| 5,047,029 A | 9/1991 | Aebi et al. | |
| 5,171,279 A | 12/1992 | Mathews | |
| 5,207,678 A | 5/1993 | Harms et al. | |
| 5,217,497 A | 6/1993 | Mehdian | |
| 5,219,349 A | 6/1993 | Krag et al. | |
| 5,242,443 A | 9/1993 | Kambin | |
| 5,312,404 A | 5/1994 | Asher et al. | |
| 5,344,422 A | 9/1994 | Frigg | |

(Continued)

FOREIGN PATENT DOCUMENTS

| | | |
|---|---|---|
| AU | 1367295 | 9/1995 |
| DE | 9215561 | 1/1993 |

(Continued)

OTHER PUBLICATIONS

Aperture Spinal Access System, DePuy AcroMed, 2003, 6 pages.

(Continued)

*Primary Examiner* — Jan Christopher Merene
*Assistant Examiner* — Steven Cotroneo
(74) *Attorney, Agent, or Firm* — Baker & Hostetler LLP

(57) ABSTRACT

A bone anchor coupler assembly is configured to couple a bone anchor to a spine stabilization member, and includes a coupler body and an angular adjustment member movably coupled to the coupler body.

33 Claims, 27 Drawing Sheets

(56) References Cited

U.S. PATENT DOCUMENTS

| | | | |
|---|---|---|---|
| 5,352,231 A | 10/1994 | Brumfield et al. | |
| 5,360,431 A | 11/1994 | Puno et al. | |
| 5,431,658 A | 7/1995 | Moskovich | |
| 5,433,467 A | 7/1995 | Easterwood | |
| 5,439,464 A | 8/1995 | Shapiro | |
| 5,443,467 A | 8/1995 | Biedermann et al. | |
| 5,474,555 A | 12/1995 | Puno et al. | |
| 5,501,684 A | 3/1996 | Schlapfer et al. | |
| 5,520,690 A | 5/1996 | Errico et al. | |
| 5,529,571 A | 6/1996 | Daniel | |
| 5,531,746 A | 7/1996 | Errico et al. | |
| 5,562,661 A | 10/1996 | Yashimi et al. | |
| 5,605,458 A | 2/1997 | Bailey et al. | |
| 5,607,426 A | 3/1997 | Ralph et al. | |
| 5,611,800 A | 3/1997 | Davis et al. | |
| 5,613,968 A | 3/1997 | Lin | |
| 5,624,441 A | 4/1997 | Sherman et al. | |
| 5,624,442 A | 4/1997 | Mellinger et al. | |
| 5,647,873 A | 7/1997 | Errico et al. | |
| 5,667,506 A | 9/1997 | Sutterlin | |
| 5,667,513 A | 9/1997 | Torrie et al. | |
| 5,669,911 A | 9/1997 | Errico et al. | |
| 5,676,664 A | 10/1997 | Allard et al. | |
| 5,690,630 A | 11/1997 | Errico et al. | |
| 5,720,751 A | 2/1998 | Jackson | |
| 5,725,588 A | 3/1998 | Errico et al. | |
| 5,782,830 A | 7/1998 | Farris | |
| 5,782,833 A | 7/1998 | Haider | |
| 5,797,911 A | 8/1998 | Sherman et al. | |
| 5,810,878 A | 9/1998 | Burel et al. | |
| 5,817,094 A | 10/1998 | Errico et al. | |
| 5,863,293 A | 1/1999 | Richelsoph | |
| 5,876,402 A | 3/1999 | Errico et al. | |
| 5,879,350 A | 3/1999 | Sherman et al. | |
| 5,882,350 A | 3/1999 | Ralph et al. | |
| 5,885,285 A | 3/1999 | Simonson | |
| 5,885,286 A | 3/1999 | Sherman et al. | |
| 5,888,204 A | 3/1999 | Ralph et al. | |
| 5,910,141 A | 6/1999 | Morrison et al. | |
| 5,938,663 A | 8/1999 | Petreto | |
| 5,951,559 A | 9/1999 | Burkhart | |
| 5,964,760 A | 10/1999 | Richelsoph | |
| 5,964,761 A | 10/1999 | Kambin | |
| 6,010,503 A | 1/2000 | Richelsoph et al. | |
| 6,030,388 A | 2/2000 | Yoshimi et al. | |
| 6,053,917 A | 4/2000 | Sherman et al. | |
| 6,055,456 A | 4/2000 | Gerber et al. | |
| 6,066,174 A | 5/2000 | Farris | |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen | |
| 6,090,111 A | 7/2000 | Nichols | |
| 6,090,113 A | 7/2000 | Le Couedic et al. | |
| 6,132,432 A | 10/2000 | Richelsoph | |
| 6,139,493 A | 10/2000 | Koros et al. | |
| 6,139,549 A | 10/2000 | Keller | |
| 6,183,472 B1 | 2/2001 | Lutz | |
| 6,187,005 B1 | 2/2001 | Brace et al. | |
| 6,200,322 B1 | 3/2001 | Branch et al. | |
| 6,214,006 B1 | 4/2001 | Metz-Stavenhagen | |
| 6,224,598 B1 | 5/2001 | Jackson | |
| 6,224,603 B1 | 5/2001 | Marino | |
| 6,235,028 B1 | 5/2001 | Brumfield et al. | |
| 6,251,112 B1 | 6/2001 | Jackson | |
| 6,261,287 B1 | 7/2001 | Metz-Stavenhagen | |
| 6,280,442 B1 | 8/2001 | Barker et al. | |
| 6,302,888 B1 | 10/2001 | Mellinger et al. | |
| 6,355,040 B1 | 3/2002 | Richelsoph et al. | |
| 6,360,750 B1 | 3/2002 | Gerber et al. | |
| 6,361,535 B2 | 3/2002 | Jackson | |
| RE37,665 E | 4/2002 | Ralph et al. | |
| 6,368,321 B1 | 4/2002 | Jackson | |
| 6,415,693 B1 | 7/2002 | Simon et al. | |
| 6,440,113 B1 | 8/2002 | Brisebois et al. | |
| 6,440,133 B1 | 8/2002 | Beale et al. | |
| 6,475,218 B2 | 11/2002 | Gournay et al. | |
| 6,485,491 B1 | 11/2002 | Farris et al. | |
| 6,488,681 B2 | 12/2002 | Martin et al. | |
| 6,512,958 B1 | 1/2003 | Swoyer et al. | |
| 6,520,907 B1 | 2/2003 | Foley et al. | |
| 6,530,926 B1 | 3/2003 | Davison | |
| 6,530,929 B1 | 3/2003 | Justis et al. | |
| 6,537,276 B2 | 3/2003 | Metz-Stavenhagen | |
| 6,554,834 B1 | 4/2003 | Crozet et al. | |
| 6,558,387 B2 | 5/2003 | Errico et al. | |
| 6,565,565 B1 | 5/2003 | Yuan et al. | |
| 6,579,291 B1 | 6/2003 | Keith et al. | |
| 6,610,065 B1 | 8/2003 | Branch et al. | |
| 6,626,905 B1 | 9/2003 | Schmiel et al. | |
| 6,626,906 B1 | 9/2003 | Young | |
| 6,648,888 B1 | 11/2003 | Shluzas | |
| 6,660,004 B2 | 12/2003 | Barker et al. | |
| 6,673,074 B2 | 1/2004 | Shluzas | |
| 6,719,758 B2 | 4/2004 | Beger et al. | |
| 6,726,692 B2 | 4/2004 | Bette | |
| 6,736,816 B2 | 5/2004 | Ritland | |
| 6,743,231 B1 | 6/2004 | Gray et al. | |
| 6,780,186 B2 | 8/2004 | Errico et al. | |
| 6,783,527 B2 | 8/2004 | Drewry et al. | |
| 6,790,208 B2 | 9/2004 | Oribe et al. | |
| 6,800,084 B2 | 10/2004 | Davison et al. | |
| 6,821,277 B2 | 11/2004 | Teitelbaum | |
| 6,827,722 B1 | 12/2004 | Schoenefeld | |
| 6,843,791 B2 | 1/2005 | Serhan | |
| 6,849,064 B2 | 2/2005 | Hamada | |
| 6,929,606 B2 | 8/2005 | Ritland | |
| 7,008,422 B2 | 3/2006 | Foley et al. | |
| 7,011,658 B2 | 3/2006 | Young | |
| 7,011,660 B2 | 3/2006 | Sherman et al. | |
| 7,018,379 B2 | 3/2006 | Drewry et al. | |
| RE39,089 E | 5/2006 | Ralph et al. | |
| 7,083,621 B2 | 8/2006 | Shaolian et al. | |
| 7,104,992 B2 | 9/2006 | Bailey | |
| 7,128,743 B2 | 10/2006 | Metz-Stavenhagen | |
| 7,160,300 B2 | 1/2007 | Jackson | |
| 7,166,109 B2 | 1/2007 | Biedermann et al. | |
| 7,179,225 B2 | 2/2007 | Shluzas et al. | |
| 7,179,261 B2 | 2/2007 | Sicvol et al. | |
| 7,186,255 B2 | 3/2007 | Baynham et al. | |
| 7,188,626 B2 | 3/2007 | Foley et al. | |
| 7,250,052 B2 * | 7/2007 | Landry et al. | 606/86 A |
| 7,261,714 B2 | 8/2007 | Richelsoph | |
| 7,303,562 B2 | 12/2007 | Cavagna et al. | |
| 7,306,603 B2 | 12/2007 | Boehm, Jr. et al. | |
| 7,455,685 B2 | 11/2008 | Justis | |
| 7,465,306 B2 | 12/2008 | Pond et al. | |
| 7,470,279 B2 | 12/2008 | Jackson | |
| 7,476,240 B2 | 1/2009 | Raymond et al. | |
| 7,491,208 B2 | 2/2009 | Pond, Jr. et al. | |
| 7,491,218 B2 | 2/2009 | Landry et al. | |
| 7,520,879 B2 | 4/2009 | Justis et al. | |
| 7,527,638 B2 | 5/2009 | Anderson et al. | |
| 7,547,318 B2 | 6/2009 | Birkmeyer et al. | |
| 7,563,264 B2 | 7/2009 | Landry et al. | |
| 7,572,276 B2 | 8/2009 | Lim et al. | |
| 7,608,081 B2 | 10/2009 | Abdelgany | |
| 7,608,096 B2 | 10/2009 | Foley et al. | |
| 7,618,424 B2 | 11/2009 | Wilcox et al. | |
| 7,651,502 B2 | 1/2010 | Jackson | |
| 7,678,112 B2 * | 3/2010 | Rezach | 606/60 |
| 7,686,809 B2 | 3/2010 | Triplett et al. | |
| 7,691,132 B2 | 4/2010 | Landry et al. | |
| 7,708,763 B2 | 5/2010 | Selover et al. | |
| 7,717,944 B2 | 5/2010 | Foley et al. | |
| 7,744,635 B2 * | 6/2010 | Sweeney et al. | 606/264 |
| 7,758,584 B2 | 7/2010 | Bankoski et al. | |
| 7,763,055 B2 | 7/2010 | Foley | |
| 7,776,051 B2 | 8/2010 | Colleran et al. | |
| 7,811,288 B2 | 10/2010 | Jones et al. | |
| 7,824,411 B2 | 11/2010 | Varieur et al. | |
| 7,824,413 B2 | 11/2010 | Varieur et al. | |
| 7,842,044 B2 | 11/2010 | Runco et al. | |
| 7,842,073 B2 | 11/2010 | Richelsoph et al. | |
| 7,850,715 B2 | 12/2010 | Banouskou et al. | |

(56) References Cited

U.S. PATENT DOCUMENTS

| | | |
|---|---|---|
| 7,850,716 B2 | 12/2010 | Taylor |
| 7,854,751 B2 | 12/2010 | Sicvol et al. |
| 7,862,587 B2 | 1/2011 | Jackson |
| 7,862,595 B2 | 1/2011 | Foley et al. |
| 7,867,259 B2 | 1/2011 | Foley et al. |
| 7,887,539 B2 | 2/2011 | Dunbar, Jr. et al. |
| 7,896,902 B2 | 3/2011 | Jeon et al. |
| 7,914,558 B2 | 3/2011 | Landry et al. |
| 7,931,677 B2 | 4/2011 | Abdelgany |
| 7,955,355 B2 | 6/2011 | Chin et al. |
| 7,955,363 B2 | 6/2011 | Richelsoph |
| 7,976,569 B2 | 7/2011 | Justis |
| 7,985,242 B2 | 7/2011 | Forton et al. |
| 8,002,798 B2 | 8/2011 | Chin et al. |
| 8,021,398 B2 | 9/2011 | Sweeney et al. |
| 8,029,546 B2 | 10/2011 | Capote et al. |
| 8,034,084 B2 | 10/2011 | Landry et al. |
| 8,043,343 B2 | 10/2011 | Miller et al. |
| 8,066,739 B2 | 11/2011 | Jackson |
| 8,075,592 B2 | 12/2011 | Landry et al. |
| 8,088,152 B2 | 1/2012 | Schumacher |
| 8,092,494 B2 | 1/2012 | Butler et al. |
| 8,096,996 B2 | 1/2012 | Gutierrez et al. |
| 8,097,027 B2 | 1/2012 | Lim et al. |
| 8,100,828 B2 | 1/2012 | Frey et al. |
| 8,100,913 B2 | 1/2012 | Abdelgany |
| 8,100,915 B2 | 1/2012 | Jackson |
| 8,100,951 B2 | 1/2012 | Justis et al. |
| 8,105,361 B2 | 1/2012 | Anderson et al. |
| 8,118,737 B2 | 2/2012 | Perez-Cruet et al. |
| 8,123,751 B2 | 2/2012 | Shluzas |
| 8,128,665 B2* | 3/2012 | Banouskou et al. .......... 606/250 |
| 8,152,810 B2 | 4/2012 | Jackson |
| 8,172,855 B2 | 5/2012 | Abdou |
| 8,177,817 B2 | 5/2012 | Fallin |
| 8,262,662 B2 | 9/2012 | Beardsley et al. |
| 8,262,702 B2 | 9/2012 | Giger et al. |
| 8,287,546 B2 | 10/2012 | King et al. |
| 8,292,892 B2 | 10/2012 | Jackson |
| 8,460,308 B2 | 6/2013 | Marino et al. |
| 8,469,960 B2 | 6/2013 | Hutton et al. |
| 8,480,713 B2* | 7/2013 | Rezach ........... 606/250 |
| 8,535,318 B2 | 9/2013 | Peterson et al. |
| 8,585,741 B2 | 11/2013 | Gabelberger et al. |
| 8,679,129 B2 | 3/2014 | Sorrenti et al. |
| 2002/0020255 A1 | 2/2002 | Simon et al. |
| 2002/0193802 A1 | 12/2002 | Zdeblick et al. |
| 2003/0040752 A1 | 2/2003 | Kitchens |
| 2003/0073998 A1 | 4/2003 | Pagliuca et al. |
| 2003/0115180 A1 | 6/2003 | Eves et al. |
| 2003/0135220 A1 | 7/2003 | Cauthen |
| 2003/0149341 A1 | 8/2003 | Clifton |
| 2003/0191371 A1 | 10/2003 | Smith et al. |
| 2003/0199872 A1 | 10/2003 | Markworth et al. |
| 2003/0208203 A1 | 11/2003 | Lim et al. |
| 2003/0216768 A1 | 11/2003 | Gitis et al. |
| 2003/0225408 A1 | 12/2003 | Nichols et al. |
| 2003/0236447 A1 | 12/2003 | Ritland |
| 2004/0002629 A1 | 1/2004 | Branch et al. |
| 2004/0024398 A1 | 2/2004 | Hovda et al. |
| 2004/0034351 A1 | 2/2004 | Sherman et al. |
| 2004/0039384 A1 | 2/2004 | Boehm et al. |
| 2004/0092930 A1* | 5/2004 | Petit et al. ........... 606/61 |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147937 A1* | 7/2004 | Dunbar et al. ............ 606/99 |
| 2004/0153068 A1 | 8/2004 | Janowski et al. |
| 2004/0172022 A1 | 9/2004 | Landry et al. |
| 2004/0176763 A1 | 9/2004 | Foley et al. |
| 2004/0215190 A1 | 10/2004 | Nguyen et al. |
| 2004/0254574 A1 | 12/2004 | Morrison et al. |
| 2004/0267275 A1 | 12/2004 | Cournoyer et al. |
| 2005/0004593 A1 | 1/2005 | Simonson |
| 2005/0021031 A1 | 1/2005 | Foley et al. |
| 2005/0021040 A1 | 1/2005 | Bertagnoli |
| 2005/0038432 A1 | 2/2005 | Shaolian et al. |
| 2005/0065517 A1 | 3/2005 | Chin |
| 2005/0065518 A1 | 3/2005 | Michelson et al. |
| 2005/0070765 A1 | 3/2005 | Abdelgany et al. |
| 2005/0070901 A1 | 3/2005 | David |
| 2005/0075644 A1 | 4/2005 | DiPoto et al. |
| 2005/0080418 A1 | 4/2005 | Simonson et al. |
| 2005/0085813 A1 | 4/2005 | Spitler et al. |
| 2005/0090824 A1 | 4/2005 | Shluzas et al. |
| 2005/0096654 A1 | 5/2005 | Lin |
| 2005/0131408 A1 | 6/2005 | Sicvol et al. |
| 2005/0131419 A1 | 6/2005 | McCord et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0159650 A1 | 7/2005 | Raymond et al. |
| 2005/0171540 A1 | 8/2005 | Lim et al. |
| 2005/0192570 A1 | 9/2005 | Jackson |
| 2005/0192579 A1 | 9/2005 | Jackson |
| 2005/0192589 A1 | 9/2005 | Raymond et al. |
| 2005/0203532 A1 | 9/2005 | Ferguson et al. |
| 2005/0215999 A1 | 9/2005 | Birkmeyer et al. |
| 2005/0228380 A1 | 10/2005 | Moore et al. |
| 2005/0228382 A1 | 10/2005 | Richelsoph et al. |
| 2005/0228400 A1 | 10/2005 | Chao et al. |
| 2005/0234449 A1 | 10/2005 | Aferzon |
| 2005/0240181 A1 | 10/2005 | Boomer et al. |
| 2005/0277934 A1 | 12/2005 | Vardiman |
| 2006/0009780 A1 | 1/2006 | Foley et al. |
| 2006/0025768 A1 | 2/2006 | Iott et al. |
| 2006/0036244 A1 | 2/2006 | Spitler et al. |
| 2006/0036252 A1 | 2/2006 | Baynham et al. |
| 2006/0036255 A1 | 2/2006 | Pond et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0074445 A1 | 4/2006 | Gerber et al. |
| 2006/0079894 A1 | 4/2006 | Colleran et al. |
| 2006/0079909 A1 | 4/2006 | Runco et al. |
| 2006/0084993 A1 | 4/2006 | Landry et al. |
| 2006/0095035 A1 | 5/2006 | Jones et al. |
| 2006/0106380 A1 | 5/2006 | Colleran et al. |
| 2006/0106394 A1 | 5/2006 | Colleran |
| 2006/0111712 A1 | 5/2006 | Jackson |
| 2006/0111714 A1 | 5/2006 | Foley |
| 2006/0111715 A1 | 5/2006 | Jackson |
| 2006/0122597 A1 | 6/2006 | Jones et al. |
| 2006/0142716 A1 | 6/2006 | Long et al. |
| 2006/0142761 A1 | 6/2006 | Landry et al. |
| 2006/0167454 A1 | 7/2006 | Ludwig et al. |
| 2006/0167455 A1* | 7/2006 | Clement et al. ............ 606/61 |
| 2006/0173454 A1 | 8/2006 | Spitler et al. |
| 2006/0184172 A1 | 8/2006 | Michelson et al. |
| 2006/0184178 A1 | 8/2006 | Jackson |
| 2006/0200135 A1 | 9/2006 | Sherman et al. |
| 2006/0206114 A1 | 9/2006 | Ensign et al. |
| 2006/0229614 A1 | 10/2006 | Foley et al. |
| 2006/0241596 A1 | 10/2006 | Rezach |
| 2006/0241649 A1 | 10/2006 | Vasta et al. |
| 2006/0247624 A1* | 11/2006 | Banouskou et al. ............ 606/61 |
| 2006/0247658 A1 | 11/2006 | Pond et al. |
| 2006/0264942 A1 | 11/2006 | Lim et al. |
| 2006/0264962 A1 | 11/2006 | Chin et al. |
| 2006/0276803 A1 | 12/2006 | Salerni et al. |
| 2006/0293678 A1 | 12/2006 | Davison et al. |
| 2006/0293680 A1 | 12/2006 | Jackson |
| 2006/0293693 A1 | 12/2006 | Farr et al. |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016200 A1 | 1/2007 | Jackson |
| 2007/0025132 A1 | 2/2007 | Liaw |
| 2007/0032162 A1 | 2/2007 | Jackson |
| 2007/0073294 A1 | 3/2007 | Chin et al. |
| 2007/0106123 A1 | 5/2007 | Gorek et al. |

(56) References Cited

U.S. PATENT DOCUMENTS

| | | | |
|---|---|---|---|
| 2007/0129731 A1 | 6/2007 | Sicvol et al. | |
| 2007/0135817 A1 | 6/2007 | Ensign | |
| 2007/0161987 A1* | 7/2007 | Capote et al. | 606/61 |
| 2007/0161998 A1* | 7/2007 | Whipple | 606/61 |
| 2007/0162046 A1 | 7/2007 | Vandewalle | |
| 2007/0167946 A1 | 7/2007 | Triplett et al. | |
| 2007/0167954 A1 | 7/2007 | Sicvol et al. | |
| 2007/0173745 A1 | 7/2007 | Diederich et al. | |
| 2007/0185491 A1 | 8/2007 | Foley et al. | |
| 2007/0198015 A1 | 8/2007 | Foley et al. | |
| 2007/0233067 A1* | 10/2007 | Taylor | 606/61 |
| 2007/0233079 A1 | 10/2007 | Fallin et al. | |
| 2007/0238335 A1 | 10/2007 | Veldman et al. | |
| 2007/0260125 A1 | 11/2007 | Strauss et al. | |
| 2007/0270842 A1 | 11/2007 | Bankoski et al. | |
| 2008/0009864 A1 | 1/2008 | Forton et al. | |
| 2008/0039838 A1 | 2/2008 | Landry et al. | |
| 2008/0045957 A1 | 2/2008 | Landry et al. | |
| 2008/0051794 A1 | 2/2008 | Dec et al. | |
| 2008/0051897 A1 | 2/2008 | Lopez et al. | |
| 2008/0077139 A1 | 3/2008 | Landry et al. | |
| 2008/0077155 A1 | 3/2008 | Diederich et al. | |
| 2008/0081951 A1 | 4/2008 | Frasier et al. | |
| 2008/0086132 A1 | 4/2008 | Biedermann et al. | |
| 2008/0091213 A1 | 4/2008 | Jackson | |
| 2008/0140132 A1 | 6/2008 | Perez-Cruet | |
| 2008/0154278 A1 | 6/2008 | Abdelgany | |
| 2008/0167688 A1 | 7/2008 | Fauth et al. | |
| 2008/0177270 A1 | 7/2008 | Sorrenti et al. | |
| 2008/0255567 A1 | 10/2008 | Accordino | |
| 2008/0262318 A1 | 10/2008 | Gorek et al. | |
| 2008/0288005 A1 | 11/2008 | Jackson | |
| 2008/0294198 A1 | 11/2008 | Jackson | |
| 2008/0294202 A1 | 11/2008 | Peterson et al. | |
| 2008/0300638 A1 | 12/2008 | Beardsley et al. | |
| 2009/0005814 A1 | 1/2009 | Miller et al. | |
| 2009/0088604 A1 | 4/2009 | Lowry et al. | |
| 2009/0093684 A1 | 4/2009 | Schorer | |
| 2009/0138056 A1 | 5/2009 | Anderson et al. | |
| 2009/0163924 A1 | 6/2009 | Justis | |
| 2009/0171391 A1 | 7/2009 | Hutton et al. | |
| 2009/0228052 A1 | 9/2009 | Beardsley et al. | |
| 2009/0228055 A1* | 9/2009 | Jackson | 606/86 A |
| 2009/0228056 A1 | 9/2009 | Jackson | |
| 2009/0270916 A1 | 10/2009 | Ramsay et al. | |
| 2009/0287253 A1 | 11/2009 | Felix et al. | |
| 2009/0318972 A1 | 12/2009 | Jackson | |
| 2010/0024487 A1 | 2/2010 | Khoo et al. | |
| 2010/0030283 A1 | 2/2010 | King et al. | |
| 2010/0036443 A1 | 2/2010 | Hutton et al. | |
| 2010/0131016 A1 | 5/2010 | Gerber et al. | |
| 2010/0174325 A1 | 7/2010 | Won et al. | |
| 2010/0198272 A1 | 8/2010 | Keyer et al. | |
| 2010/0268279 A1 | 10/2010 | Gabelberger et al. | |
| 2010/0268284 A1 | 10/2010 | Bankoski et al. | |
| 2010/0274252 A1 | 10/2010 | Bottomley et al. | |
| 2010/0331849 A1 | 12/2010 | Riesinger et al. | |
| 2011/0054537 A1 | 3/2011 | Miller et al. | |
| 2011/0130634 A1 | 6/2011 | Solitario, Jr. et al. | |
| 2011/0166606 A1 | 7/2011 | Stihl et al. | |
| 2011/0184469 A1 | 7/2011 | Ballard et al. | |
| 2011/0263945 A1 | 10/2011 | Peterson et al. | |
| 2012/0089191 A1 | 4/2012 | Altarac et al. | |
| 2012/0290012 A1 | 11/2012 | Rutledge | |
| 2012/0303062 A1 | 11/2012 | Amstutz et al. | |
| 2013/0253598 A1 | 9/2013 | Jackson | |
| 2013/0274804 A1 | 10/2013 | Hutton et al. | |
| 2014/0012321 A1 | 1/2014 | Hutton et al. | |
| 2014/0074171 A1 | 3/2014 | Hutton et al. | |
| 2014/0114360 A1 | 4/2014 | Gephart et al. | |

FOREIGN PATENT DOCUMENTS

| | | |
|---|---|---|
| DE | 4238339 | 5/1994 |
| DE | 19726754 | 2/1999 |
| DE | 10027988 | 1/2002 |
| EP | 0528177 | 2/1993 |
| EP | 0558883 | 9/1993 |
| EP | 0483242 | 5/1995 |
| EP | 0836835 | 4/1998 |
| EP | 0885598 | 12/1998 |
| EP | 0947174 | 10/1999 |
| EP | 0746255 | 9/2002 |
| EP | 0934027 | 12/2003 |
| EP | 1087711 | 5/2004 |
| EP | 0934028 | 6/2004 |
| EP | 1119304 | 7/2005 |
| EP | 1214006 | 10/2005 |
| EP | 1316295 | 10/2005 |
| EP | 1317215 | 12/2005 |
| EP | 1459215 | 12/2005 |
| EP | 1642542 | 4/2006 |
| EP | 0986338 | 7/2006 |
| EP | 1248573 | 8/2006 |
| FR | 2757761 | 7/1998 |
| JP | 11076247 | 3/1999 |
| JP | 2000-032359 | 1/2000 |
| JP | 2004-512134 | 4/2004 |
| JP | 2004-516040 | 6/2004 |
| JP | 2012-501809 | 2/2012 |
| WO | WO 02/36026 | 5/2002 |
| WO | WO 2004/041100 | 5/2004 |
| WO | WO 2005/058141 | 6/2005 |
| WO | WO 2005/060534 | 7/2005 |
| WO | WO 2006/042188 | 4/2006 |
| WO | WO 2006/060430 | 6/2006 |
| WO | WO 2006/116305 A1 | 11/2006 |
| WO | WO 2006/116662 | 11/2006 |
| WO | WO 2007/022790 | 3/2007 |
| WO | WO 2007/025132 | 3/2007 |
| WO | WO 2007/038350 | 4/2007 |
| WO | WO 2007/067443 | 6/2007 |
| WO | WO 2007/070757 | 6/2007 |
| WO | WO 2007/117366 | 10/2007 |
| WO | WO 2008/014477 | 1/2008 |
| WO | WO 2008/022268 | 2/2008 |
| WO | WO 2009/011929 | 1/2009 |
| WO | WO 2009/055026 | 4/2009 |
| WO | WO 2010/030916 | 3/2010 |

OTHER PUBLICATIONS

"Polyaxial Reduction Screw; Surgical Technique", DePuy AcroMed, 1998, 13 pages.

Atavi Atraumatic Spine Fusion System, "Endoscopic Posterolateral Fusion", 2001, 10 pages.

Branch et al., "TANGENT posterior impacted instrument set technique", Medtronic Sofamor Danek, 2000, 9 pages.

Constellation CP System, "A minimally invasive system for use with Cannulated Pangea", Technique Guide, Synthes Spinem, 2008, 42 pages.

Foley, Medtronic Sofamor Danek, "CD horizon SEXTANT rod insertion system surgical technique", Department of Neurosurgery, Un. Of Tenn., 2002, 30 pages.

Hilton, Jr. et al., Medtronic Sofamor Danek , "Metrx microdiscectomy surgical technique", Neurological Surgery, 2000, 19 pages.

Kambin, "The role of minimally invasive surgery in spinal disorder", Advances in Operative Orhtopaedics, 1995, 147-171.

Muller et al., "A keyhole approach for endoscopically assisted pedicle screw fixation in lumbar spine instability (techniques and applications)", Department of Neurosurgery, 1999, 18 pages.

Muller et al., "Techniques and applications; A keyhole approach for endoscopically assisted pedicle screw fixation in lumbar spine intability", Neurosurgery, Jul. 2000, 47(1).

Thongtrangan et al., "Minimally invasive spinal surgery: a historical perspective", Neurosurg. Focus, Jan. 2004, 16. 1-10.

(56) References Cited

OTHER PUBLICATIONS

Turner, "A new, radially expanding access system for laparoscopic procedures versus conventional cannulas", The Journal of the American Association of Gynecologic Laparoscopists, Aug. 1996, 3(4), 609-615.

Synthes Spine, "USS Fracture System: Technique Guide", 2001, 20 pages.

Viper 2 System Guide, DePuy Spine, 2011, 60 pages.

Wiltse et al., "New Uses and Refinements of the Paraspinal Approach to the Lumbar Spine", Nov. 16, 1987, 12 pages.

MATRIX Spine System—Deformity Technique Guide, "A Posterior Pedicle Screw, Hook, and Rod Fixation System," Synthes, © 2010, 75 pages.

Xia Spinal System, Stryker Howmedica Oseteonics, Stryker Spine, 1999, 8 pages.

International Patent Application No. PCT/US2007/066469: International Search Report dated Aug. 1, 2008, 6 pages.

* cited by examiner

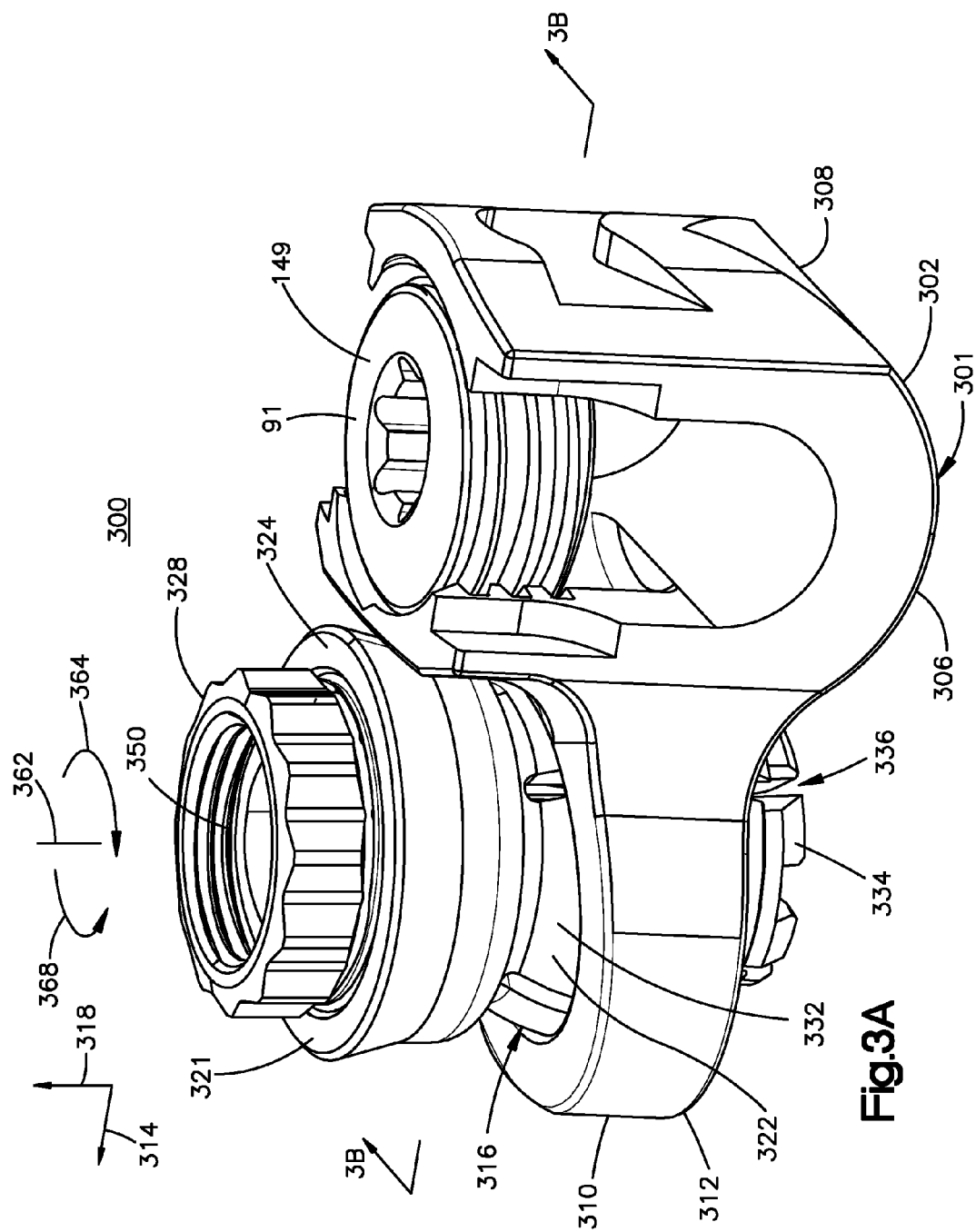

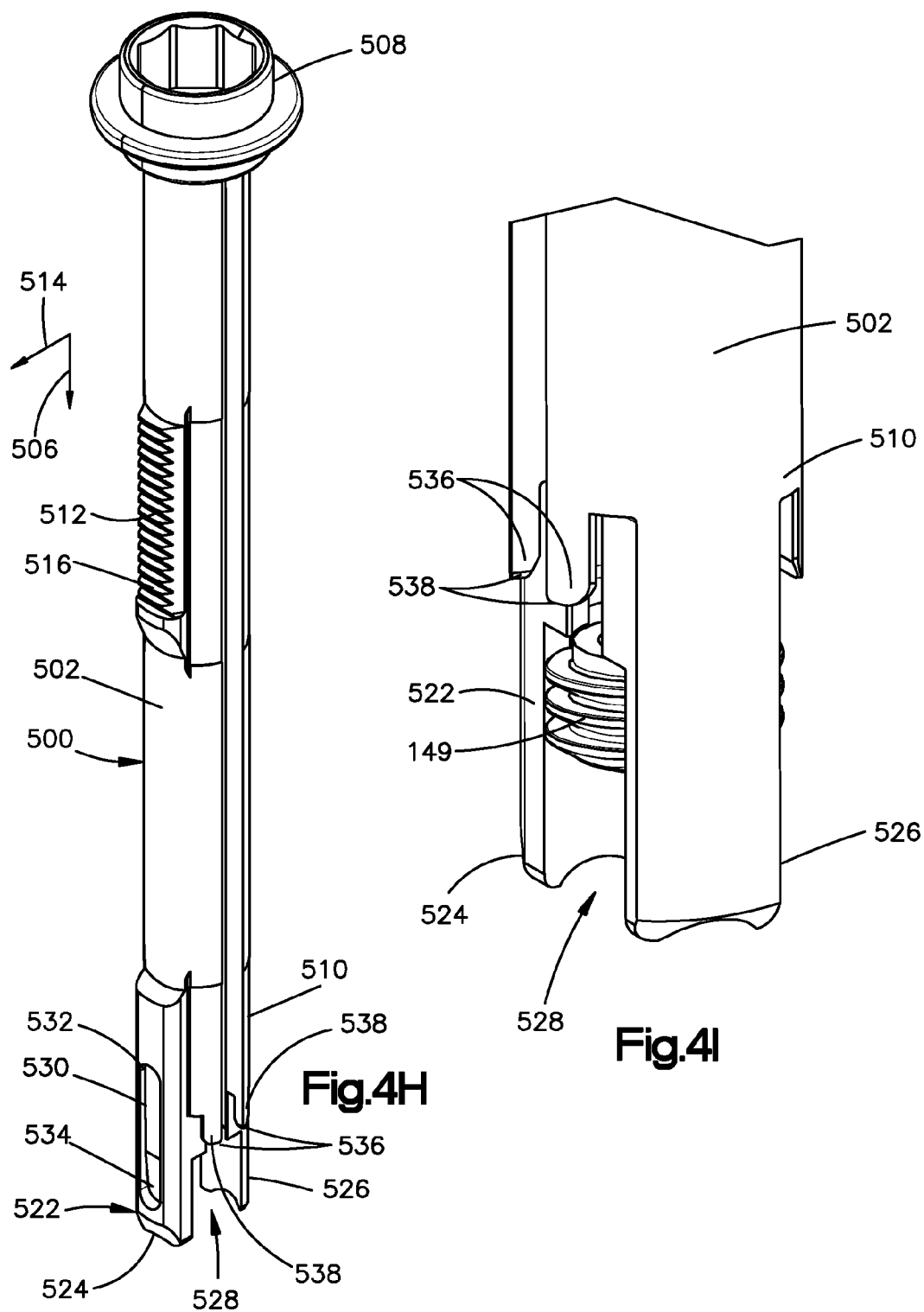

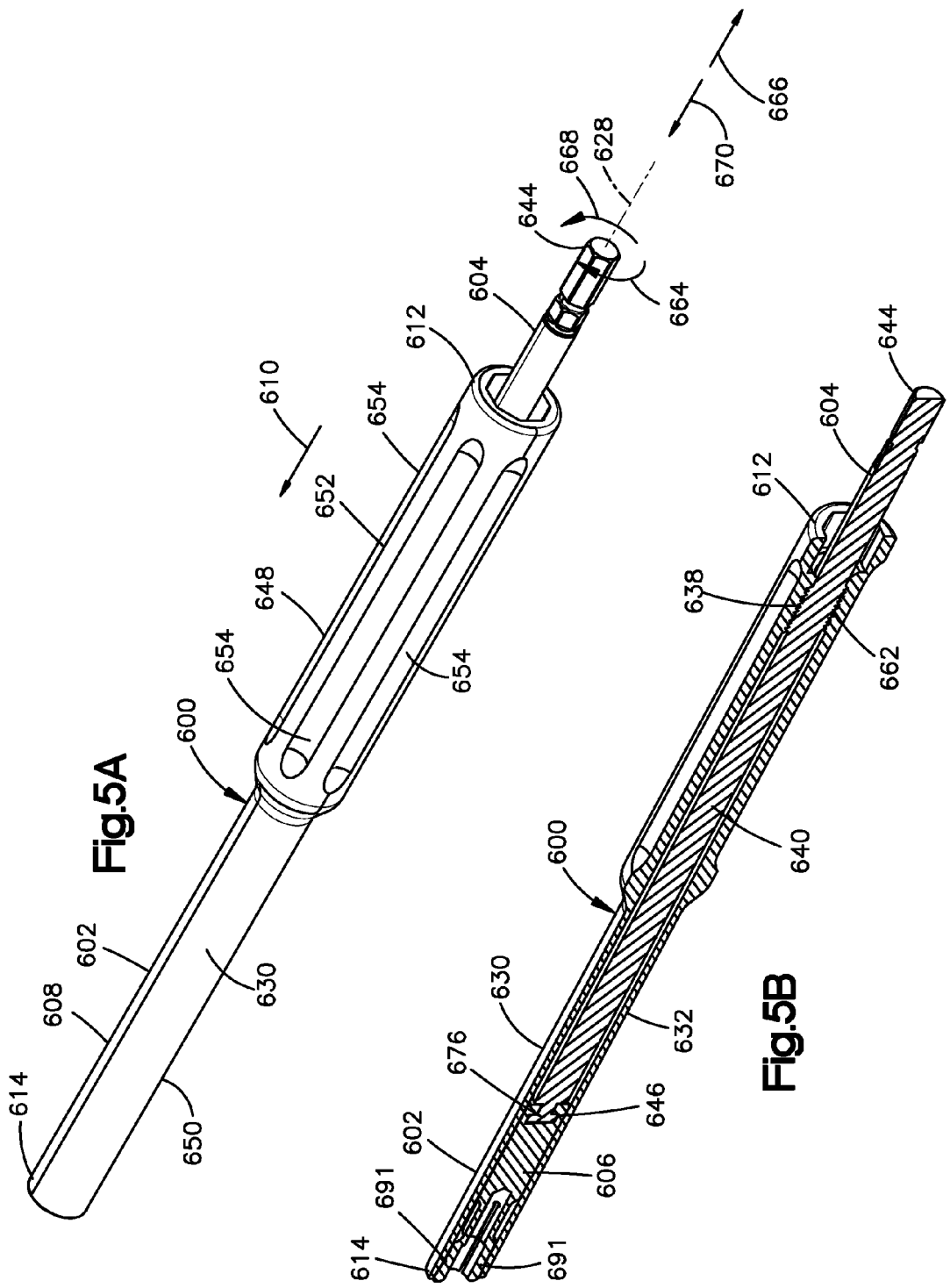

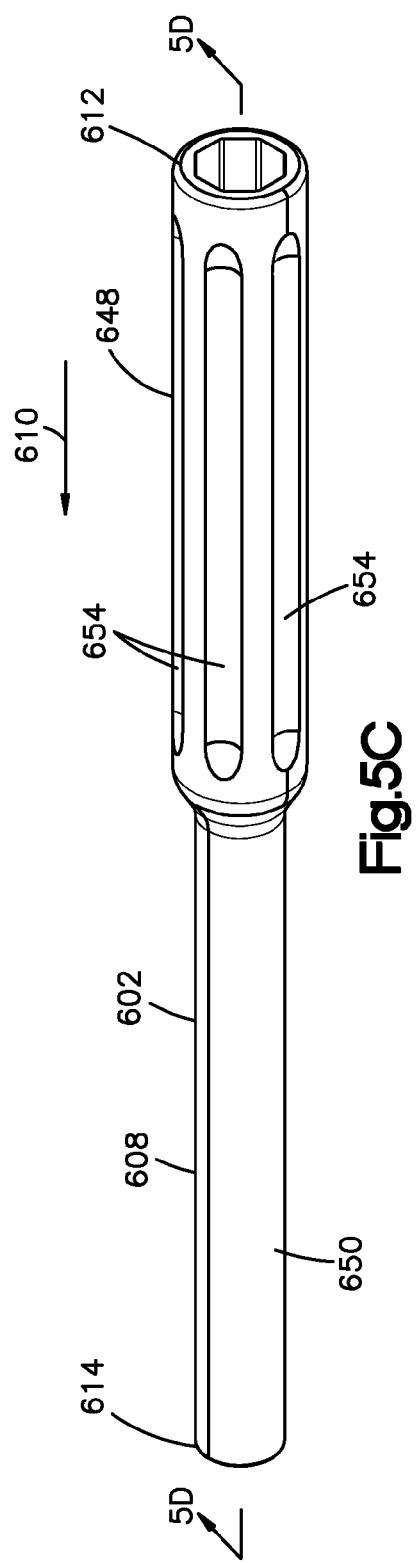
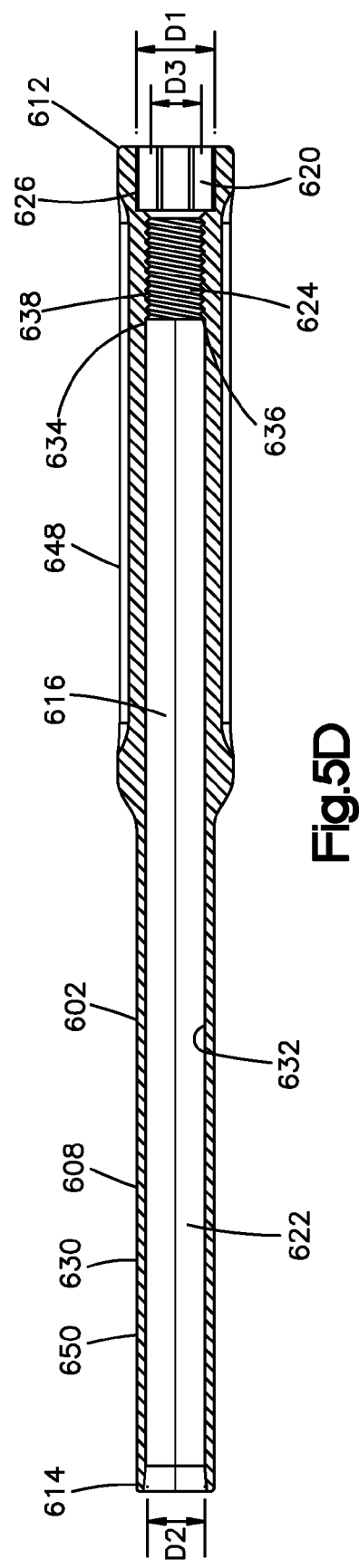
Fig.5C
Fig.5D

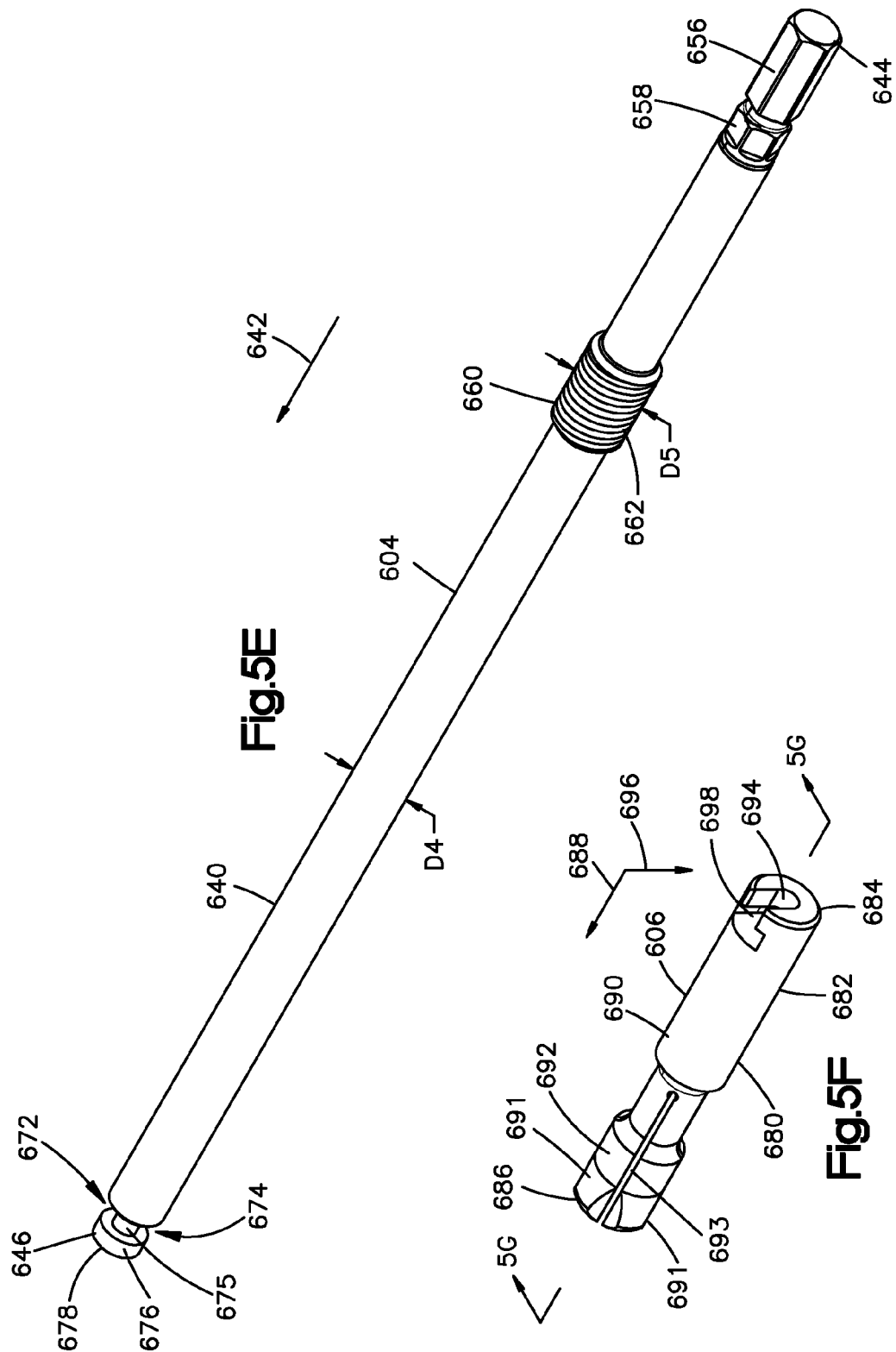

MINIMALLY INVASIVE SPINAL FIXATION SYSTEM INCLUDING VERTEBRAL ALIGNMENT FEATURES

CROSS-REFERENCE TO RELATED APPLICATION

The present application claims the priority, and the benefit of, U.S. Provisional Patent Application No. 61/490,689 filed on May 27, 2011, the entire disclosure of which is herein incorporated by reference.

TECHNICAL FIELD

The present disclosure relates to minimally invasive fixation system, and more particular, to Schanz bone screw based pedicle screw fixation system that includes vertebral alignment features.

BACKGROUND

Spinal stabilization and spinal fusion are procedures that involve joining two or more adjacent vertebrae with a bone fixation device to restrict movement of the vertebra with respect to one another. Spinal fixation devices can be used to perform spinal stabilization or spinal fusion. In particular, spinal fixation devices are used in spine surgery to align, stabilize or fix a desired relationship between adjacent vertebral bodies. Such devices typically include a spinal fixation member, such as a relatively rigid fixation rod, a dynamic or flexible spinal rod, or a suitable a longitudinal rod, that is coupled to adjacent vertebrae by attaching the spinal fixation member to various bone anchor, such as, hooks, bolts, wires, and screws. The bone anchor may commonly include heads with channels in which the longitudinal rod is inserted and subsequently clamped by a set screw or closure cap. Surgeons may commonly choose to install multiple bone anchors, as well as multiple spinal fixation members, to treat a given spinal disorder. The spinal fixation member may have a predetermined contour, and once installed, the longitudinal rod may hold the vertebrae in a desired spatial relationship, either until desired healing or spinal fusion has taken place, or for some longer period of time.

The process of positioning and setting the vertebrae may involve adjusting the angular orientation of the bone anchors relative to the spinal stabilization member along the sagittal plane in order to angularly correct the spine. (i.e., sagittal angular correction). The sagittal angular correction of the spine can be performed, for example, to correct kyphosis. In some conventional spinal stabilization systems, the sagittal angular correction of the spine is achieved by adjusting the position of the patient. In some others, it is done via an open surgery which includes a long incision which can result in long recovery times.

SUMMARY

The present application relates to a bone anchor coupler assembly that is configured to couple a bone screw to a spine stabilization rod. The bone screw may define a screw length that ranges between about 30 millimeters and about 260 millimeters. In one embodiment, the bone anchor coupler assembly includes a coupler body, and an angular adjustment member movably coupled to the coupler body. The coupler body defines a first coupler opening and a second coupler opening that is spaced from the first coupler opening along a lateral direction. The first coupler opening is configured to receive a portion of the bone screw that is configured to be attached to a first vertebra. The second coupler opening is configured to receive a portion of the spine stabilization rod. The second coupler opening defines a top open end and an opposed closed bottom end that is spaced from the top open end along a transverse direction that is substantially perpendicular to the lateral direction. The top open end is configured to facilitate posterior insertion of the portion of the spine stabilization rod in the second coupler opening. The angular adjustment member is movably coupled to the coupler body such that the bone screw is configured to move relative to the coupler body when the portion of the bone is received in the first coupler opening to adjust a position of the first vertebra relative to a second vertebra when the bone screw is attached to the first vertebra.

The angular adjustment member may be configured as a pivot member that is pivotally coupled to the coupler body such that the bone screw is configured to pivot relative to the coupler body when the portion of the bone is received in the first coupler opening to adjust an angular position of the first vertebra relative to a second vertebra when the bone screw is attached to the first vertebra.

The bone anchor coupler assembly may further include a collet configured to be partially disposed in the first coupler opening. The collet defines a collet opening that is configured to receive at least a portion of the bone screw. The collet may be configured to be coupled to the pivot member such that pivotal movement of the pivot member relative to the coupler body causes a corresponding pivotal movement of the collet relative to the coupler body. The bone anchor coupler assembly may further include a fastener movably coupled to the collet such that rotation of the fastener about the collet causes the collet to move between an unlocked position in which the collet is configured to pivot relative to the coupler body, and a locked position in which the collet is fixed relative to the coupler body to fix a position of the bone screw relative to the coupler body. The first coupler opening may define a cross-sectional dimension that decreases in the transverse direction, and the collet includes a compressible portion. In operation, the rotation of the fastener causes configured to move the collet between the unlocked position and the locked position in which the compressible portion is press-fitted in the first coupler opening.

The bone anchor coupler assembly may further include a locking cap configured to be at least partially disposed in the second coupler opening to lock at least a portion of the spine stabilization rod in the second coupler opening. The coupler body may define a top body surface that defines a substantially arc-shape, and the pivot member defines a lower pivot surface that defines a substantially concave shape that substantially corresponds to the substantially arc shape of the top body surface such that the pivot member is configured to move along the top body surface. The bone anchor coupler assembly may further include coupler teeth that protrude from the coupler body. The coupler teeth are disposed along the top body surface. The pivot member includes a pivot body. In addition, the pivot member may further include pivot teeth that protrude from the pivot body. The pivot teeth may be configured to mate with the coupler teeth such that the pivot member is configured to incrementally pivot relative to the coupler body. Alternatively or additionally, the pivot teeth can be configured to press against the top body surface of the coupler body.

The angular adjustment member may be configured as a polyaxial connection member. The polyaxial connection member is configured to couple the bone screw to the coupler body. The polyaxial connection member is configured to be partially received in the first coupler opening such that polyaxial connection member is configured to rotate relative to the coupler body, thereby causing the bone screw to rotate relative to the coupler body when the bone screw is coupled to the polyaxial connection member. The coupler body defines an inner coupler surface that defines the first coupler opening, and polyaxial connection member defines a substantially spherical outer surface that substantially matches a shape of the inner coupler surface to facilitate polyaxial angulation of the polyaxial connection member relative to the coupler body.

The present disclosure also relates to a minimally invasive spinal stabilization system configured to move a first vertebra relative to a second vertebra between an initial position and an adjusted position. In one embodiment, the minimally invasive spinal stabilization system includes a bone screw configured to be attached to the first vertebra; and a bone anchor coupler assembly that is configured to couple the bone screw to a spine stabilization rod. The bone screw may define a screw length that ranges between about 30 millimeters and about 260 millimeters. The bone anchor coupler assembly includes a coupler body that defines a first coupler opening and a second coupler opening that is spaced from the first coupler opening along a lateral direction. The first coupler opening is configured to receive a portion of the bone screw. The second coupler opening is configured to receive a portion of the spine stabilization rod. The bone anchor coupler assembly is configured to be coupled to the bone screw such that the bone screw is configured to move relative to the spine stabilization rod to move the first vertebra relative to the second vertebra between the initial position and the adjusted position when the bone screw is attached to the first vertebra and the spine stabilization rod is at least partly disposed in the second coupler opening.

The bone anchor coupler assembly is configured to be coupled to the bone screw such that the bone screw is configured to angularly move relative to the spine stabilization rod to angularly move the first vertebra relative to the second vertebra. The bone anchor coupler assembly may be configured to be coupled to the to the bone screw such that the bone screw is configured to translate relative to the spine stabilization rod to translate the first vertebra relative to the second vertebra between the initial position and the adjusted position. The first vertebra may be closer to the second vertebra in the adjusted position than in the initial position. Alternatively, the first vertebra is farther from the second vertebra in the adjusted position than in the initial position. The minimally invasive spinal stabilization system may further include a coupler holder that is configured to hold at least a portion of the bone anchor coupler assembly, and a fastener guide that is configured to be coupled to the coupler holder via a ratchet mechanism such that the fastener guide is configured to move incrementally relative coupler holder. The minimally invasive spinal stabilization system may further include a bone anchor removal tool that includes a fork that is configured to receive at least a portion of the bone screw, and a sleeve at least partially surrounding the fork, wherein rotation of the fork relative to the sleeve causes the sleeve to translate relative to the fork and apply an inward force to the fork such that the fork tightens about the bone screw.

The present disclosure also relates to a method of adjusting a spatial relation between a first vertebra and a second vertebra with a coupler. The coupler may include a coupler body that defines a first coupler opening and a second coupler opening that is spaced from the first coupler opening along a lateral direction, the second coupler opening defining a top open end and an opposed closed bottom end that is spaced from the top open end along a transverse direction. The transverse direction may be substantially perpendicular to the lateral direction. In an embodiment, the method includes the following steps: (a) attaching a Schanz bone screw to the first vertebra; (b) coupling the coupler body to the Schanz bone screw such that at least a portion of the Schanz bone screw is disposed in the first coupler opening; (c) positioning the spine stabilization rod in the second coupler opening by advancing at least a portion of the spine stabilization rod through the top open end; and (d) moving the Schanz bone screw relative to the spinal stabilization rod to adjust the spatial relation between the first vertebra relative to a second vertebra. The moving step may include translating or angulating the Schanz bone screw relative to relative to the spinal stabilization rod to move the first vertebral relative to the second vertebra. The moving step may include angulating the Schanz bone screw with respect to spinal stabilization rod to angulate the first vertebra relative to the second vertebra.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 3A is a perspective view of another embodiment of a polyaxial bone anchor coupler assembly that includes a coupler, a collet, a first fastener, and a second fastener;

FIG. 4H is a perspective view of a fastener guide that is configured to hold the second fastener shown in FIG. 2A;

FIG. 4I is a perspective view of a distal portion of the fastener guide shown in FIG. 4H coupled to the second fastener shown in FIG. 1A;

FIG. 5A is a perspective view of a bone anchor removal tool that is configured to remove a bone anchor from a vertebra, the bone anchor removal tool including a sleeve, a fork, and actuator;

FIG. 5B is a sectional view of the bone anchor removal tool shown in FIG. 5A, taken along section line 5B-5B;

FIG. 5C is a perspective view of the sleeve shown in FIG. 5A;

FIG. 5D is a cross-sectional view of the of the sleeve shown in FIG. 5C, taken along section line 5D-5D;

FIG. 5E is a perspective view of the actuator shown in FIG. 5A;

FIG. 5F is a perspective view of the fork of the bone anchor removal tool shown in FIG. 5A;

DETAILED DESCRIPTION OF THE DRAWINGS

Figure 1A:
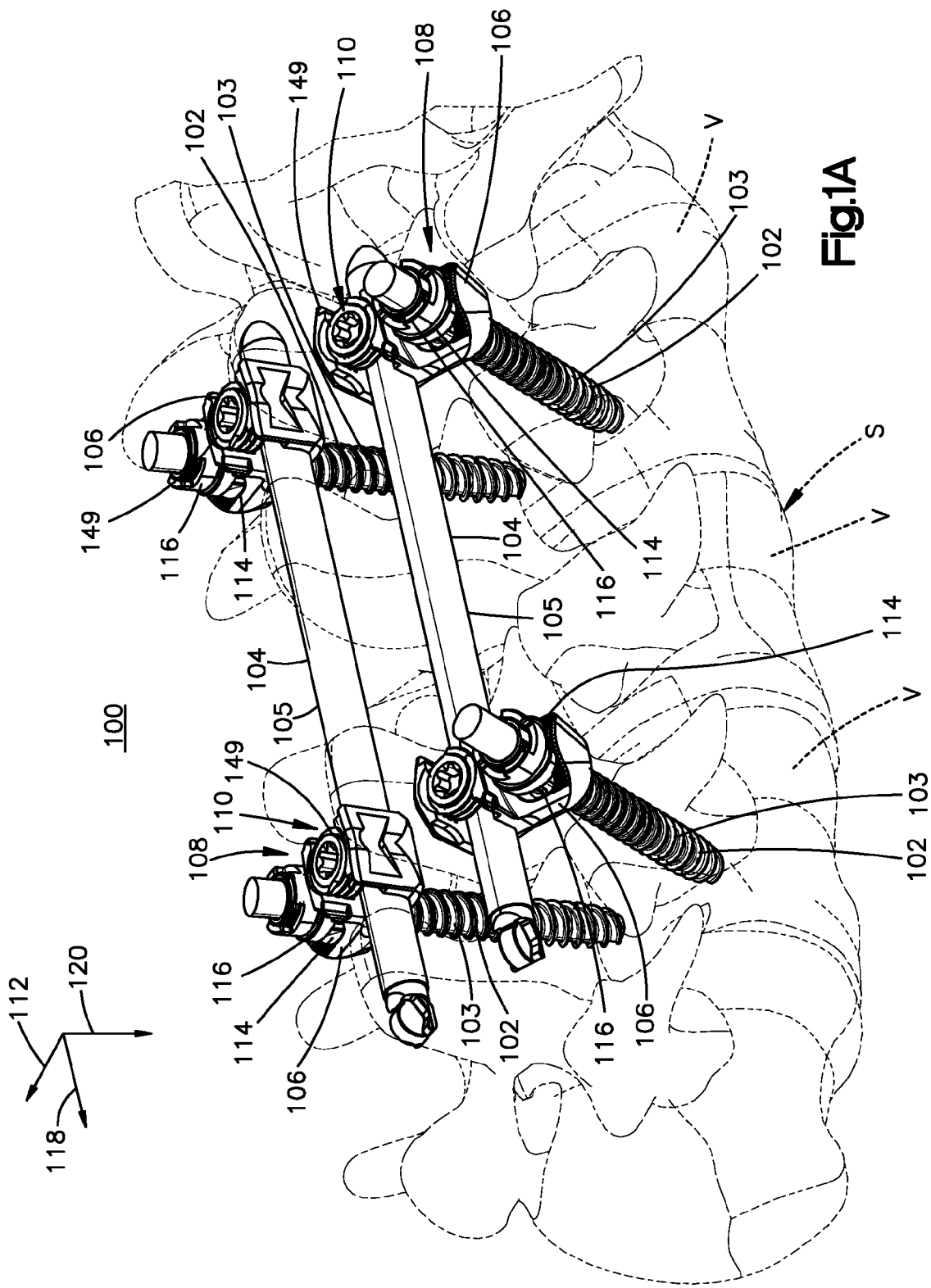
FIG. 1A is a perspective view of a minimally invasive spinal stabilization system according to an embodiment that includes bone anchors, spine stabilization members, and bone anchor clamp assemblies each coupling at least one bone anchor to one spine stabilization member.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device. The words, "anterior", "posterior", "superior", "inferior" and related words and/or phrases designate preferred positions and orientations in the human body to which reference is made and are not meant to be limiting. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. The terminology includes the above-listed words, derivatives thereof and words of similar import.

With reference to FIG. 1A, a minimally invasive spinal stabilization system 100 is configured to stabilize at least a portion of a spine S. In operation, the minimally invasive spinal stabilization system 100 can be inserted into a patient's body using known minimally invasive techniques, thereby minimizing iatrogenic trauma. All or some of the components of the spinal stabilization system 100 can be inserted into a patient's body using a posterior minimally invasive approach. That is, all or some of the components that include the spinal stabilization system 100 can be inserted into a desired surgical site through the patient's back. The spinal stabilization system 100 can stabilize at least a portion of the spine once attached to the spine. Specifically, the spinal stabilization system 100 can align, stabilize, or fix the spatial and angular relationships between two or more vertebrae V once attached to the spine S as desired.

Figure 4A:
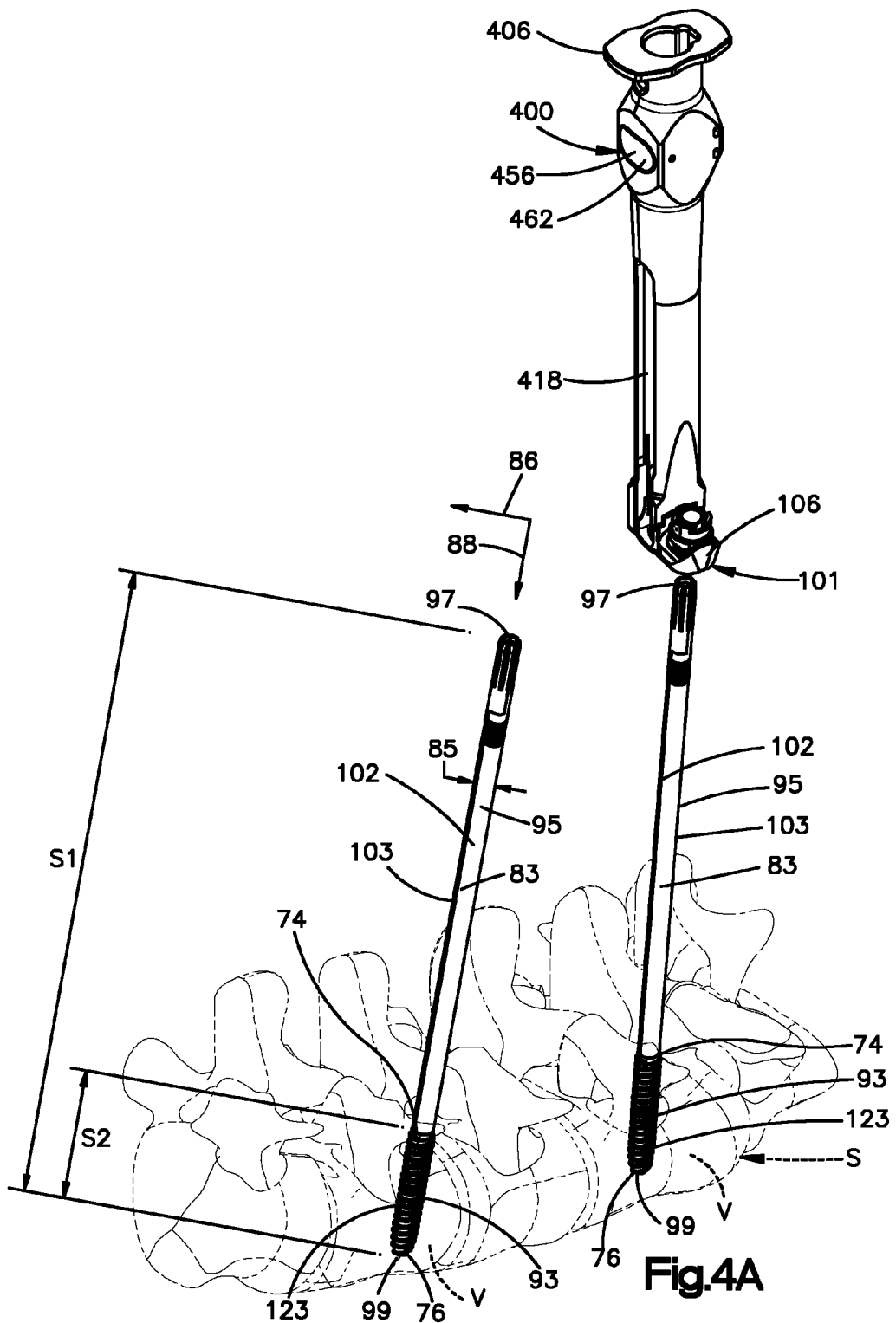
FIG. 4A is a perspective view of a perspective view of a coupler holder coupled to a portion of the bone anchor coupler assembly shown in FIG. 2A being advanced toward a bone anchor attached to a vertebra of a spine.

In the depicted embodiment, the spinal stabilization system 100 can generally include a plurality of bone anchors 102, such as Schanz bone screws 103, a plurality of spine stabilization members 104, such as spine stabilization rods 105, and a plurality of couplers 106 that are each configured to couple a spine stabilization member 104 to a bone anchor 102. The bone anchors 102 can include, but is not limited to, bone screws, pins, nails or any apparatus, device, or means capable of being inserted in bone. In one embodiment, one or more bone anchors 102 can be configured as an external fixation member, such as a Schanz bone anchor. The Schanz bone anchors can include, but are not limited to, Schanz screws, Schanz pins, Schanz bolts, Schanz nail or any apparatus or means capable of being manipulated externally (i.e, outside the patient's body) while being attached to bone. The bone anchors 102 are configured to be inserted into a bone such as one of the vertebrae V. Any of the couplers described herein can be configured as clamps. At least one of the Schanz bone screws 103 defines a first screw end 97 (FIG. 4A) and a second screw end 99 (FIG. 4A).

With continuing reference to FIG. 1A, the spinal stabilization system 100 further includes couplers 106 that are configured to couple to at least one bone anchor 102 to at least one spine stabilization member 104. Each of the couplers 106 defines at least a first coupler opening 108 and a second coupler opening 110 that is spaced from the first coupler opening 108 along a lateral direction 112. The first coupler opening 108 is configured and sized to receive at least a portion of one of the bone anchors 102. The second coupler opening 110 is configured and sized to receive at least a portion of one of the spinal stabilization members 104. The bone anchor 102 can be inserted through the first coupler opening 108 and a portion of the spine stabilization member 104 can be disposed in the second coupler opening 110 so as to couple the spine stabilization member 104 to the bone anchor 102.

With continuing reference to FIG. 1A, the spinal stabilization system 100 further includes a plurality of pivot members 114. Each pivot member 114 can pivotally couple one of the bone anchors 102 to one of the coupler bodies 122 such that the bone anchor 102 can pivot relative to the coupler body 122 when the bone anchor 102 is disposed through the second coupler opening 110. As discussed in detail below, each pivot member 114 can be configured as a washer 116 that is configured and sized to surround at least a portion of the bone anchor 102. The washer 116 can also be pivotally coupled to the coupler body 122.

With continuing reference to FIG. 1A, as discussed above, the spinal stabilization system 100 can further include one or more spine stabilization members 104. The spine stabilization members 104 can be configured as spine stabilization rods 105. When the spinal stabilization system 100 is completed assembled and the bone anchors 102 are attached to the vertebrae V, the spine fixation members can be elongate along a longitudinal direction 118. The longitudinal direction 118 may be substantially perpendicular to the lateral direction 112. Each spine stabilization member 104 can be configured and sized to be disposed in the second coupler opening 110. As discussed in detail below, each spine stabilization member 104 can be coupled to one or more couplers 106 using a second fastener 149 such as a locking cap. Thus, the second fastener 149 can also be referred to as the locking cap 91. The holder section With continuing reference to FIG. 1A, in operation, the bone anchors 102 can be inserted in more than one vertebra V. In particular, the bone anchors 102 can be inserted posteriorly. Thus, to attach the bone anchors 102 to the vertebrae V, the bone anchors 102 can be advanced in a transverse direction 120 until the bone anchors 102 are disposed in a portion of the vertebra such as the pedicle (i.e., top loading approach). The transverse direction 120 is substantially perpendicular to the longitudinal direction 118 and the lateral direction 112. At least two bone anchors 102 can be inserted in two different vertebrae V such that the bone anchors 102 are spaced apart from each other along the longitudinal direction 118. Then, one coupler 106 is coupled to each bone anchor 102 such that the bone anchor 102 is partially disposed in the first coupler opening 108. One spine stabilization member 104 is then coupled between two couplers 106 that are spaced apart from each other along the longitudinal direction 118. The position and orientation of the spine stabilization member 104 can then be fixed relative to the two couplers 106. Similarly, the orientation and position of the bone anchors 102 can be fixed relative to the couplers 106.

Figure 1B:
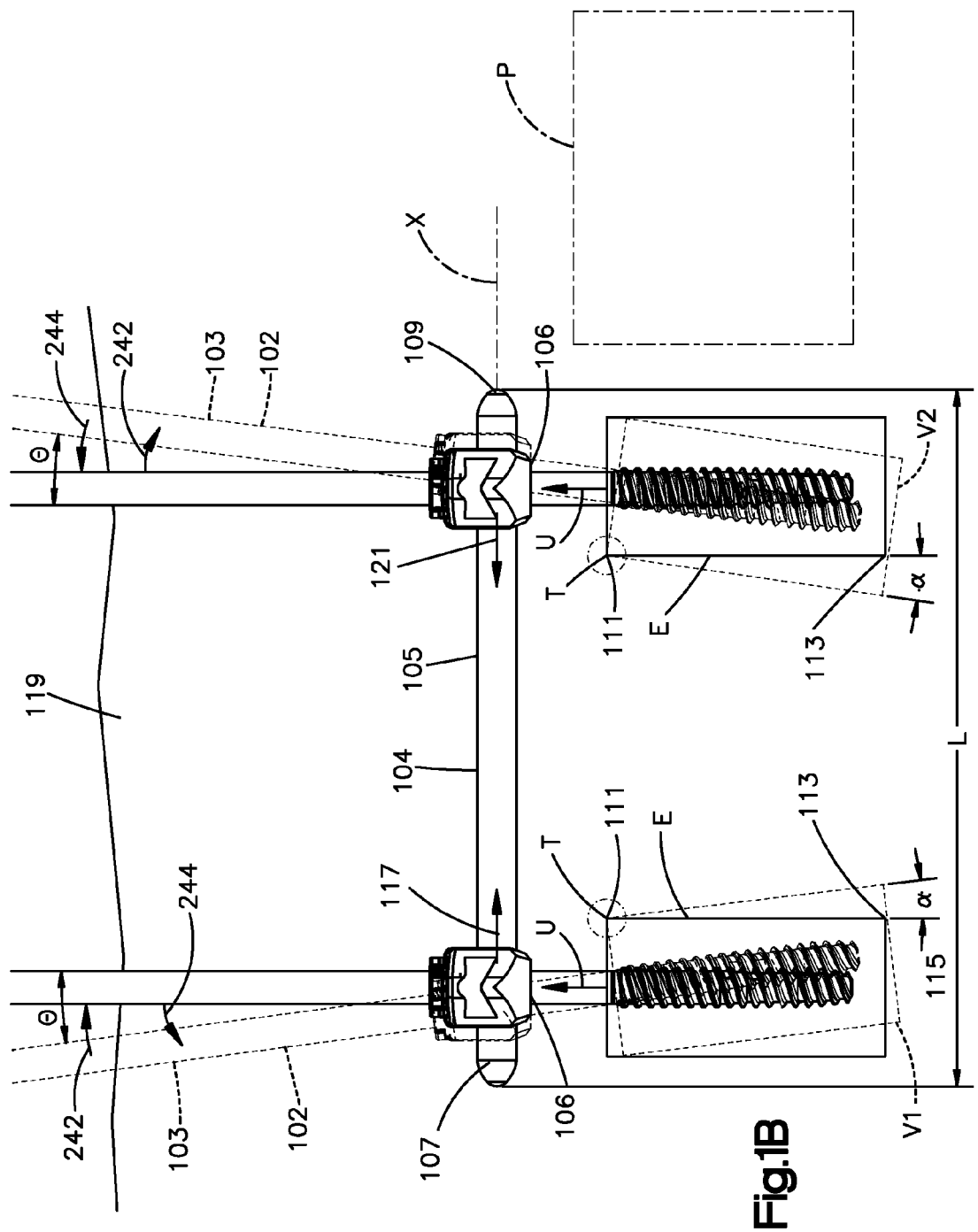
FIG. 1B is a side view of the minimally invasive spinal stabilization system shown in FIG. 1A, depicting the movement of the bone anchor relative to the bone anchor clamp assemblies when the bone anchors are attached to first and second vertebrae.

With reference to FIG. 1B, before fixing the position and orientation of the bone anchors 102 relative to the couplers 106, the angular orientation of the vertebrae relative to another can be adjusted by manipulating the bone anchors 102 that are attached to those vertebrae. As discussed above, the bone anchors 102 can be configured as Schanz bone screws 103 that can be manipulated from outside of the patient's body 119. After attaching the bone anchors 102 to first vertebra V1 and the second vertebra V2, and coupling the spine stabilization member 104 between two bone anchors 102 via the two couplers 106, the bone anchors 102 can be manipulated from outside the patient's body 119 to adjust the angular orientation of the one vertebra relative to another vertebra along a sagittal plane P of the patient's body 119. In particular, at least one of the bone anchors 102 can be pivoted relative to the coupler 106 in a first pivotal direction 242 or an opposed second pivotal direction 244 between an initial bone anchor position and an angled bone anchor position. In the initial bone anchor position, the bone anchor 102 is oriented at a substantially right angle (i.e., about 90 degrees) relative to a longitudinal axis X defined along a length L of the spine stabilization member 104. The length L is defined from a first longitudinal end 107 and a second longitudinal end 109 of the spine stabilization member 104. Thus, the spine stabilization member 104 can be elongate along the longitudinal axis X. In the angled position, the bone anchor 102 can be oriented at an oblique angle θ relative to the longitudinal axis X of the spine stabilization member 104. The maximum oblique angle θ can range between about ±30 degrees. In an embodiment, the maximum oblique angle θ can be about ±20 degrees.

In operation, the movement of at least one of the bone anchors 102 between the initial bone anchor position and the angled position causes the vertebra to which such bone anchor 102 is attached (i.e., the first or second vertebrae V1 or V2) to pivot about a pivot location T of the corresponding vertebra, thereby angularly moving vertebra along the sagittal plane P. The pivot location T can be located at an end of the endplate of the vertebra V1 or V2. Specifically, each of the first and second vertebrae V1, V2, includes an endplate E that defines a first endplate end 111 and a second endplate end 113. The pivot location T can be at first endplate end 111. Each endplate E defines an endplate axis 115 defined between the first endplate end 111 and the second endplate end 113. When the bone anchor 102 attached, for example, to the first vertebra V1 and is located at the initial bone anchor position, the first vertebra V1 is at an initial vertebra position, where the endplate axis 115 defines a substantially right angle (i.e., about 90 degrees) with respect to the longitudinal axis X. The movement the bone anchor 102 attached to the first vertebra V1 causes the first vertebra V1 to move pivot about the pivot location T between the initial vertebra position and an angled vertebra position. In the angled vertebra position, the first vertebra V1 is angled such that the endplate axis 115 defines an oblique angle α with respect to the endplate axis 115 at the initial vertebra position. The maximum oblique angle α can range between about ±15 degrees and about ±25 degrees. The maximum oblique angle α can be about ±20 degrees. The method of angularly moving the first vertebra V1 can also be used to move the second vertebra V2.

With continuing reference to FIG. 1B, the spinal stabilization system 100 can also be configured to move the first and second vertebrae V1, V2 axially toward or away from each other. After the bone anchors 102 have been attached to the first and second vertebrae V1, V2 and at least two bone anchors 102 have been coupled to one spine stabilization member 104 via couplers 106, at least one of the bone anchors 102 can be moved relative to the bone anchor 102 along the spine stabilization member 104 in a first axial direction 117 or a second axial direction 121 in order to adjust the distance between the first vertebra V1 and the second vertebra V2. The movement of the bone anchors 102 toward each other causes compression of the spine, whereas the movement of the bone anchors 102 away from each other causes distraction of the spine. Once the desired distance between the first vertebra V1 and the second vertebra V2 has been achieved, the position of the couplers 106 relative to the spine stabilization member 104 can be fixed using the second fastener 149 as discussed below. By using the spinal stabilization system 100, the distraction/compression of the spine and the angular correction of the spine can be performed independently from each other and in no particular order. For example, a user may distract the spine and then performed angular correction. Alternatively, the user may first conduct angular correction of the spine and then perform compression of the spine. Further still, the user may compress the spine and then perform angular correction. Also, the user may first conduct angular correction and then conduct distraction of the spine.

With continuing reference to FIG. 1B, the spinal stabilization system 100 can also be used for reduction of spondylolisthesis. Spondylolisthesis is a condition in which a bone (vertebra) in the lower part of the spine slips out of the proper position onto the bone below it. To reduce a spondylolisthesis, at least one of the bone screws 102 can be attached to a bone, such as the first vertebra V1 or the second vertebra V2. Then, a force can be applied to at least one of the bone screws 102 in the U direction to move the vertebra (V1 or V2) that is attached to that bone screw in the U direction. The U direction may be substantially perpendicular to the first axial direction 117. In addition, the U direction may be substantially perpendicular to the second axial direction 121. However, it is envisioned that the U direction may extend substantially along the screw length of the bone screw 102. As such, the U direction may be angularly offset to the first axial direction 117. While the force is applied to one of the bone screws 102 in the U direction, the other bone screw 102 can be attached to the another bone, such as the second vertebra V2, and can remain stationary relative to that bone to which it is attached. For example, if one bone screw 102 is attached to the first vertebra V1 and another bone screw is attached to the second vertebra V2, a force can be applied to the bone screw 102 that is attached to the first vertebra V1 to move the first vertebra V1 relative to the second vertebra V2 in the U direction. Any suitable reduction tool can be used to apply to force to the bone screw 102 in the U direction. The spinal stabilization system 100 allows a surgeon to preform reduction of spondylolithesis intraoperatively. Furthermore, the spinal stabilization system 100 allows a surgeon to move a bone (such as vertebra V1 or vertebrae V2) in the U direction any desired distance. The U direction can be an anterior direction or a posterior direction. The U direction may be a transverse direction. For example, the U direction may be a direction opposite to the transverse direction 120 (FIG. 1A). Hence, the transverse direction 120 may be referred to as the first transverse direction, and the U direction may be referred to as the second transverse direction.

Figure 2A:
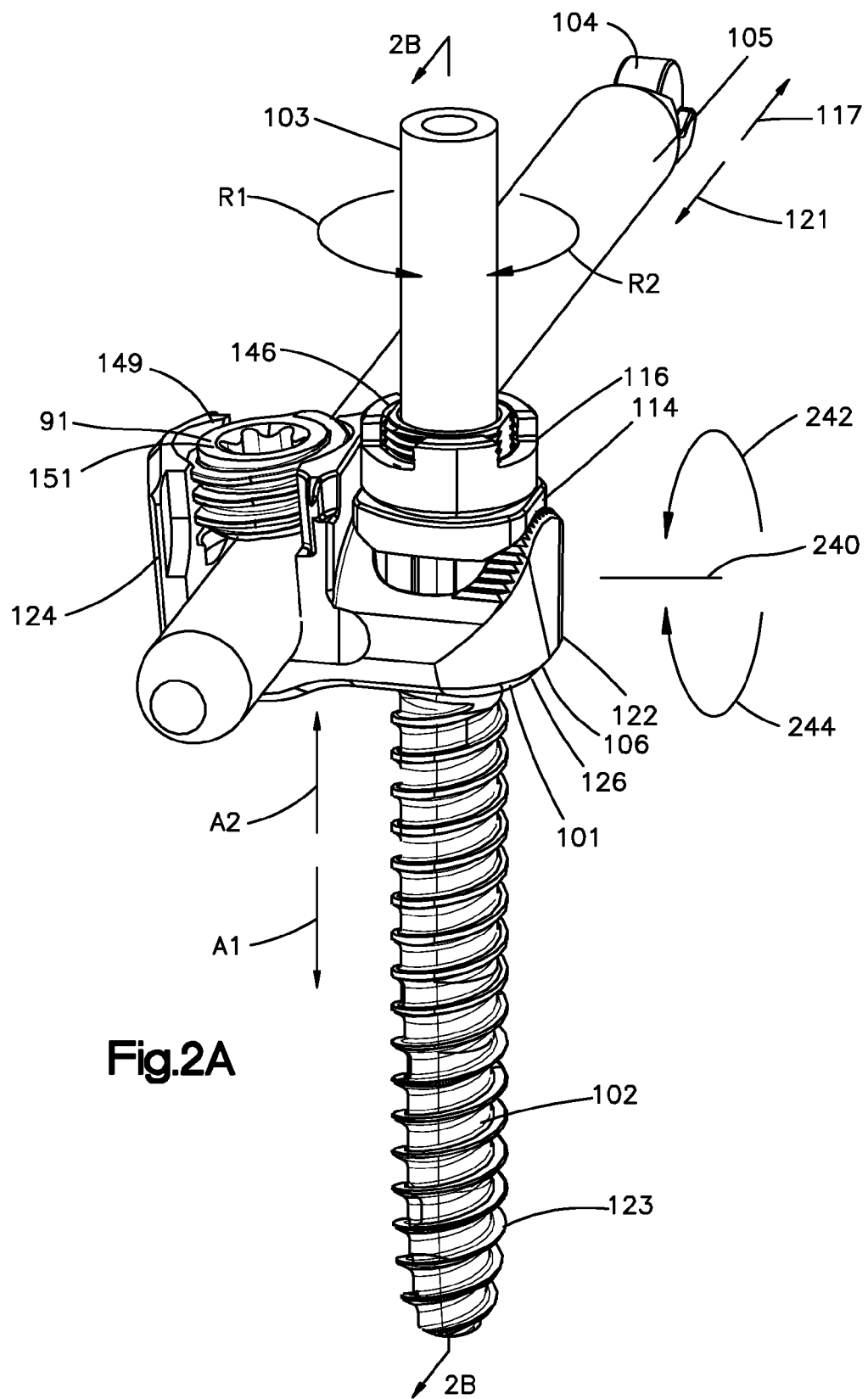
FIG. 2A is a perspective view of a portion of the minimally invasive spinal stabilization system shown in FIG. 1A, including a spine stabilization member, a bone anchor, and a bone anchor coupler assembly that in turn includes a coupler body, a collet, a pivot member, a first fastener, and a second fastener.
Figure 2B:
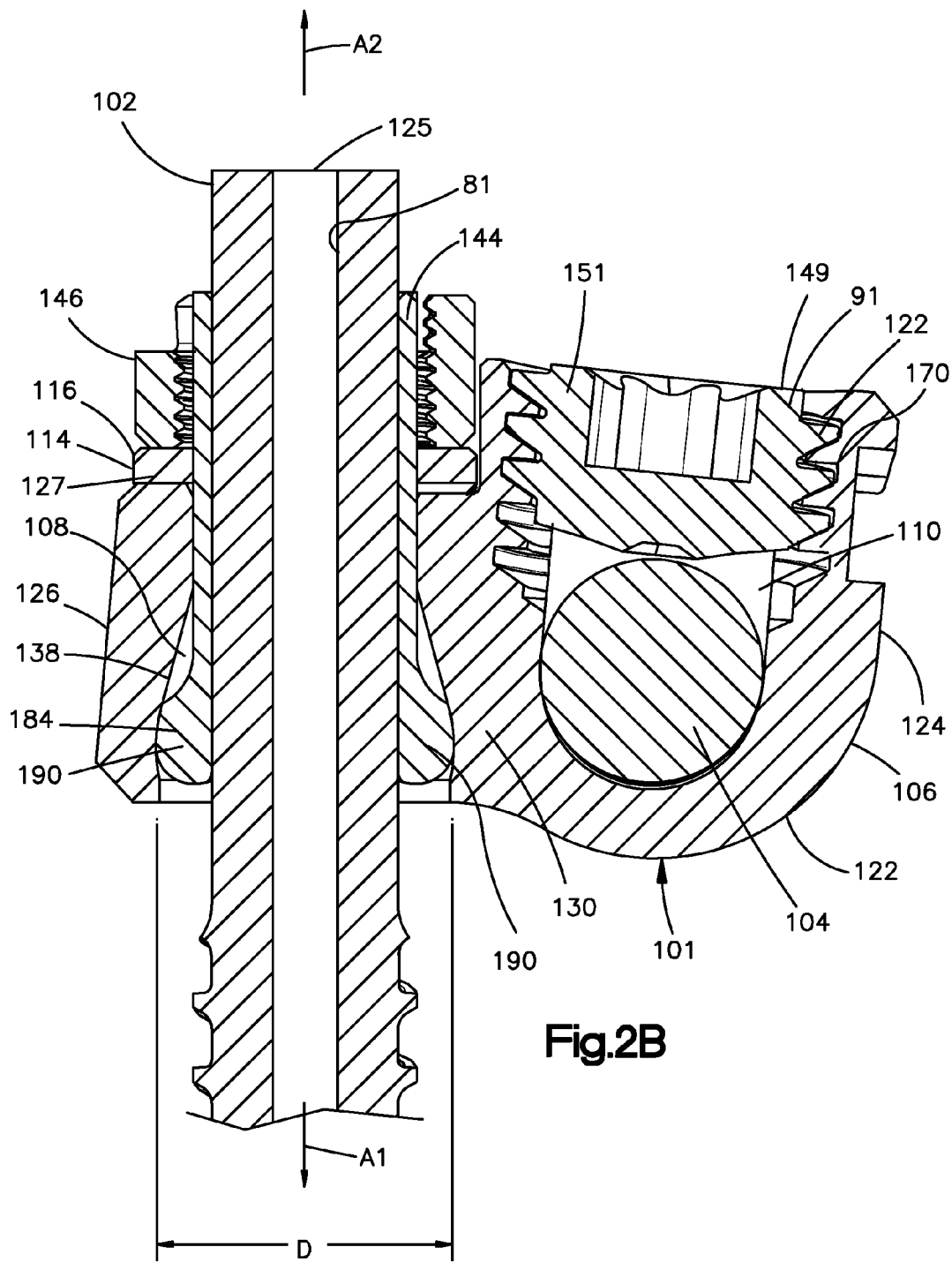
FIG. 2B is a cross-sectional view of the portion of the minimally invasive spinal stabilization system shown in FIG. 2A, taken along section line 2B-2B, showing the collet in a locked position.
Figure 2C:
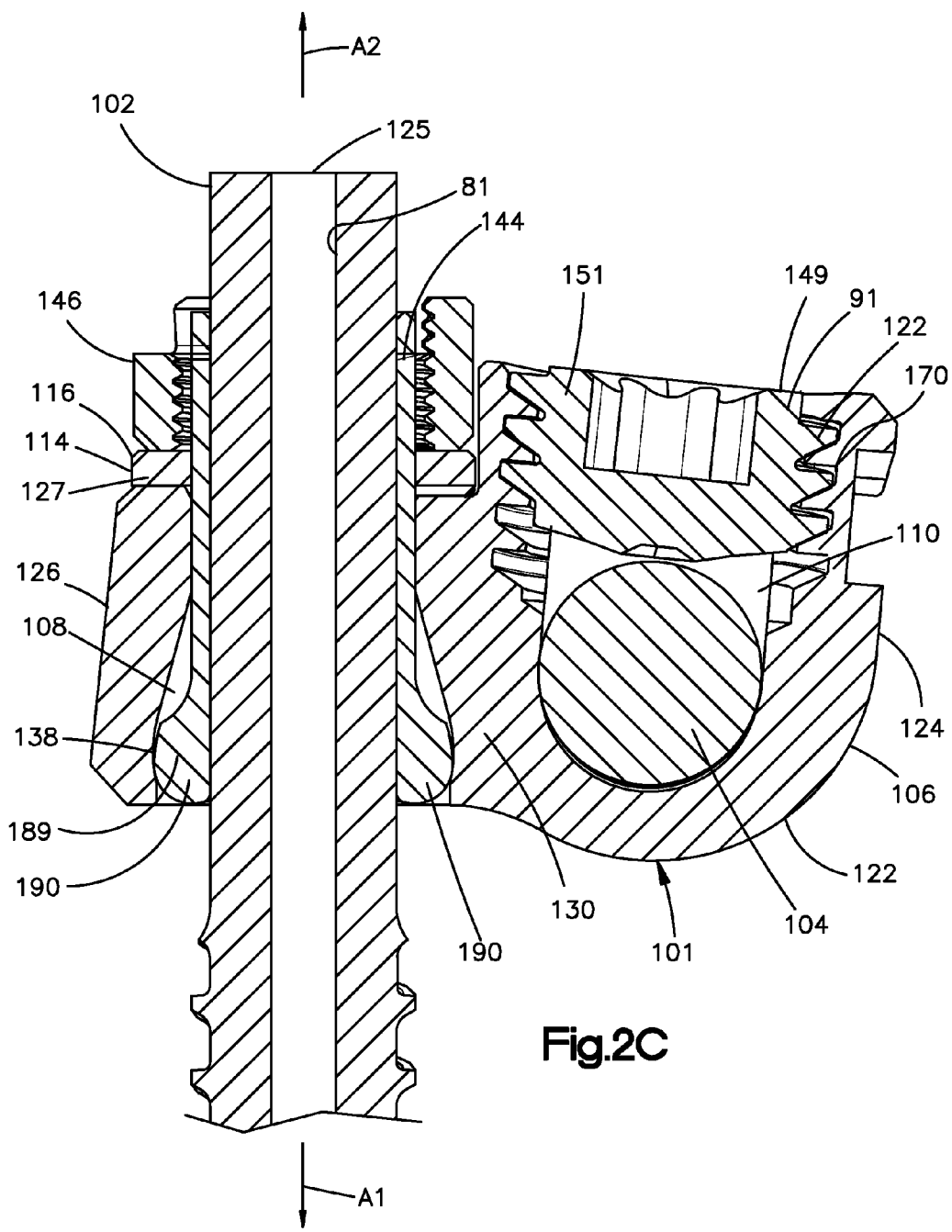
FIG. 2C is a cross-sectional view of the portion of the minimally invasive spinal stabilization system shown in FIG. 2A, taken along section line 2B-2B, showing the collet in an unlocked position.

With reference to FIGS. 2A-C, the minimally invasive spinal stabilization system 100 can generally include the coupler 106, which is configured to couple the spine stabilization member 104 to the bone anchor 102, the spine stabilization member 104 that is configured to be partially disposed in the second coupler opening 110, and the bone anchor 102 that is configured to be partially disposed in the first coupler opening 108. Further, the spinal stabilization system 100 can include the pivot member 114 that is configured to pivotally couple the bone anchor 102 to the coupler 106 when the bone anchor 102 is at least partially disposed in the first coupler opening 108. In addition to the pivot member 114, the spinal stabilization system 100 can further include a collet 144 that is configured and sized to be at least partially received in the first coupler opening 10, and a first fastener 146 that is configured to be coupled to the collet 144. The collet 144 can be coupled to the bone anchor 102 and the first fastener 146 can be coupled to the collet 144 such that the first fastener 146 can fix the position of the bone anchor 102 with respect to the coupler 106 when the bone anchor 102 is partially disposed in the first coupler opening 108 and at least a portion of the collet 144 surrounds a portion of the bone anchor 102. Aside from the first fastener 146, the spinal stabilization system 100 further includes the second fastener 149 that is configured and sized to be received in the second coupler opening 110 to secure the spine stabilization member 104 that is partially disposed in the second coupler opening 110. The coupler 106, the collet 144, the first fastener 146, the second fastener 149, and the pivot member 114 collectively form a bone anchor coupler assembly 101. The bone anchor coupler assembly 101 can also be referred to as the bone anchor clamp assembly. The bone anchor coupler assembly 101 can be configured to couple the spine stabilization member 104 to the bone anchor 102. Further, the bone anchor coupler assembly 101 can be part of the minimally invasive spinal stabilization system 100. The bone anchor coupler assembly 101 may be partly or entirely constructed from any biocompatible material known in the art including, but not limited to, stainless steel, titanium, titanium alloys, polymers, etc.

Figure 4B:
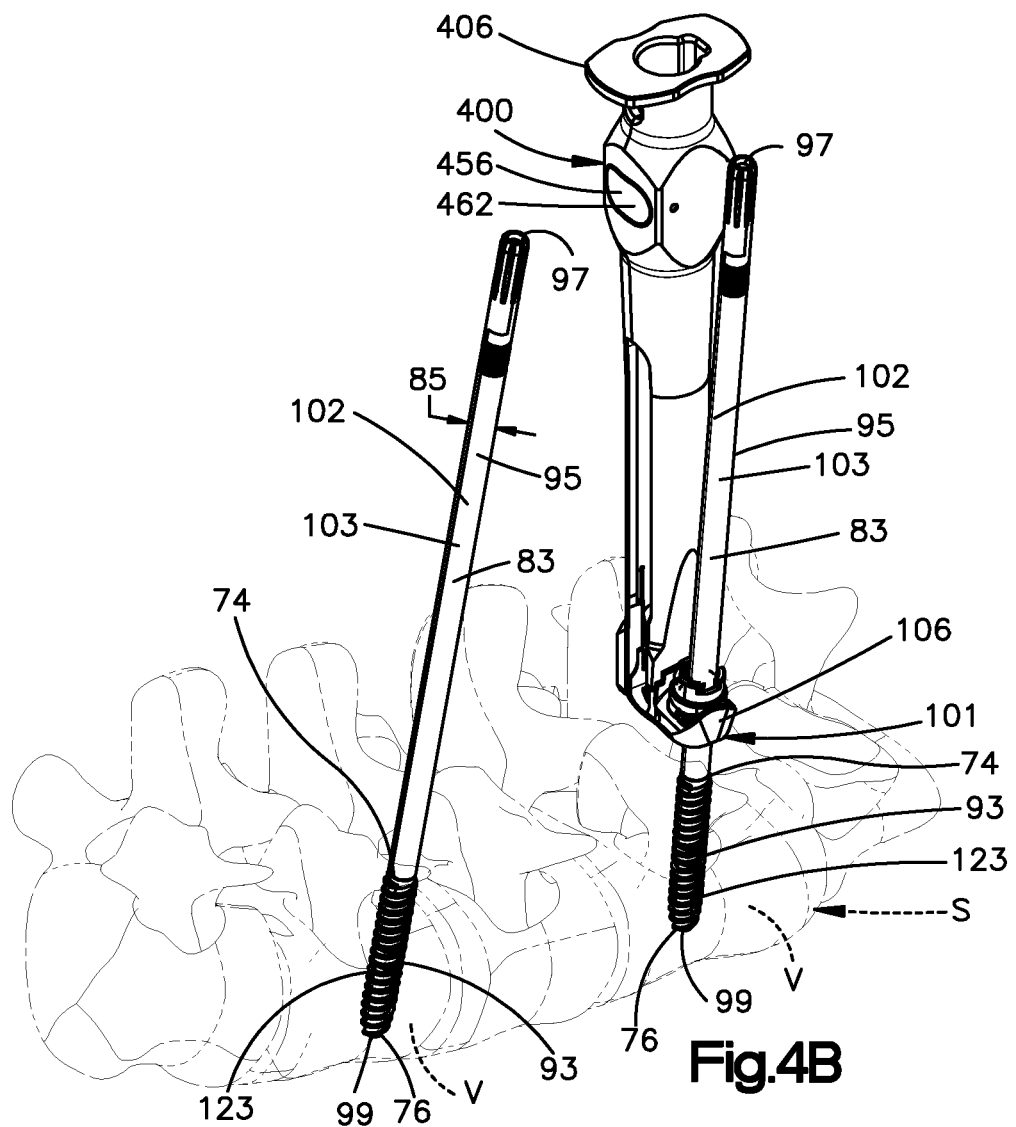
FIG. 4B is a perspective view of the coupler holder shown in FIG. 4A coupled to the bone anchor coupler assembly, and the bone anchor coupler assembly positioned coupled to the bone anchor attached to the vertebra of the spine.
Figure 4C:
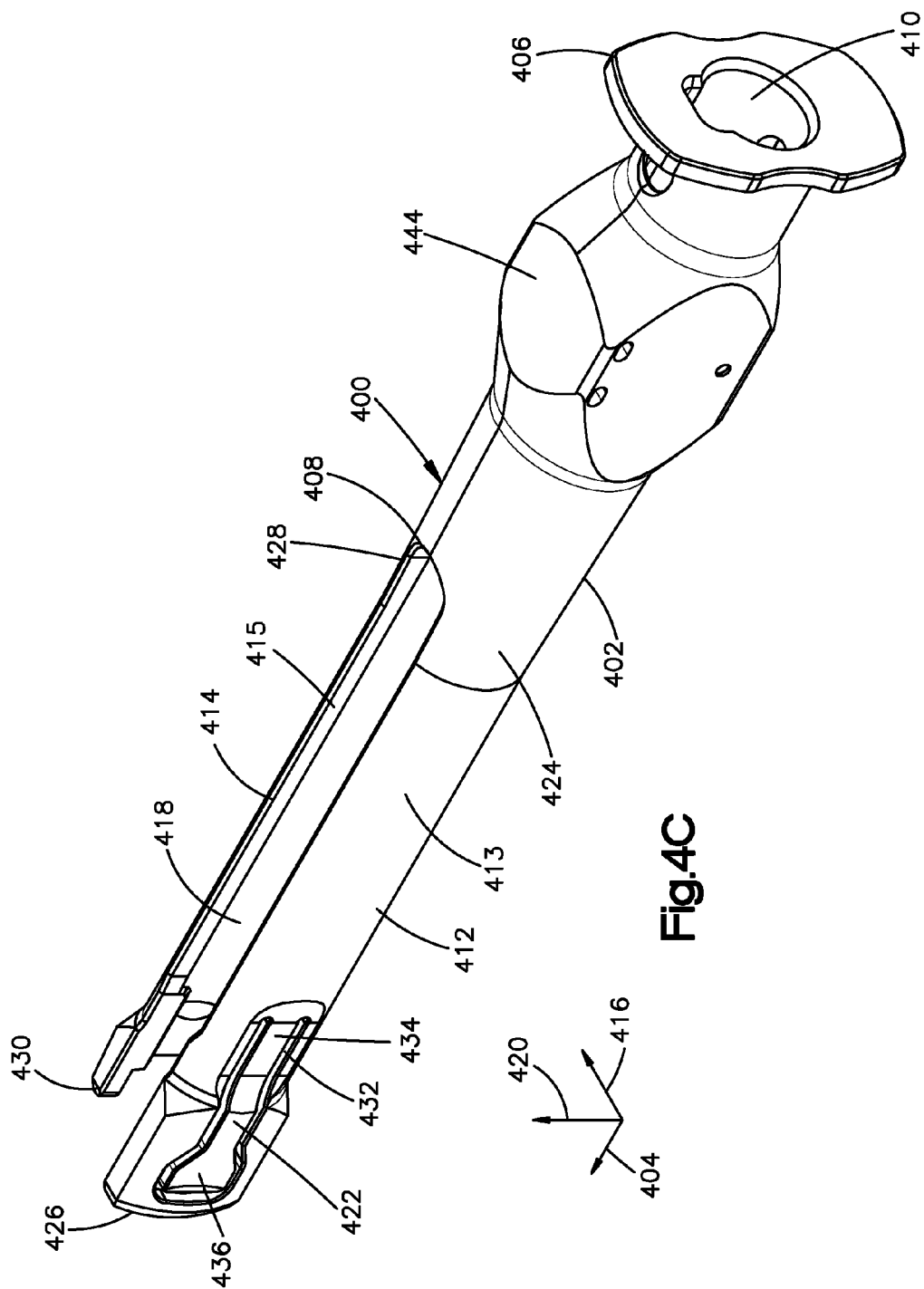
FIG. 4C is a perspective view of the coupler holder shown in FIG. 4A.
Figure 4D:
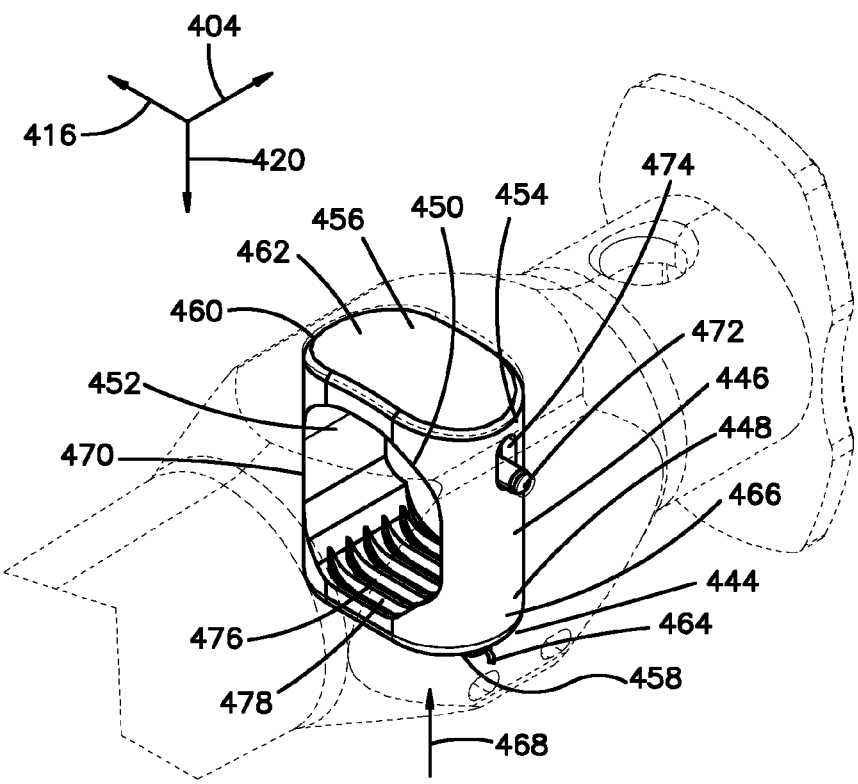
FIG. 4D is a perspective phantom view of the coupler holder shown in FIG. 4A, showing a front portion of a ratchet mechanism of the coupler holder.
Figure 4E:
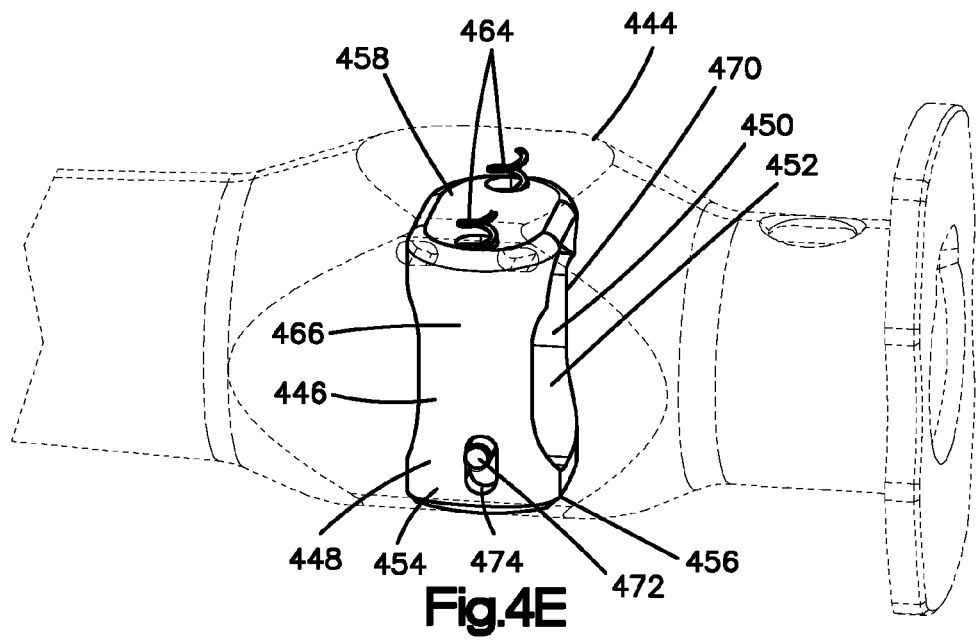
FIG. 4E is a perspective phantom view of the coupler holder shown in FIG. 4A, showing a rear portion of a ratchet mechanism of the coupler holder
Figure 4F:
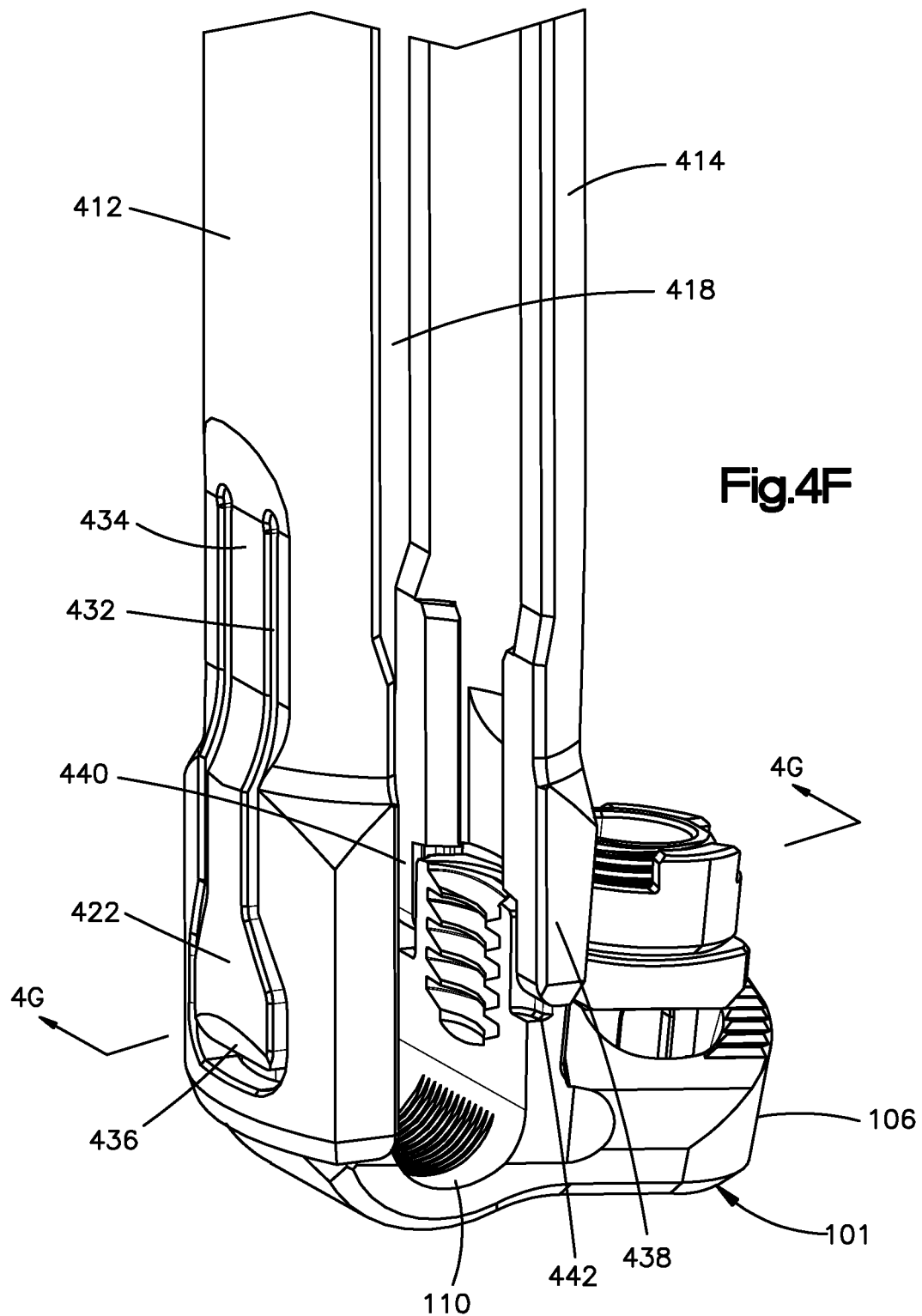
FIG. 4F is a perspective view of a distal portion of the coupler holder shown in FIG. 4A, showing the coupler holder coupled to the coupler of the bone anchor coupler assembly shown in FIG. 4A.
Figure 4G:
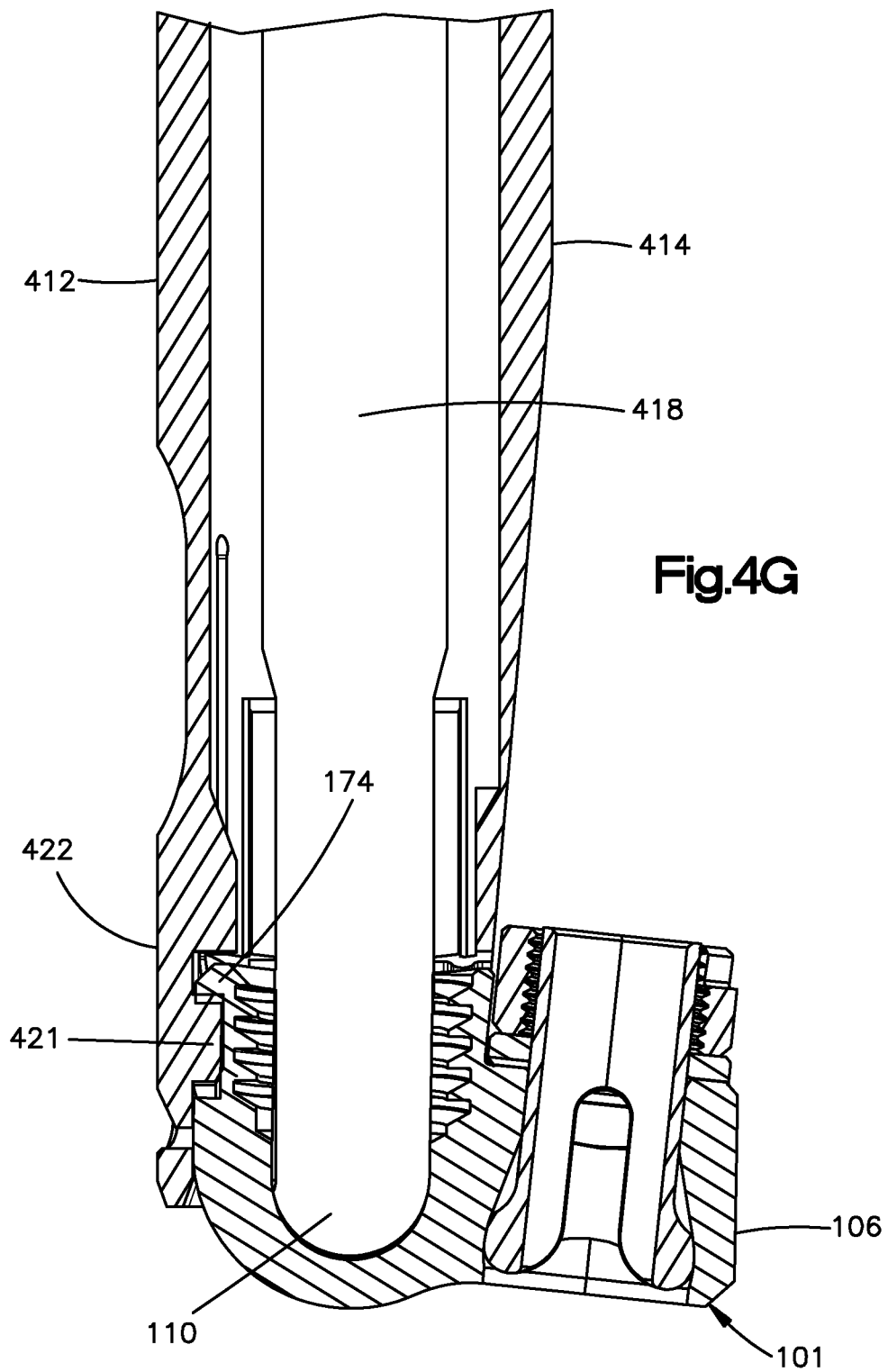
FIG. 4G is a cross-sectional view of the distal portion of the coupler holder coupled to the coupler as shown in FIG. 4F, taken along section line 4G-4G of FIG. 4F.
Figure 4J:
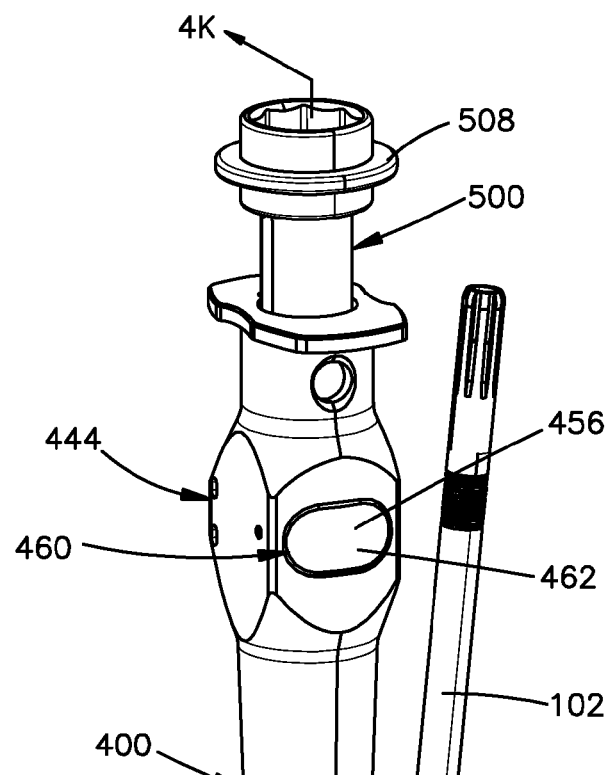
FIG. 4J is a perspective view of the coupler holder coupled to the bone anchor coupler assembly, and the fastener guide coupled to coupler holder.
Figure 4J:
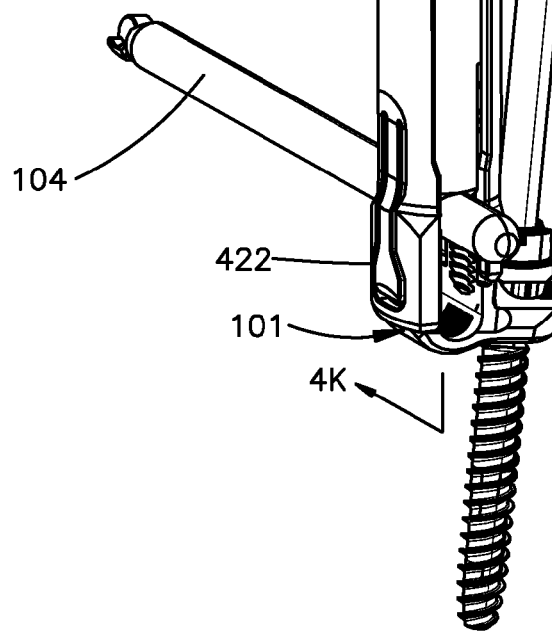

With reference to FIGS. 4A-B, each of the bone anchors 102 can include a shaft portion 95 and an anchor portion 93. The shaft portion 95 can be manipulated by a user to move the bone anchor 102. The anchor portion 93 can include external threads 123, and can be configured to be inserted into bone to attach the bone anchor 102 to the bone such as a vertebra. The bone anchor 102 can define a bore 125 that is configured and sized to receive a guidewire. The bore 125 can extend be elongate along the entire length of the bone anchor 102. The bone anchor 102 can be partly or wholly made of a Titanium-6% Aluminium-7% Niobium alloy (TAN), commercially pure titanium or any other substantially rigid material that is suitable for a bone anchor. As discussed above, at least one of the bone anchors 102 can be configured as a Schanz screw 103. In the depicted embodiment, each Schanz bone screw 103 defines a first screw end 97 and an opposed second screw end 99. The first screw end 97 may be spaced from the second screw end 99 along a longitudinal direction 88. The Schanz screw 103 may define an outer screw surface 83 and an opposed inner screw surface 81 (FIGS. 2B-C). The inner screw surface 81 may define the bore 125 that extends through the Schanz screw 103 along the longitudinal direction 88. Thus, the bore 125 may be elongate along the longitudinal direction 88. The outer screw surface 83 may define a cross-sectional dimension 85, such as a diameter, along a transverse direction 86. The transverse direction 86 may substantially perpendicular to the longitudinal direction 88. The cross-section dimension 85 may range between about 3.0 millimeters and about 8.0 millimeters. For example, the cross-sectional dimension 85 may be about 3.0 millimeters, about 3.5 millimeters, about 4.0 millimeters, about 4.5 millimeters, about 5.0 millimeters, about 5.5 millimeters, about 6.0 millimeters, millimeters 6.5 millimeters, about 7.0 millimeters, about 7.5 millimeters, or about 8.0 millimeters. At least one of the Schanz bone screws 103 may define a screw length S1 that extends from the first screw end 97 to the second screw end 99 along the longitudinal direction 88. The screw length S1 may ranges between about 30 millimeters and about 260 millimeters. For example, the screw length S1 may be about 30 millimeters, about 35 millimeters, about 40 millimeters, about 45 millimeters, about 50 millimeters, about 55 millimeters, about 60 millimeters, about 65 millimeters, about 70 millimeters, about 75 millimeters, about 80 millimeters, about 85 millimeters, about 90 millimeters, about 95 millimeters, or about 100 millimeters. The screw length S1 may also be about 105 millimeters, about 110 millimeters, about 115 millimeters, about 120 millimeters, about 125 millimeters, about 130 millimeters, about 135 millimeters, about 140 millimeters, about 145 millimeters, or about 150 millimeters. Moreover, the screw length S1 may be about 155 millimeters, about 160 millimeters, about 165 millimeters, about 170 millimeters, about 175 millimeters, about 180 millimeters, about 185 millimeters, about 190 millimeters, about 195 millimeters, or about 200 millimeters. Further, the screw length S2 may be about 205 millimeters, about 210 millimeters, about 215 millimeters, about 220 millimeters, about 225 millimeters, about 230 millimeters, about 235 millimeters, about 240 millimeters, about 245 millimeters, about 250 millimeters, about 255 millimeters, or about 260 millimeters. The anchor portion 93 may include the external threads 123 that are disposed on the outer screw surface 83. The external threads 123 may extend between a first thread end 74 and a second thread end 76 that is spaced from the first thread end along the longitudinal direction 88. The second thread end 76 and the second screw end 99 may be coexistent. In other words, the location of the second thread end 76 may be the same as the location of the second screw end 99. The anchor portion 93 defines a thread length S2 that extends from the first thread end 74 to the second thread end 76. The thread length S2 may range between about 20 millimeters and about 100 millimeters. For example, the thread length S2 may be about 30 millimeters, about 35 millimeters, about 40 millimeters, about 45 millimeters, about 50 millimeters, about 55 millimeters, or about 60 millimeters. The specific dimensions of screw length S1, the thread length S2, and the cross-sectional dimension 85 described above define the dimensions of a Schanz bone screw that allows a user to manipulate a vertebra externally (i.e., from outside of the patient's body) while at least part of the anchor portion 93 is attached to that vertebra. In addition, the Schanz bone screw 103 does not terminate in a head as conventional bone screws, such as a known polyaxial bone screw terminating in a spherical head portion. In the depicted embodiment, the Schanz bone screw 103 does not terminate in a head section, but rather includes a long shaft portion 95 that is configured to extend beyond the patient's body so that it allows a user to manipulate the Schanz screw externally (i.e., outside the patient's body). The coupler 106 can be configured to be coupled to the bone screw 102 such that the coupler 106 can be coupled at more than one position along the screw length S1 of the bone screw 102 during surgery.

Figure 2D:
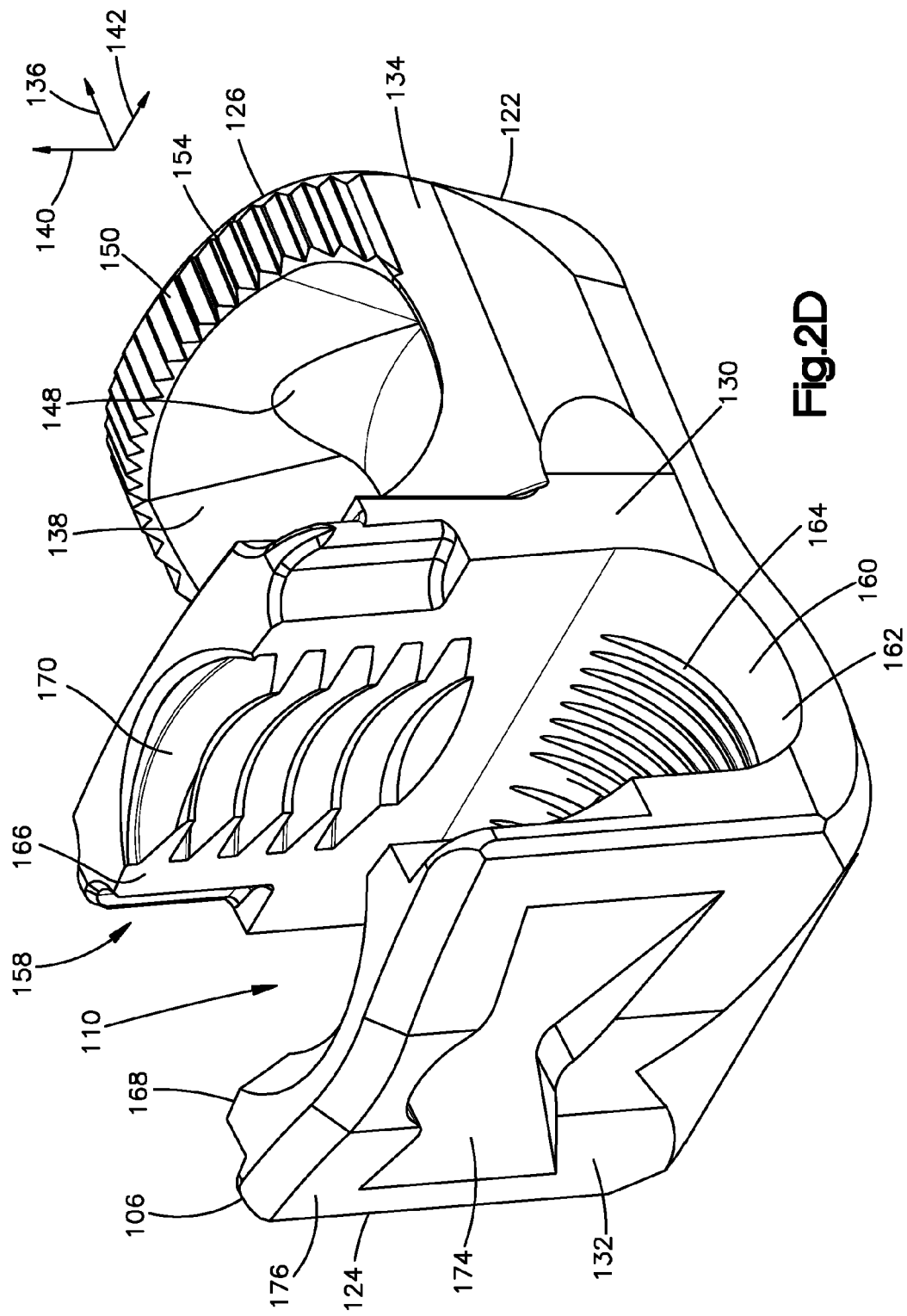
FIG. 2D is a right perspective view of the coupler shown in FIG. 2A.

With reference again to FIGS. 2A-D, the coupler 106 includes a coupler body 122 that defines the first coupler opening and the second coupler opening 110. The coupler body 122 can include a first coupler sidewall 124 and a second coupler sidewall 126 that is spaced from the first coupler sidewall 124. Additionally, the coupler body 122 can include an intermediate coupler wall 130 disposed between the first coupler sidewall 124 and the second coupler sidewall 126. The intermediate coupler wall 130 can separate the first coupler opening 108 from the second coupler opening 110. The first coupler sidewall 124, the intermediate coupler wall 130, and the second coupler sidewall 126 are spaced from one another along the lateral direction 136 (FIG. 2D).

With continuing reference to FIGS. 2A-D, the intermediate coupler wall 130 divides the coupler body 122 into a first coupler section 134 and a second coupler section 132. Thus, the coupler body 122 includes a first coupler section 134 and a second coupler section 132 that is spaced from along a lateral direction 136. The first coupler section 134 defines a first inner surface 138 that in turn defines the first coupler opening 108. The first coupler opening 108 can be configured as a hole and can extend through the coupler body 122 along a transverse direction 140. The transverse direction 140 is substantially perpendicular to the lateral direction 136. The first coupler opening 108 can be elongate along the transverse direction 140 and may have a substantially frusto-conical shape. Moreover, the first coupler opening 108 can be configured and sized to receive at least one bone anchor 102 and the collet 144 as discussed in detail below. The first inner surface 138 can completely enclose the first coupler opening 108 along the lateral direction 136 and a longitudinal direction 142 such that the bone anchor 102 can be inserted into the first coupler opening 108 along the transverse direction 140. The longitudinal direction 142 may be substantially perpendicular to the transverse direction 140 and the longitudinal direction 142. The first coupler section 134 further defines one or more indentations 148 that extend into the first inner surface 138. The indentations 148 can be disposed on opposite sides of the first inner surface 138 such that the cross-sectional dimension D of the first coupler opening 108 decreases in the transverse direction 140. In operation, the indentations 148 are configured to abut portions of the collet 144. As discussed in detail below, movement of the collet 144 within the first coupler opening 108 along the transverse direction 140 causes portions of the collet 144 to frictionally engage the first inner surface 138 so as to lock the collet 144 relative to the coupler 106, thereby fixing the bone anchor 102 with respect to the coupler 106.

With continuing reference to FIG. 2A-D, the first coupler section 134 further defines a first top body surface 150 and a second top body surface 152. The first top body surface 150 can be part of the second coupler sidewall 126, and can be substantially arc-shaped. The first coupler section 134 can further include coupler teeth 154 that protrude from the coupler body 122 along the first top body surface 150. The coupler teeth 154 are spaced from each substantially along the longitudinal direction 142 along the arc-shaped first top body surface 150. The second top body surface 152 is spaced from the first top body surface 150 along the lateral direction 136, and can be part of the intermediate coupler wall 130. Further, the second top surface 152 can also be substantially arc-shaped.

With continuing reference to FIG. 2A-D, the second coupler section 132 defines a second inner surface 156 that defines in turn defines the second coupler opening 110. The second coupler opening 110 can extend through the coupler body 122 along the longitudinal direction 118. Further, the second coupler opening 110 defines a top open end 158 and an opposed closed bottom end 160 that is spaced from the top open end 158 along the transverse direction 140. The second inner surface 156 includes a bottom surface portion 162 that defines the closed bottom end 160 of the second coupler opening 110. The top open end 158 permits posterior insertion of the spine stabilization member 104 into the second coupler opening 110. The second coupler opening 110 further defines a front open end 159 and a rear open end 161 that is spaced from the front open end along the longitudinal direction 142. The front and rear open ends 159, 161 of the second coupler opening 110 allow the coupler body 122 to move along the spine stabilization member 104 along the longitudinal direction 142 when the spine stabilization member 104 is disposed in the second coupler opening 110. The second coupler section 132 can further include ridges 164 extend into the bottom surface portion 162. The ridges 164 are spaced apart from one another along the longitudinal direction 142, and are configured to increase the friction between the spine stabilization member 104 and the second inner surface 156 so as to help retain the spine stabilization member 104 in second coupler opening 110. The second inner surface 156 further includes a first side portion 166 and a second side portion 168 that is spaced from the first side portion 166 along the lateral direction 136. Each of the first side portion 166 and the second side portion 168 defines inner threads 170 that are configured to mate with external threads 172 of the second fastener 149 in order to couple the second fastener 149 to the coupler 106. The second fastener 149 can be configured as a set screw 151, and includes the external threads 172 that are configured to mate with the inner threads 170 so as to couple the couple to second fastener 149 to the coupler 106. The second fastener 149 can be coupled to the coupler 106 so as to close to top open end 158 of the second coupler opening 110 and the spine stabilization member 104, thereby coupling the spine stabilization member 104 to the coupler 106. The second coupler section 132 further defines a recess 174 that extends into an outer surface 176 of the second coupler sidewall 126. The recess 174 is configured and sized to receive a portion of a holding instrument.

Figure 2E:
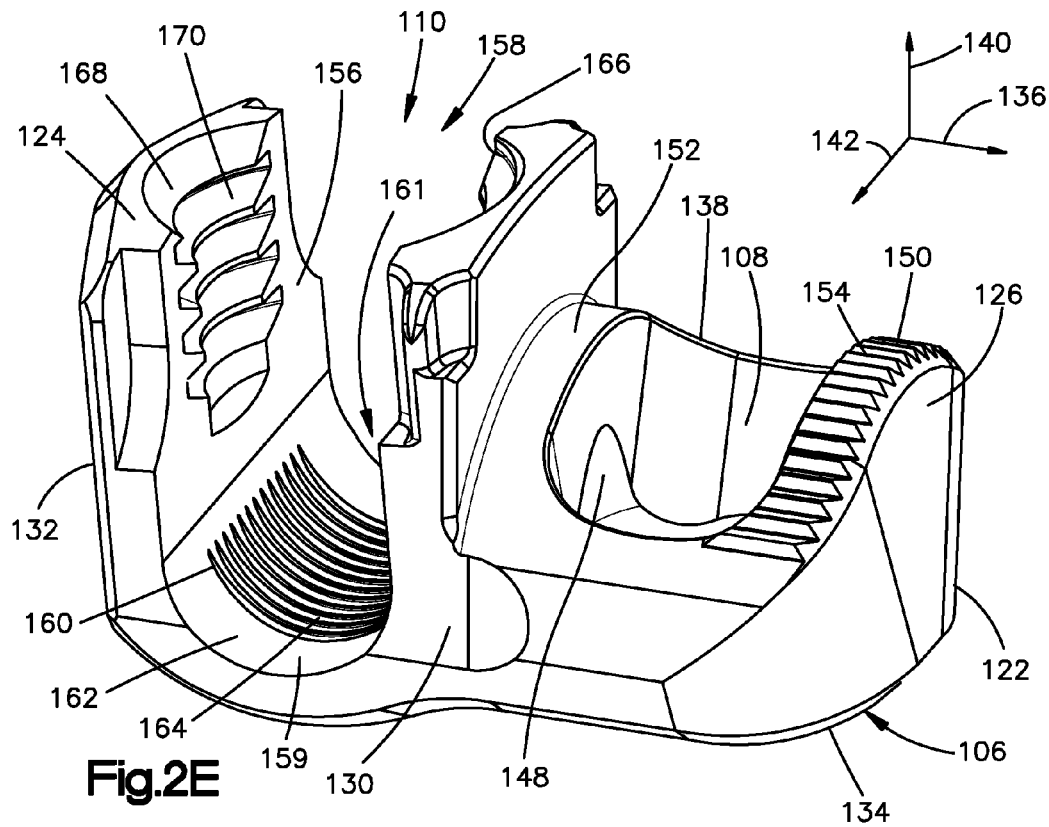
FIG. 2E is a left perspective view of the coupler shown in FIG. 2A.

With reference to FIG. 2E, the collet 144 can be configured and sized to be partially disposed in the first coupler opening 108, and includes a collet body 178. The collet body 178 can be elongate along a longitudinal direction 180 and includes a connection portion 182 and a compressible portion 184 that is spaced from the connection portion 182 along the longitudinal direction 180. The connection portion 182 includes one or more external collet threads 186 that are configured to mate with the inner threads of the first fastener 146 so as to couple the first fastener 146 to the collect 144. The collet body 178 can further define one or more substantially flat outer surfaces 188 that are configured to abut at least some substantially flat portions of the first inner surface 138 of the of the coupler body 122 in order to prevent, or at least inhibit, rotation of the collet 144 within the first coupler opening 108 when the collet 144 is at least partially disposed within the first coupler opening 108. The compressible portion 184 includes one or more resilient members 190 that are configured to move toward each other when the compressive forces C act on the compressible portion 184. The resilient members 190 can be spaced from each other along the lateral direction 192. The lateral direction 192 can be substantially perpendicular to the longitudinal direction 180. The collet body 178 can define on or more slots 194 that separate the resilient members 190 from each other. The slots 194 can be elongate along the longitudinal direction 180, and can extend through at least a portion of the collet body 178 along a transverse direction 196. The transverse direction 196 can be substantially perpendicular to the longitudinal direction 180 and the lateral direction 192. In an embodiment, the collet 144 includes two resilient members 190 separated from each other by two slots 194. The collet 144 further defines a bone anchor receiving opening 198 that extends through the collet body 178. The bone anchor receiving opening 198 can be elongate along the longitudinal direction 180, and is configured and sized to receive at least a portion of the bone anchor 102.

Figure 2F:
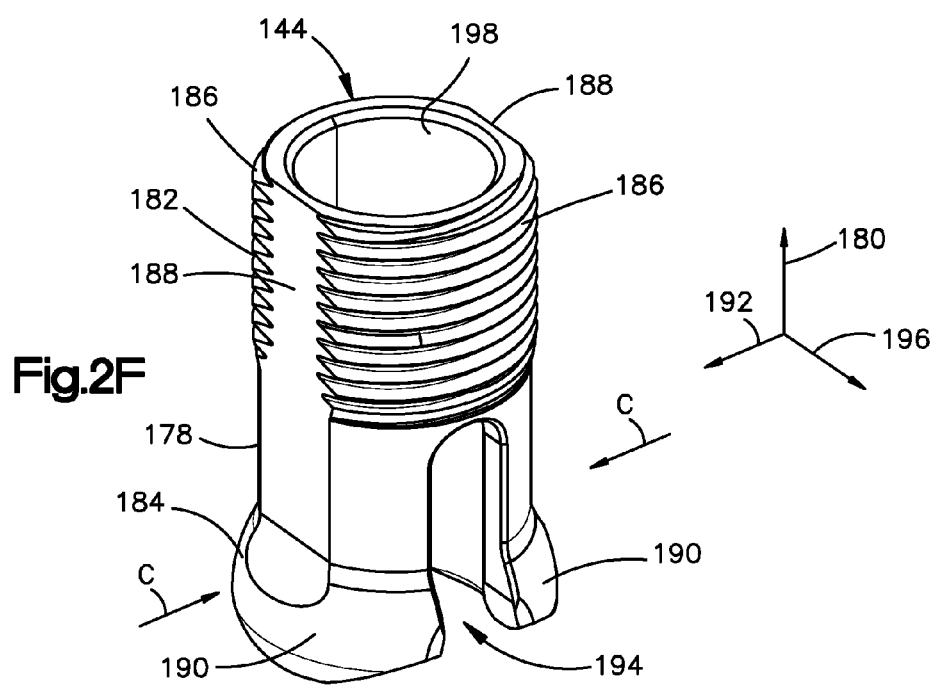
FIG. 2F is a perspective view of the collet shown in FIG. 2A.
Figure 2G:
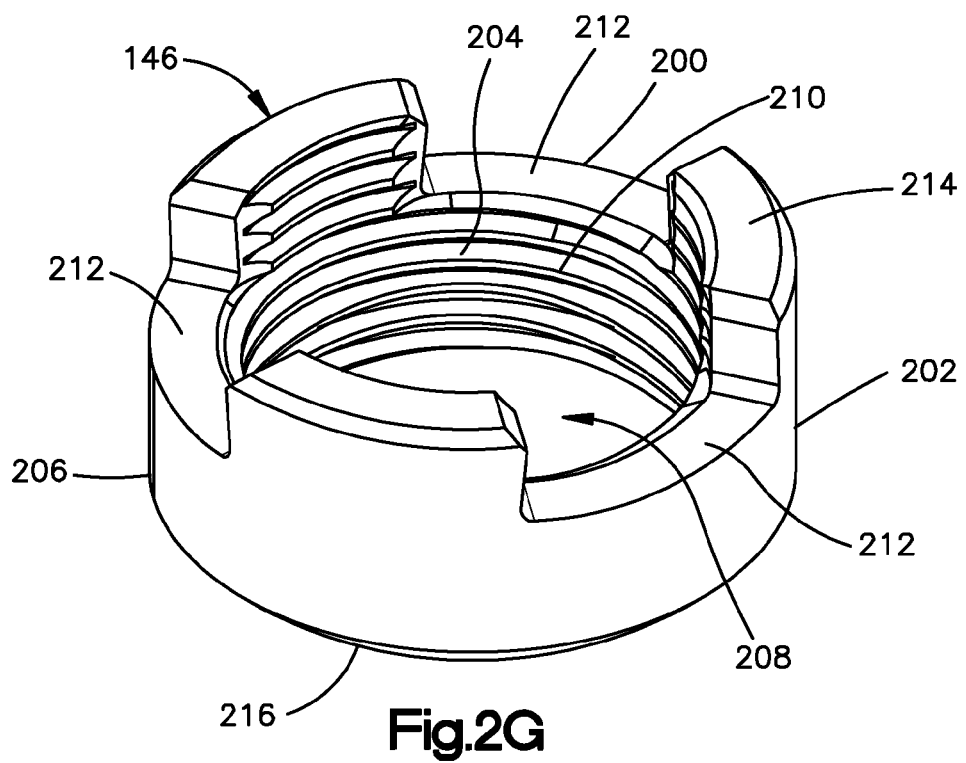
FIG. 2G is a perspective view of the first fastener shown in FIG. 2A.
Figure 2H:
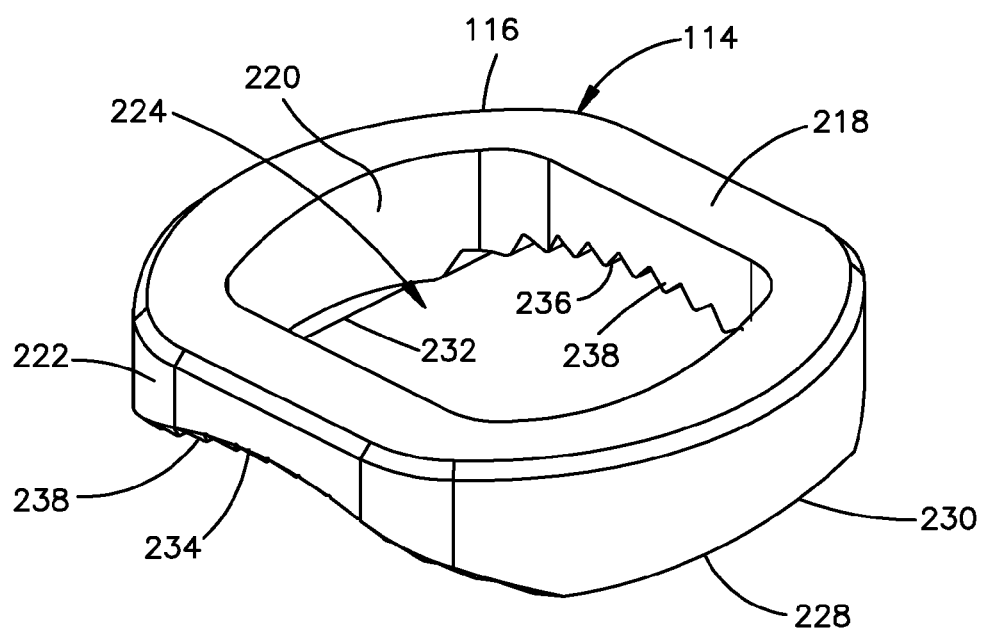
FIG. 2H is a perspective view of the pivot member shown in FIG. 2A.

With reference to FIG. 2F, the first fastener 146 can be configured to be coupled to the collet 144. In the depicted embodiment, the first fastener 146 can be configured as a nut 200, and includes a first fastener body 202. The first fastener body 202 defines an inner fastener surface 204 and an opposed outer fastener surface 206. The inner fastener surface 204 defines a collet receiving opening 208 that is configured and sized to receive at least a portion of the collet 144. The first fastener body 202 further includes inner threads 210 disposed along the inner fastener surface 204. The inner threads 210 can be configured to mate with the external collet threads 186 so as to couple the first fastener 146 to the collet 144. The first fastener body 202 further defines an upper fastener surface 214 and an opposed lower fastener surface 216. The first fastener 146 further defines one or more recesses 212 that extend into the upper fastener surface. In the depicted embodiment, the first fastener 146 includes three recesses 212 circumferentially spaced apart from one another. The recesses 212 are configured to receive portions of a drive that is configured to rotate the first fastener 146 as described below.

With continuing reference to FIG. 2A-E, in operation, rotation of the first fastener 146 in a first rotational direction R1 causes the collet 144 to move axially along a first axial direction A1 when the collet 144 is partially disposed in the first coupler opening 108 and the first fastener 146 is coupled to the collet 144. Moreover, the rotation of the first fastener 146 in a second rotation direction R2 (that is opposite the first rotational direction R1) causes the collet to move along a second axial direction A2 (that is opposite to the first axial direction A1) when the collet 144 is partially disposed in the first coupler opening 108 and the first fastener 146 is coupled to the collet 144. As the collet moves in the second axial direction A2 relative to the coupler 106, the resilient members 190 slide along the first inner surface 138. Since the cross-sectional dimension D of the first coupler opening 108 decreases in the second axial direction A2, continued movement of the collet 144 in the axial direction causes the resilient members 190 to move toward each other. Further movement of the collet 144 in the second axial direction A2 eventually causes the compressible portion 184 of the collet 144 to be compressed against the bone anchor 102 partially disposed in the bone anchor receiving opening 198, thereby fixing angular orientation and longitudinal position of the bone anchor 102 with respect to the coupler 106. In summary, the rotation of the first fastener 146 in the first rotational direction R1 causes the collet 144 to move axially between an unlocked collet position (FIG. 2C) and a locked collet position (FIG. 2B). In the unlocked collet position, the bone anchor 102 can be pivoted relative to the coupler 106. In the locked collet position, the bone anchor 102 is fixed relative to the coupler 106 and, therefore, cannot be pivoted relative to the coupler 106. As discussed above, the rotation of the first fastener 146 in the first rotational direction R1 urges the collet 144 to move from the unlocked collet position to the locked collet position. However, it is envisioned that the first fastener 146 can be configured such that the rotation of the first fastener 146 in the second rotational direction R2 causes the collet 144 to move from the unlocked position to the locked position. In the locked position, the compressible portion 184 is press-fitted in the first coupler opening 108.

With reference to FIGS. 2A-H, the pivot member 114 can be configured as a ring such as a washer 116. Further, the pivot member 114 can be configured to be disposed between the first fastener 146 and coupler 106. The pivot member 114 includes a pivot body 218 that defines an inner pivot surface 220 and an opposed outer pivot surface 222. The inner pivot surface 220 defines a collet receiving opening 224 that is configured and sized to receive at least a portion of the collet 144. The pivot body 218 further defines an upper pivot surface 226 and an opposed lower pivot surface 228. The upper pivot surface 226 can have a substantially planar configuration and is configured to abut lower fastener surface 216 when the collet 144 is coupled to the first fastener 146 and the pivot member 114 is disposed between the first fastener 146 and the coupler 106. At least a portion of the lower pivot surface 228 is contoured to receive the first and second top body surfaces 150, 152. The lower pivot surface 228 includes a front portion 230, a rear portion 232, a first lateral portion 236, and a second lateral portion 234. The first lateral portion 236 of the lower pivot surface 228 can be contoured to receive the first top body surface 150 of the first coupler section 134 so as to allow the pivot member 114 to pivot relative to the coupler 106 about a pivot axis 240. For instance, the first lateral portion 236 of the lower pivot surface 228 can have a substantially concave shape that substantially corresponds to the substantially arc shape of the first top body surface 150 of the first coupler section 134. The second lateral portion 234 of the lower pivot surface 228 can be contoured to receive the second top body surface 152 of the first coupler section 134 so as to allow the pivot member 114 to pivot relative to the coupler 106 the pivot axis 240. For example, the lateral portion 234 of the lower pivot surface 228 can have a substantially concave shape that corresponds to the arc shape of the second top body surface 152 so as to allow the pivot member 114 to pivot about the pivot axis 240. The pivot member 114 may further include pivot teeth 238 that are configured to mate with the coupler teeth 154 of the coupler 106 such that the pivot member 114 can incrementally pivot relative to the coupler 106 about the pivot axis 240. It is envisioned that some of the pivot teeth 238 can mate with the coupler teeth 154 while other pivot teeth 238 can be pressed on the second top body surface 152 of the coupler 106 when the coupler 106 is coupled to the pivot member 114. The pivot teeth 238 protrude from the pivot body 218. In an embodiment, the pivot teeth 238 are only located along first later portion 236 or second lateral portion 234 of the lower pivot surface 228. Although the depicted embodiment illustrates the pivot member 114, any angular adjustment member 127 can be employed. Thus, the angular adjustment member 127 can be configured as the pivot member 114 or any other apparatus capable of facilitating angular adjustment of the bone anchor 102 relative to the coupler 106.

In operation, the angular orientation of the bone anchor 102 relative to the coupler 106 can be adjusted by moving the pivot member 114 with respect to the coupler 106. In particular, a user can move the bone anchor 102 so that the pivot member 114 moves along the top body surfaces 150, 152 of the coupler 106 between the initial position and the angled position. The movement of the bone anchor 102 relative to the coupler 106 in a first direction causes the pivot member 114 to pivot about the pivot axis 240 along a first pivotal direction 242 when the bone anchor is coupled to the coupler 106 via the collet 144. The movement of the bone anchor 102 relative to the coupler 106 in a second direction causes the pivot member 114 to pivot about the pivot axis 240 along a second pivotal direction 244 that is opposite the first pivotal direction 242.

The minimally invasive spinal stabilization system 100 can be employed to adjust the angulation of the vertebrae V1, V2 relative to each other and to adjust the distance between the vertebrae V1. V2 by following some or of the steps described below. The attachment locations of the bone anchors 102 is determined by using, for example, radiographic imaging. The attachment locations of the bone anchors 102 can be the pedicles of the vertebrae. Then, a cutting tool, such as an awl, can be inserted into the determined attachment locations to perforate the cortex of the vertebra and create a bone anchor channel in the vertebra. A guidewire, such as a Kirscher wire, can be inserted into the bone anchor channel. The cutting tool is then removed from the patient's body, while the guidewire remains in position. Soft tissue leading to the attachment location can then be dilated. The dilation can be performed by sequentially inserting dilators of different sizes into the patient's body. After dilation one of the bone anchors 102 can be attached in a first attachment location such as in the pedicle of a vertebra. Another bone anchor 102 can be attached in a second attachment location such as in the pedicle of another vertebra. One coupler 106 can then be coupled to one of the bone anchor 102, and another coupler 106 can be coupled to another bone anchor 102. Each coupler 106 can be coupled to a bone anchor 102 such that a portion of the bone anchor 102 is disposed in the first coupler opening 108. The spine stabilization member 104 can then be coupled to two couplers 106 such that a portion of the spine stabilization member 104 is disposed in the second coupler opening 110 of one coupler 106, and another portion of the spine stabilization member 104 is disposed in the second coupler opening 110 of another coupler 106. One second fastener 149 can be inserted in the second coupler opening 110 of each coupler 106. The second fastener 149 can be coupled to the coupler 106 as shown discussed above. Then, the bone anchors 102 can be moved angularly to correct the angular orientation of the vertebrae as discussed in detail above. Optionally, the bone anchors 102 can be moved away or toward to each other to adjust the distance between the vertebrae to which the bone anchors 102 are attached. Next, the second fasteners 149 can be tightened (as discussed above) to fix the position of the spine stabilization member 104 relative to the couplers 106. Moreover, the first fasteners 146 are moved from the unlocked position to the locked position in order to fix the position of the bone anchors 102 relative to the couplers 106. The bone anchors 102 are then trimmed such that no portion of the bone anchors 102 extends outside of the patient's body. Thus, the bone anchors 102 are cut to shorten their length. The method described above can use instruments and steps as described in U.S. Patent Application Publication No. 2011/0263945, filed on Apr. 23, 2010, U.S. Patent Application Publication No. 2010/0268279, filed on Jan. 25, 2010, and U.S. Pat. No. 5,047,029 issued on Sep. 10, 1991. Each of U.S. Patent Application Publication No. 2011/0263945, U.S. Patent Application Publication No. 2011/0263945, and U.S. Pat. No. 5,047,029 is incorporated herein by reference in its entirety.

Figure 3B:
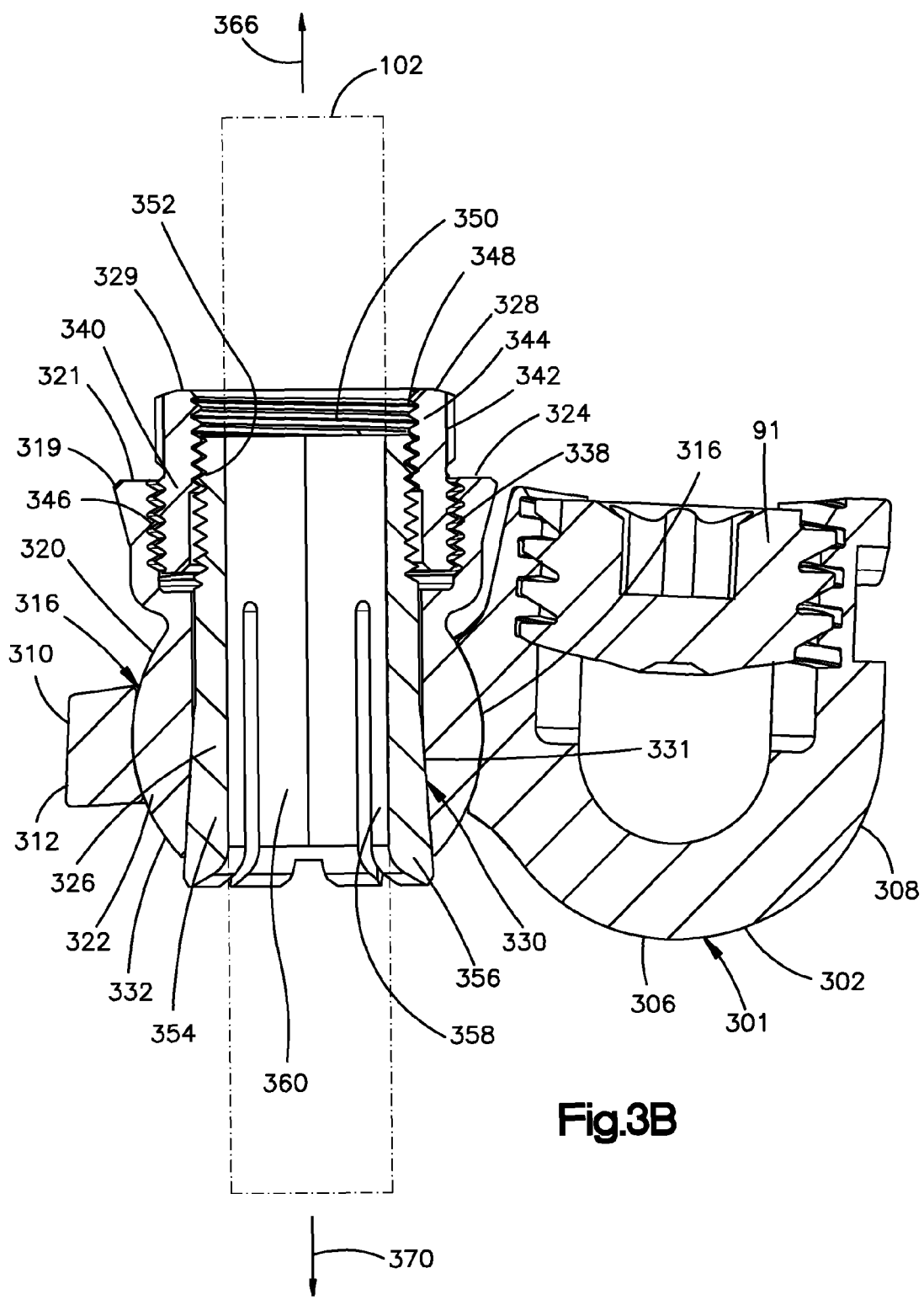
FIG. 3B is a cross-sectional view of the bone anchor coupler assembly shown in FIG. 3A, taken along section line 3B-3B, showing the collet in an unlocked position.
Figure 3C:
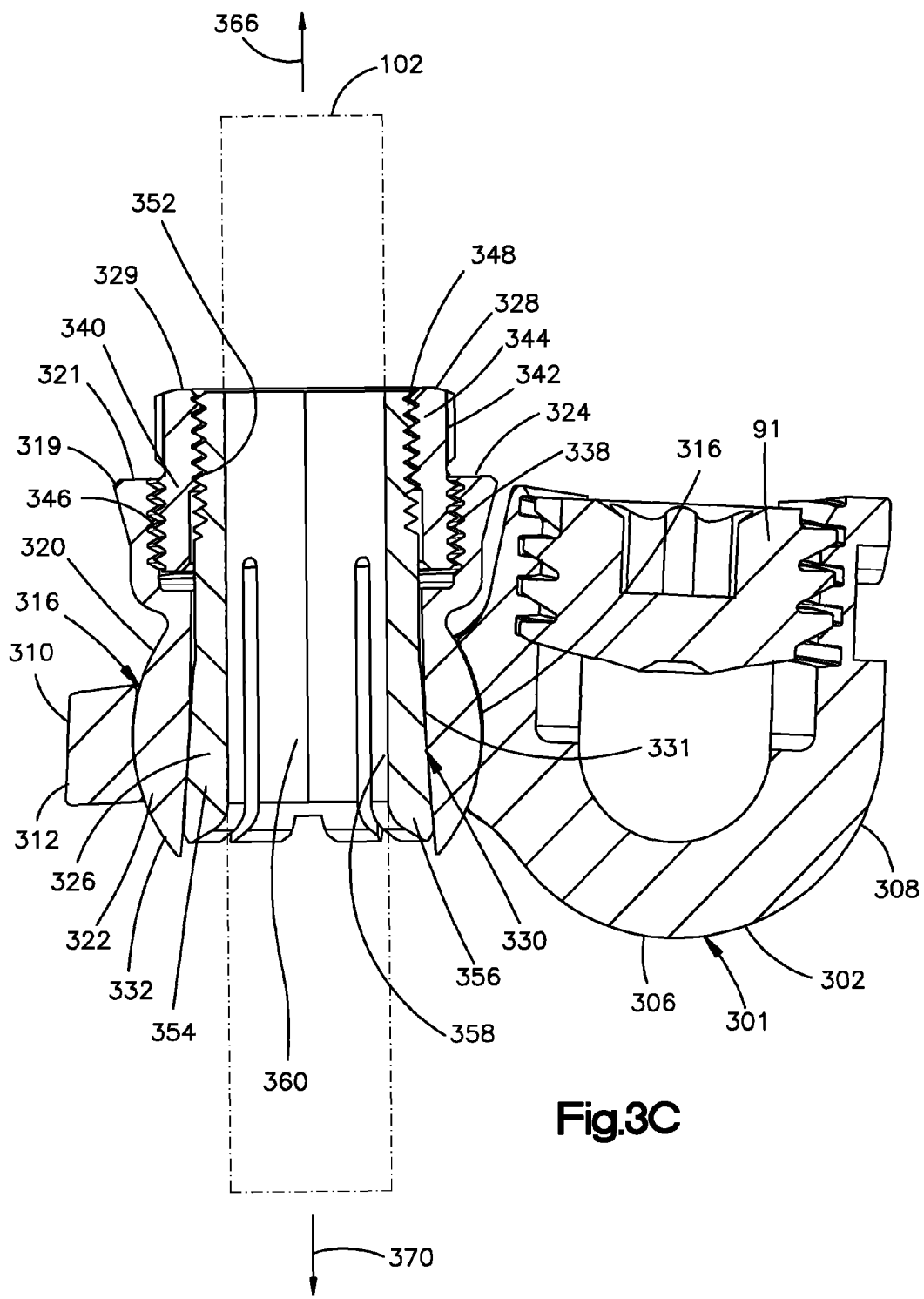
FIG. 3C is a cross-sectional view of the bone anchor coupler assembly shown in FIG. 3A, taken along section line 3B-3B, showing the collet in a locked position.

With reference to FIGS. 3A-C, another embodiment of the minimally invasive spinal stabilization system 300 includes a coupler 302 that is similar to the coupler 106. The coupler 302 includes a coupler body 306. The coupler body 306 includes a first coupler section 308 that is substantially similar or identical to the first coupler section 134 of the coupler 106. Thus, the structure and operation of the first coupler section 308 can be substantially similar or identical to the structure and operation of the first coupler section 134. For instance, the second coupler section 310 can be coupled to the second fastener 149 in order to secure the spine stabilization member 104 to the coupler body 306 as described above.

The coupler body 306 further includes a second coupler section 310 that is coupled to the first coupler section 308. The second coupler section 310 is spaced from the first coupler section 308 along a lateral direction 314. Further, the second coupler section 310 can be substantially shaped as a ring, and includes a second body 312. In addition, the coupler 306 defines an inner coupler surface 316 that in turn defines a coupler opening 316 that extends through the second body 312. The coupler opening 316 can be through the second body 312 along a transverse direction 318. The transverse direction 318 can be substantially perpendicular to the lateral direction 314. The coupler opening 316 can be configured and sized to receive a polyaxial connection member 320. Although the depicted embodiment illustrates a polyaxial connection member 320, it is envisioned that any angular adjustment member 319 can be employed. Thus, angular adjustment member 319 can be configured as the polyaxial connection member 320 or any other apparatus that can facilitate angular adjustment of the bone anchor 102 relative to the coupler 302.

The polyaxial connection member 320 can be configured as a bushing, and can include a connection body 321. The polyaxial connection member 320 further defines an inner connection surface 331 that in turn defines a connection opening 330. The connection opening 330 can extend through the connection body 321, and can be elongate along the transverse direction 318 when the polyaxial connection member 320 is received in the coupler opening 316.

The connection body 321 includes compressible connection portion 322 and a connection portion 324 that is spaced from the compressible connection portion 322 along the transverse direction 318. The compressible connection portion 322 can be compressed upon application of compressive forces as discussed above. In the depicted embodiment, the compressible connection portion 322 defines a substantially spherical outer surface 332 that substantially matches the shape of the inner coupler surface 316 in order to facilitate polyaxial angulation of the polyaxial connection member 320 relative to the coupler body 306, which in turn facilitates polyaxial angulation of the bone anchor 102 with respect to the coupler body 306 when the bone anchor 102 is coupled to the coupler 302. The compressible connection portion 322 includes a plurality of resilient members 334 such as resilient fingers that facilitate compression of the compressible connection portion 322 upon application of compressive forces. The resilient members 334 are separated from one another by a plurality of slots 336 that extend through the compressible connection portion 322.

The connection portion 324 of the polyaxial connection member 320 can be configured to interconnect a collet 326 and a fastener 328. In particular, the inner surface 331 defines inner threads 338 that are configured to mate with external threads 340 of the fastener 328 to couple the fastener 328 to the polyaxial connection member 320. The fastener 328 can be configured as a nut 329, and further includes a fastener body 342 that defines an inner fastener surface 344 and an opposed outer fastener surface 346. The external threads 340 are disposed on the outer fastener surface 346. The inner fastener surface 433 defines a fastener opening 348 that is configured to receive the collet 326. Moreover, the fastener 328 can include inner fastener threads 350 that are configured to mate with an external collet threads 352 of the collet 326. In operation, rotation of the fastener 328 causes the collet 326 to move axially along between a locked position (FIG. 3C) and an unlocked position (FIG. 3B) as discussed in detail below. The coupler 302, the collet 326, the first fastener 328, the second fastener 149, and the polyaxial connection member 320 collectively form a bone anchor coupler assembly 301. The bone anchor coupler assembly 301 can also referred to as the bone anchor clamp assembly. The bone anchor coupler assembly 301 can be configured to couple the spine stabilization member 104 to the bone anchor 102. Further, the bone anchor coupler assembly 301 can be part of the minimally invasive spinal stabilization system 300. The bone anchor coupler assembly 301 may be partly or entirely constructed from any biocompatible material known in the art including, but not limited to, stainless steel, titanium, titanium alloys, polymers, etc.

The collet 326 includes the external collet threads 352 that are configured to include inner fastener threads 350, and a compressible collet portion 354 that includes a plurality of resilient members 356 such as fingers. The resilient members 356 are separated from one another by a plurality of slots 358. The resilient members 356 facilitate compression of the compressible collet portion 354 when the compressible collet portion 354 is subjected to compressive forces. The resilient members 356 are biased away from the collet opening 360. The collet 326 further defines a collet opening 360 that is configured and sized to receive a portion of the bone anchor 102.

In operation, the collet 326 is configured to move axially between an unlocked position (FIG. 3B) and a locked position (FIG. 3C) in order to lock the position of the bone anchor 102 with respect to the coupler body 306 when the bone anchor is partially disposed within the collet opening 360. Specifically, the rotation of the fastener 328 about a rotation axis 362 in a first rotational direction 364 causes the collet 326 to move axially in a first axial direction 366, thereby moving the collet from the unlocked position to the locked position. In the unlocked position, the resilient members 356 are at least partially located outside of the polyaxial connection member 320, and, and therefore, facilitate polyaxial angulation of the polyaxial connection member 320 relative to the coupler body 306. In the locked position, the resilient members 356 are pressed against the inner surface 331, which in turn causes the compressible connection portion 322 to engage the inner coupler surface 316 such that the position of the polyaxial connection member 320 is fixed relative to the coupler body 306, thereby fixing the position of the bone anchor 102 relative to the coupler body 306 when the bone anchor 102 is partially disposed in the collet opening 360. The rotation of the fastener 328 about the rotation axis 362 in a second rotational direction 368 (which is opposite the first rotational direction 366) causes the collet 326 to move in a second axial direction 370 (which is opposite the first axial direction 366) to move the collet from the locked position to the unlocked position. It is envisioned, however, that rotational direction and the axial direction described above may vary.

With reference to FIGS. 4A-B, a coupler holder 400 is configured to hold the bone anchor coupler assembly 101. Specifically, the coupler holder 400 can hold the coupler 106. In operation, the coupler holder can be used to couple the bone anchor coupler assembly 101 to a bone anchor 102 attached to a vertebra V of the spine S. In particular, the coupler holder 400 is first coupled to the bone anchor coupler assembly 101. Then, the coupler holder 400 can be advanced toward the bone anchor 102 such that the bone anchor 102 is disposed in the first coupler opening 108 (FIG. 2B) of the coupler 106. Next, the coupler holder 400 can be advanced toward the vertebra V so that the coupler 106 slides along the bone anchor 102 until the coupler 106 is positioned adjacent the vertebra V. The bone anchor 102 is generally constructed of titanium or a titanium alloy, such as an alloy including Titanium, Aluminum and Niobium (TAN—TI-6Al-6Nb—ASTM F 1295) but may also be constructed of stainless steel, other metallic alloy materials or nearly any strong, stiff, biocompatible material.

With reference to FIGS. 4C-G, the coupler holder 400 includes a holder body 402 that is elongate along longitudinal direction 404. The holder body 402 includes a first holder end 406 and a second holder end 408 that is spaced from the first holder end 406 along the longitudinal direction 404. The coupler holder 400 defines a first holder opening 410 that extends through the holder body 402 along the longitudinal direction 404. The first holder opening 410 can be configured as a bore. In addition to the first holder opening 410, the coupler holder 400 further includes a first holder prong 412 and a second holder prong 414 that is spaced from the first holder prong 412 along a lateral direction 416. The lateral direction 416 can be substantially perpendicular to the longitudinal direction 404. Each of the first holder prong 412 and the second holder prong 414 protrudes from the holder body 402 along the longitudinal direction 404. Further, the first holder prong 412 and the second holder prong 414 can each be elongate along the longitudinal direction 404. The first holder prong 412 includes a first prong body 413 that defines a first or proximal end 424 that is attached to the holder body 402, and a second or distal free end 426 that is spaced from the first end 424 along the longitudinal direction 404. The second holder prong 414 includes a second prong body 415 that defines a first or proximal end 428 that is attached to the holder body 402, and a second or free distal end 430 that is spaced from the first end 428 along the longitudinal direction 404.

The coupler holder 400 defines a second holder opening 418 between the first holder prong 412 and the second holder prong 414. The second holder opening 418 can be in communication with the first holder opening 410, and can extend through the coupler holder 400 along a transverse direction 420. The transverse direction 420 can be substantially perpendicular to the longitudinal direction 404 and the lateral direction 416. Further, the second holder opening 418 can be configured as a slot, and can be elongate along the longitudinal direction 404. Regardless of its configuration, the second holder opening 418 is configured and sized to receive at least a portion of the spine stabilization member 104. The second holder opening 418 may define a substantially U-shape. In operation, when the coupler holder 400 is coupled to the bone anchor coupler assembly 101, the second holder opening 418 can provide guidance to the spine stabilization member 104 to the second coupler opening 110 (FIG. 4F) of the coupler 106.

With reference to FIGS. 4C-G, the coupler holder 400 includes a holder resilient member 422 in at least one of the first holder prong 412 or the second holder prong 414. In the depicted embodiment, the holder resilient member 422 is configured as a resilient arm, and is movably coupled to the first holder prong 412 adjacent the second end 430. Specifically, the holder resilient member 422 can be movably coupled to the first prong body 413. The holder resilient member 422 can be defined by a slot 432 disposed in the first prong body 413, and includes a first deflectable end 434 movably coupled to the first holder prong 412, and a second free end 436 that is spaced from the first deflectable end 434 along a longitudinal direction 404. The first deflectable end 434 is configured to deflect relative to the first prong body 413 so that the holder resilient member 422 can flex relative to the first holder prong 412. Alternatively, the holder resilient member 422 can be movably coupled to the first holder prong 412 by a spring-biased hinge or any mechanism that allows the holder resilient member 422 to flex or pivot with respect to the first holder prong 412. At least a portion of the second free end 436 is configured to be received in the recess 174 (FIG. 2D) of the coupler 106 so as to couple the coupler holder 400 to the coupler 106. For example, holder resilient member 422 may include at least one protrusion 421 (FIG. 4G) that protrudes from the second free end 436. The protrusions 421 can be configured and sized to be received in the recess 174 so as to couple the coupler holder 400 to the coupler 106.

The second holder prong 414 can include a first tine 438 and a second tine 440 that is spaced from the first tine 438 along the lateral direction 416. Thus, the first tine 438 and the second tine 440 protrude from the second prong body 415 along the longitudinal direction 404. The second holder prong 414 defines a space 442 between the first tine 438 and the second tine 440. The space 442 is configured and sized to receive at least a portion of the intermediate coupler wall 130 of the coupler 106 so as to couple the second holder prong 414 to the coupler 106.

With continuing reference to FIGS. 4C-K, the holder body 402 further includes a hollow housing 444 disposed between the first holder end 406 and the second holder end 408. The housing 444 is configured to support at least a portion of a ratchet mechanism 446. The ratchet mechanism 446 includes a ratchet body 448 that is configured to move within the housing 444 along the transverse direction 420 between a locked position and an unlocked position as described in detail below. The ratchet mechanism 446 defines a ratchet opening 450 that extends through the ratchet body 448 along the longitudinal direction 404. The ratchet opening 450 can be configured as a hole or a bore. The ratchet body 448 defines an inner surface 452 that in turn defines the ratchet opening 450. In addition, the ratchet body 448 defines an outer surface 454 opposite the inner surface 452. In the depicted embodiment, the ratchet body 448 includes a front wall 456 and an opposed rear wall 458 that is spaced from the front wall along the transverse direction 420. The housing 444 defines a housing opening 460 that is configured and sized to receive at least a portion of the front wall 456. The front wall 456 defines a ratchet button 462 that is accessible via the housing opening 460. In operation, a user can move ratchet mechanism 446 pressed the ratchet button 462 in the transverse direction 420 to move the ratchet mechanism 446 between the locked position and the unlocked position. In the depicted embodiment, the application of a force to the ratchet button 462 in the transverse direction causes the ratchet mechanism 446 to move from the locked position to the unlocked position as discussed in detail below. The rear wall 458 of the ratchet body 448 can be coupled to an inner portion of the housing 444 via one or more biasing members 464. In the depicted embodiment, two biasing members 464 are connected between an inner portion of the housing 444 and the rear wall 458. The biasing members 464 can be configured as suitable springs, such as coil springs, that are capable of biasing the ratchet body 448 in a biasing direction 468 that is opposite to the transverse direction 420. Thus, the ratchet body 448 is biased in the biasing direction 468, causing the ratchet mechanism 446 to be biased toward locked position. The ratchet body 448 further includes first sidewall 466 and an opposed second sidewall 470 that is spaced from the first sidewall 466 along the lateral direction. The ratchet body 448 is movably coupled to the housing 444 via the first sidewall 466 and the second sidewall 470. In particular, the coupler holder 400 includes one or more fasteners, such as pins 472, connected between the housing 444 and the first sidewall 466 and the second sidewall 470 of the ratchet body 448. The ratchet body 448 defines one or more recesses 474 that are each configured and sized to receive one or more pins 472. The recesses 474 can extend into the outer surface 454 of the ratchet body 448. In the depicted embodiment, one recess 474 is disposed in the first sidewall 466, and another recess 474 is disposed in the second sidewall 470. Each recess 474 can be elongate along the transverse direction 420, thereby guiding the movement of the ratchet body 448 along the transverse direction 420 when the pins 472 are disposed in the recesses 474.

The ratchet mechanism 446 further includes a holder rack 476 defined along the inner surface 452 of the ratchet body 448. Specifically, the holder rack 476 can be disposed along the along an inner portion of the rear wall 458 of the ratchet body 448. The holder rack 476 defines a plurality of holder teeth 478. The holder teeth 478 are spaced from one another along the longitudinal direction 404. In operation, movement of the ratchet body 448 along the transverse direction 420 between the locked position and the unlocked position causes the holder rack 476 to move along the transverse direction 420 between a locked position and an unlocked position.

With continuing reference to FIGS. 4C-K, the minimally invasive spinal stabilization system 100 may further include a fastener guide 500 that is configured to guide the second fastener 149 along the coupler holder 400 and toward the second coupler opening 110 in order to lock the spine stabilization member 104 in the second coupler opening 110. The fastener guide 500 includes a guide body 502 that is configured to be received in the first holder opening 410 and the second holder opening 418 of the coupler holder 400. The guide body 502 can be elongate along a longitudinal direction 506, and defines a first or proximal guide end 508 and a second or distal guide end 510. The second guide end 510 is spaced from the first guide end along the longitudinal direction 506. The fastener guide 500 defines a guide opening 504 (FIG. 4K) that extends through the guide body 502. The guide opening 504 can be elongate along the longitudinal direction 506, and is configured to receive a driver that is configured to drive the second fastener 149 into the second coupler opening 110.

Figure 4K:
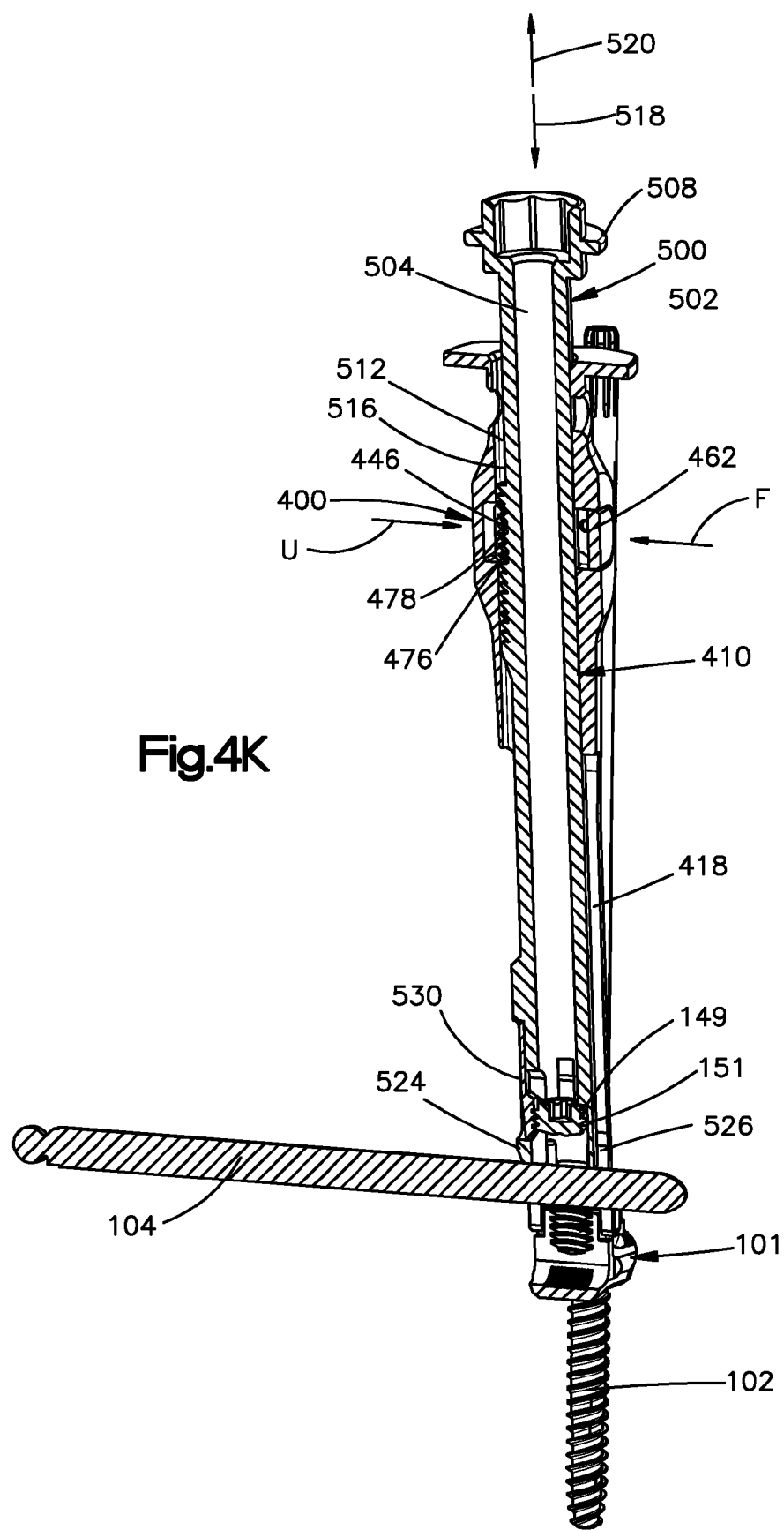
FIG. 4K is a sectional view of the coupler holder coupled to the bone anchor coupler assembly, and the fastener guide coupled to coupler holder, taken along section line 4K-4K of FIG. 4J.
Figure 4L:
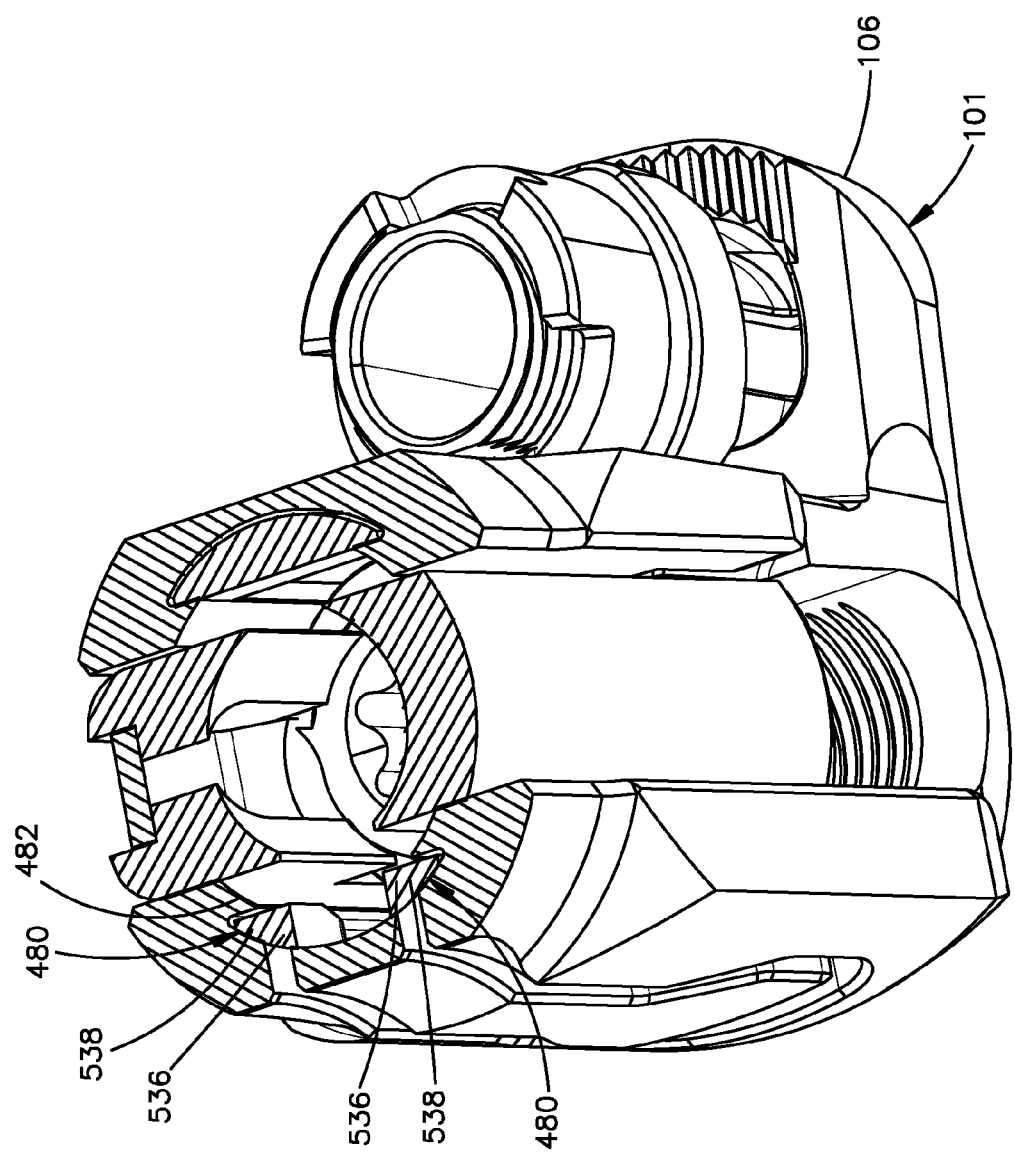
FIG. 4L is a sectional perspective view of the coupler holder coupled to the bone anchor coupler assembly, and the fastener guide coupled to coupler holder.

The fastener guide 500 further includes a guide rack 512 that is disposed between the first guide end 508 and the second guide end 510. The guide rack 512 protrudes from the guide body 502 in a transverse direction 514. The transverse direction 514 is substantially perpendicular to the longitudinal direction 506. The guide rack 512 is configured to mate with the holder rack 476 such that the fastener guide 500 can be moved relative to the coupler holder 400 in an incremental manner when the fastener guide 500 is at least partially disposed in the first holder opening 410. In the depicted embodiment, the guide rack 512 includes a plurality of guide teeth 516 that protrude from the guide body 502 in the transverse direction 514. The guide teeth 516 are spaced apart from one another along the longitudinal direction 506, and are configured to mate with the holder teeth 478 so that the fastener guide 500 can be incrementally advanced through the first holder opening 410 of the coupler holder 400. The guide teeth 516 and the holder teeth 478 are oriented relative to each other so that the engagement of the guide rack 512 with the holder rack 476 allows the incremental movement of the fastener guide 500 relative to the coupler holder 400 in a first direction 518 but prevents, or at least hinders, movement of the fastener relative to the coupler holder 400 in a second direction 520, which is opposite to the first direction 518 when the ratchet mechanism 446 is in the locked position as shown in FIG. 4K.

In operation, when the ratchet mechanism 446 is in the locked position and the fastener guide 500 is at least partially disposed in the first holder opening 410, the guide teeth 516 can mate with the holder teeth 478, thereby allowing incremental movement of the fastener guide 500 relative to the coupler holder 400 in the first direction 518, while precluding, or at least inhibiting, movement of the fastener guide 500 relative to the coupler holder 400 in the second direction 520. However, the ratchet mechanism 446 can be moved from the locked position to the unlocked position to allow the fastener guide 500 to move relative to the coupler holder 400 in the second direction 520. To do so, a force is applied to the ratchet button 462 in the direction F in order to move the holder teeth 478 away from the guide teeth 516, thereby disengaging the holder rack 476 from guide rack 512. To apply the force to the ratchet button 462, a user may simply press the ratchet button 462 in the direction F. Releasing the ratchet button 462 causes the biasing members 464 (FIG. 4E) to urge the holder teeth 478 toward the guide teeth 516 in the direction U, which is opposite to the direction F, causing the ratchet mechanism 446 to move to the locked position. As discussed above, when the ratchet mechanism 446 is in the locked position, the holder rack 476 can mate with the guide rack 512 to prevent, or at least hinder, the fastener guide 500 from moving relative to the coupler holder 400 in the second direction 520. The ratchet mechanism 446 allows the user to precisely control the movement of the fastener guide 500 with respect to the coupler holder 400.

With continuing reference to FIGS. 4C-K, the fastener guide 500 may include holding section 522 that is configured to hold the second fastener 149. As discussed above, the second fastener 149 is also referred to as the locking cap, and can be configured as a set screw 151. The holding section 522 may include one or more guide prongs that are configured to hold the second fastener 149. In the depicted embodiment, the holding section 522 includes a first guide prong 524 and a second guide prong 526 that is spaced from the first guide prong 524 along the transverse direction 514. Each of the first guide prong 524 and the second guide prong 526 protrude from the guide body 502 in the longitudinal direction 506. The holding section 522 defines a fastener receiving space 528 between the first guide prong 524 and the second guide prong 526. The fastener receiving space 528 is configured and sized to receive the second fastener 149 as shown in FIG. 4I.

The holder section 522 may further include a guide resilient member 530 that is movably coupled to the at least one of the first guide prong 524 or the second guide prong 526. In the depicted embodiment, the guide resilient member 530 is movably coupled to the first guide prong 524, and can be configured as a resilient arm. The resilient member 530 defines a first end 532 movably coupled to the first guide prong 524, and a second free end 534 that can flex relative to the first guide prong 524. The second free end 534 is biased toward the fastener receiving space 528 such that the second free end 534 of the guide resilient member 530 can contact the second fastener 149 that is positioned in the fastener receiving space 528, thereby coupling the second fastener 149 to the fastener guide 500. Alternatively, the guide resilient member 530 can be movably coupled to the first guide prong 524 by a spring-biased hinge or any mechanism that allows the guide resilient member 530 to flex or pivot with respect to the first guide prong 524.

The fastener guide 500 can further include one or more protrusions 536, such as teeth 538, that protrude from the guide body 502 in the longitudinal direction 506. The protrusions 536 are configured and sized to be received in channels 480 defined by at least one of the first holder prong 412 or the second holder prong 414 of the coupler holder 400. In the depicted embodiment, the channels 480 are defined along an inner surface 482 of the first holder prong 412. The protrusions 536 can be inserted in the channels 480 as an anti-splay feature. That is, the protrusions 536 can be inserted in the channels 480 to prevent, or at least minimize, transverse or lateral movement of the first coupler sidewall 124 relative to the other parts of the coupler 106 when the second fastener 149 is secured (i.e., tightened) in the second coupler opening 110. In an alternate embodiment, the fastener guide 400 may include channels and the coupler holder 400 may include protrusions that are configured to mate with the channels so as function as the anti-splay feature described above. The fastener guide 500 is configured to correctly position the spine stabilization member 104 in the second coupler opening 110 without the need of additional instruments or tools. Specifically, the fastener guide 500 can be advanced through coupler holder 400 and toward the second coupler opening 110 until the spine stabilization member 104 contacts a least a portion of the bottom surface portion 162 and is substantially aligned along the longitudinal direction 142 (FIG. 2E). Hence, the fastener guide 500 can be configured to urge the spine stabilization rod 105 toward the second coupler opening 110. In particular, the fastener guide 500 can be configured to urge the spine stabilization rod 105 toward the coupler 106 such that the spine stabilization rod 105 is disposed in the second coupler opening 110 and is substantially aligned along the longitudinal direction 142.

Figure 5G:
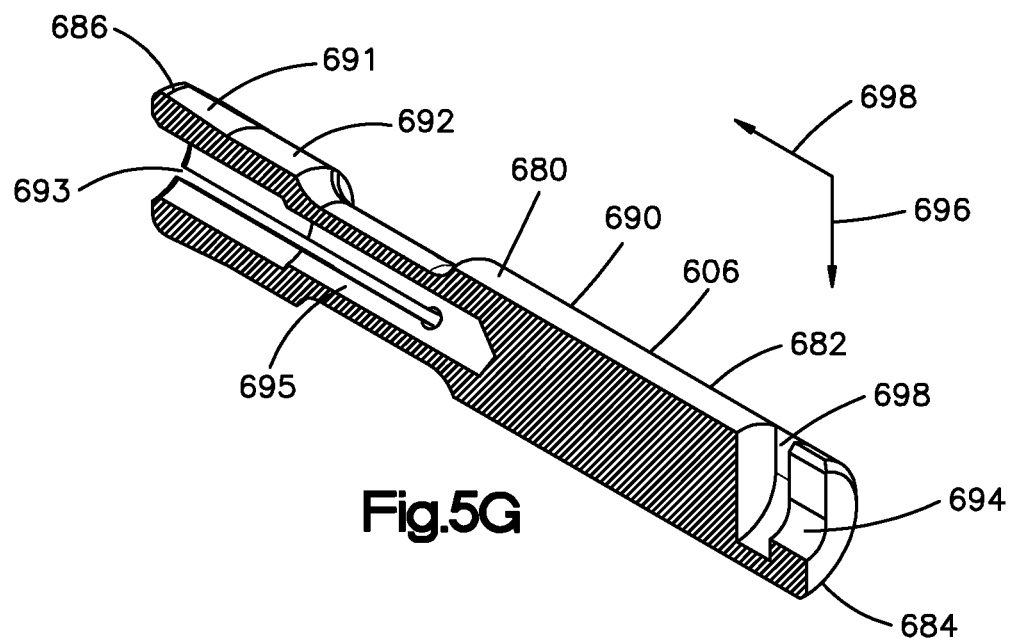
FIG. 5G is a sectional view of the fork shown in FIG. 5F, taken along section line 5G-5G.
Figure 5H:
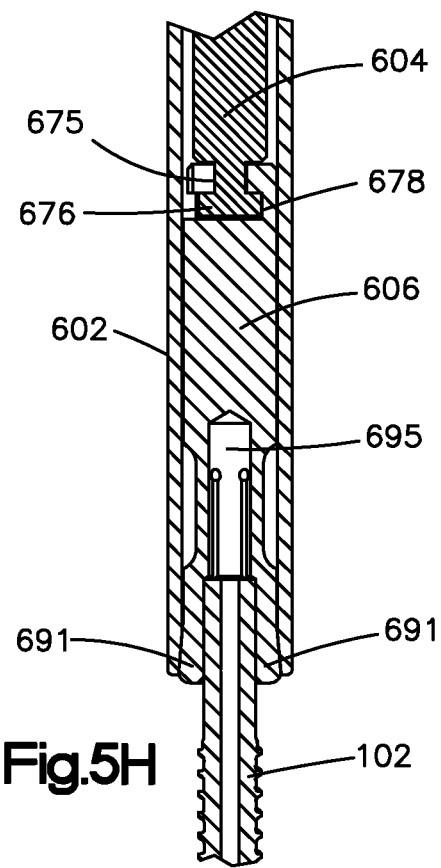
FIG. 5H is a cross-sectional view of the bone anchor removal tool shown in FIG. 5A, showing the bone anchor removal tool attached to a bone anchor, and the sleeve in a locked position.
Figure 5I:
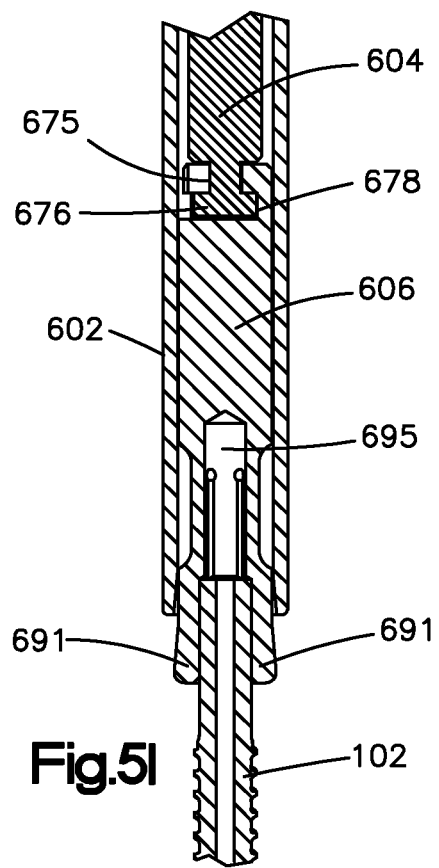
FIG. 5I is a cross-sectional view of the bone anchor removal tool shown in FIG. 5A, showing the bone anchor removal tool attached to a bone anchor, and the sleeve in an unlocked position.

With reference to FIGS. 5A-I, a bone anchor removal tool 600 is configured to remove bone anchor 102, such as the Schanz bone screw 103, from the vertebra V. The bone anchor removal tool can be partly or entirely constructed of instrument grade stainless steel but may also be constructed of titanium, aluminum, metallic alloys, polymeric materials, composite materials or nearly any relatively stiff, strong, biocompatible material. In the depicted embodiment, the bone anchor removal tool 600 may generally include a sleeve 602, a shaft 604 that is configured to be coupled to the sleeve 602, and a connector 606 configured that hold at least a portion of the bone anchor 102. The connector 606 can move relative to the sleeve 602 between an unlocked position (FIG. 5I) and a locked position (FIG. 5H). In the unlocked position, connector 606 can be positioned over at least a portion of the bone anchor 102. Then, the connector 606 can be moved from the unlocked position to the locked position to couple the bone anchor 102 to the bone anchor removal tool 600. Once the bone anchor 102 has been securely coupled to the bone anchor removal tool 600, the entire bone anchor removal tool 600 can be rotated about the rotation axis 628 to remove the bone anchor 102 from the vertebra. Alternatively or additionally, during removal of the bone anchor 102, a force can also be applied to the bone anchor removal tool 600 in a direction away from the vertebra to remove the bone anchor 102 from the vertebral.

The sleeve 602 includes a sleeve body 608 that is elongate along a longitudinal direction 610. The sleeve body 608 defines a first or proximal sleeve end 612 and a second or distal sleeve end 614 that is spaced from the first sleeve end 612 along the longitudinal direction 610. The sleeve 602 further defines a sleeve opening 616 that extends through sleeve body 608 between the first sleeve end 612 and the second sleeve end 614. The sleeve opening 616 can be elongate along the longitudinal direction 610 and is configured and sized to receive at least a portion of the shaft 604. In the depicted embodiment, the sleeve opening 616 may include a first opening portion 618 that is configured to receive a driver, a second opening portion 622 that is configured to receive at least a portion of the shaft 604, and a third or intermediate opening portion 624 disposed between the first opening portion 620 and the second opening portion 622. The first opening portion 620, the second opening portion 622, and the third opening portion 624 are spaced from one another along the longitudinal direction 610, and each is configured and sized to receive at least portion of the shaft 604.

The first opening portion 620 can define a socket 626, such as a hexagonal socket, that is configured to receive a conventional driver. At least a portion of the conventional driver can be disposed in the socket 626 so that the sleeve 602 can be rotated about a rotation axis 628. In the depicted embodiment, the first opening portion 620 defines a first cross-sectional dimension D1, such as a diameter, and the second opening portion 622 defines a second cross-sectional dimension D2, such as a diameter, that is smaller than the first cross-sectional dimension D1. In other words, the first cross-sectional dimension D1 may be larger than the second cross-sectional dimension D2. The third opening portion 624 defines a third cross-sectional dimension D3, such as a diameter, that is smaller than the first cross-sectional dimension D1 and the second cross-sectional dimension D2. The third opening portion 624 can be referred to as a threaded portion.

The sleeve body 608 defines an outer sleeve surface 630 and an opposed sleeve inner surface 632. The sleeve inner surface 632 defines the sleeve opening 616, and includes a shoulder 634 between the second opening portion 622 and the third opening portion 624. The shoulder 634 serves as a sleeve stop member 636 as discussed in detail below. In the depicted embodiment, the sleeve body 608 may further include inner sleeve threads 638 protruding from the sleeve inner surface 632. In particular, the inner sleeve threads 638 may be disposed around the third opening portion 624 of the sleeve opening 616.

The sleeve body 608 may further include first sleeve portion 648 and a second sleeve portion 650 that is spaced from the first sleeve portion 648 along the longitudinal direction 610. The first sleeve portion 648 may be located closer to the first sleeve end 612 than the second sleeve portion 650. The second sleeve portion 650 may be located closer to the second sleeve end 614 than the first sleeve portion 648. Further, the first sleeve portion 648 may define an external cross-sectional dimension, such as a diameter, than the external cross-sectional dimension, such as a diameter, of the second sleeve portion 650. In the depicted embodiment, the first sleeve portion 648 can be configured as a handle 652 that facilitates grabbing the sleeve 602 by a user. The handle 652 may include one or more grooves 654 that extend into the sleeve body 608. The grooves 654 can be elongate along the longitudinal direction 610, and can be spaced from one another around the sleeve body 608. In operation, the grooves 654 facilitate grabbing the handle 652 by a user.

With continuing reference to FIGS. 5A-I, the shaft 604 includes a shaft body 640 that is elongate along a longitudinal direction 642. The shaft body 640 defines a first or proximal shaft end 644 and a second or distal shaft end 646 that is spaced from the first shaft end 644 along the longitudinal direction 642. The first shaft end 644 may include one or more polygonal head, such as a hex head, that are configured to be coupled to a conventional driver, such as a socket screwdriver. In the depicted embodiment, the first shaft end 644 includes a first polygonal head 656 and a second polygonal head 658 that is spaced from the first polygonal head 656 along the longitudinal direction 642. Each of the first polygonal head 656 and the second polygonal head 658 are configured to receive a conventional driver, such as a socket screwdriver, to facilitate rotation of the shaft 604 about the rotation axis 628 (FIG. 5A).

At least a portion of the shaft body 640 defines a cross-sectional dimension D4, such as a diameter. The shaft 604 further includes a shaft stop member 660 that defines a cross-sectional dimension D5, such as a diameter, that is larger than the cross-sectional dimension D4. The shaft stop member 660 can be elongate along the longitudinal direction 642. Further, the shaft stop member 660 is configured to contact the sleeve stop member 636 so as to limit the advancement of the shaft 604 through the sleeve opening 616 in the longitudinal direction 610 (FIG. 5A). To this end, the cross-sectional dimension D5 can be larger than the cross-sectional dimension D2.

The shaft 604 further includes external shaft threads 662 that are configured to mate with the inner sleeve threads 638 such that rotation of the shaft 604 relative to the sleeve 602 about the rotation axis 628 in a first rotational direction 664 (e.g., counterclockwise) causes the shaft 604 to translate in a first longitudinal direction 666 and eventually tightens the external shaft threads 662 and the inner sleeve threads 638 together. Conversely, the rotation of the shaft 604 relative to the sleeve 602 about the rotation axis 628 in a second rotational direction 668 (opposite the first rotational direction 664) causes the shaft 604 to translate in a second longitudinal direction 670, loosening the external shaft threads 662 from the inner sleeve threads 638.

In an alternative embodiment, the external shaft threads 662 are configured to mate with the inner sleeve threads 638 such that rotation of the shaft 604 relative to the sleeve 602 about the rotation axis 628 in the second rotational direction 668 (that is opposite the first rotational direction 664) causes the shaft 604 to translate in the first longitudinal direction 666 and eventually tightens the external shaft threads 662 and the inner sleeve threads 638 together. In this alternative embodiment, the rotation of the shaft 604 relative to the sleeve 602 about the rotation axis 628 in the first rotational direction 664 causes the shaft 604 to translate in a second longitudinal direction 670, loosening the external shaft threads 662 from the inner sleeve threads 638.

With continuing reference to FIGS. 5A-I, the shaft 604 further includes a recess 672 that is configured to receive at least a portion of the connector 606 so as to couple the shaft 604 to the connector 606. The recess 672 can extend into the shaft body 640, and can be configured as annular recess 674. The recess 672 can be located at or adjacent the second shaft end 646. The shaft 604 further includes a coupler 676 that is configured to be coupled to a portion of the connector 606. The coupler 676 can be configured as a disk 678, and can be located at the second shaft end 646. Moreover, the coupler 676 can be spaced from the recess 672 along the longitudinal direction 642. A bar 675 can interconnect the coupler 676 and the rest of the shaft body 640. The bar 675 may have a substantially cylindrical configuration.

With continuing reference to FIGS. 5A-I, the connector 606 can be configured and sized to be received in the sleeve opening 616. Specifically, the connector 606 can be configured and sized to be received in the second opening portion 622 of the sleeve opening 616, and can be configured as a fork 682. In the depicted embodiment, the connector 606 includes a connector body 680 that defines a first connector end 684 and a second connector end 686. The first connector end 684 can be spaced from the second connector end 686 along a longitudinal direction 688. The connector body 680 includes a first connector portion 690 that is configured to be coupled to the shaft 604, and a second connector portion 692 that is configured to be coupled to the bone anchor 102. The first connector portion 690 may be spaced from the second connector portion 692 along the longitudinal direction 642.

The connector 606 further includes a first connector opening 694 that is configured and sized to receive the at least a portion of the shaft 604 so as to couple the shaft 604 to the connector 606. In the depicted embodiment, the first connector opening 694 can be configured as a slot, and is configured and sized to receive the bar 675 so as to couple the connector 606 to the shaft 604. The first connector opening 694 can extend into the connector body 680 in a transverse direction 696 that is substantially perpendicular to the longitudinal direction 688.

The connector 606 further defines a second connector opening 698 that is configured and sized to receive a portion of the shaft 604 so as to couple the shaft 604 to the connector 606. In the depicted embodiment, the second connector opening 698 is in communication with the first connector opening 694, and is configured and sized to receive the coupler 676, which can be configured as the disk 678, in order to couple the shaft 604 to the connector 606. Further, the second connector opening 698 can extend into the connector body 680 in the transverse direction 696, and can be configured as a slot. Each of the first connector opening 694 and the second connector opening 698 are disposed in the first connector portion 690.

The second connector portion 692 includes a plurality of connector prongs 691 that protrude from the first connector portion 690. The connector prongs 691 are spaced from one another around a perimeter of the second connector portion 692. The second connector portion 692 defines a plurality of slots 693 that separate the connector prongs 691 from one another. The slots 693 can be elongate along the longitudinal direction 688, and allow connector prongs 691 to flex toward or away from one another. The second connector portion 692 further defines a third connector opening 695 that is surrounded by the connector prongs 691. At least a portion of the third connector opening 695 extends along the second connector portion 692, and allows the connector prongs 691 to flex toward or away from one another. At least a portion of the third connector opening 695 can extend into the first connector portion 690. The third connector opening 695 can be configured and sized to receive at least a portion of the bone anchor 102. The connector prongs 691 can also be referred to as connector resilient members.

In operation, at least a portion of the bone anchor 102 should be positioned in the third connector opening 695 before using the bone anchor removal tool 600 to remove the bone anchor 102 from a vertebra. To couple the bone anchor 102 to the bone anchor removal tool 600, the connector 606 can be moved from the unlocked position to the locked position while at least a portion of the bone anchor 102 is disposed in the third connector opening 695. As discussed above, the rotation of the shaft 604 relative to the sleeve 602 about the rotation axis 628 causes the connector 606 to move between the unlocked position (FIG. 5I) and the locked position (FIG. 5H). In the unlocked position, at least a portion of connector prongs 691 are disposed outside of the sleeve 602. To move the connector 606 from the unlocked position to the locked position, the shaft 604 is rotated about rotation axis 628 while maintaining the sleeve 602 rotationally stationary. For example, a user can rotate the shaft 604 about the rotation axis 628 (manually or with a driver) while holding the sleeve 602 to prevent the sleeve 602 from rotating with the shaft 604 as the shaft 604 is rotated. While the shaft 604 is rotated relative to the sleeve 602, the external shaft threads 662 mate with the inner sleeve threads 638. Continued rotation of the shaft 604 eventually causes the external shaft threads 662 and the inner sleeve threads 638 to be tightened together, rotatably coupling the sleeve 602 to the shaft 604. When the sleeve 602 is rotatably coupled 604 to the shaft 604, the rotation of the shaft 604 causes concomitant rotation of the sleeve 602. Continued rotation of the shaft 604 relative to the sleeve 602 also causes the connector 606 to move from the unlocked position to the locked position.

In the locked position, the connector prongs 691 are substantially disposed inside the sleeve 602, and the connector prongs 691 are pressed against the bone anchor 102. Thus, when the connector 606 is in the locked position, the connector prongs 691 are closer to each other than in the unlocked position, and therefore apply an inward force to the bone anchor 102 in the direction indicated by arrows I such that at least a portion of the connector 606, such as the second connector portion 692, tightens around the portion of the bone anchor 102 surrounded by the connector prongs 691. Hence, in the locked position, the connector 606 couples the bone anchor 102 to the bone anchor removal tool 600.

Once the bone anchor 102 is coupled to the bone anchor removal tool 600, the user can rotate the sleeve 602 or the shaft 604 to unscrew the bone anchor 102 from a vertebra if the bone anchor 102 is a bone screw. As discussed above, when the connector 606 is in the locked position, the sleeve 602 can be rotatably coupled to the shaft 604 such that rotation of the sleeve 602 causes concomitant rotation of the shaft 604. Moreover, the rotation of the shaft 604 can cause rotation of the connector 606 to facilitate unscrewing the bone anchor 102. Alternatively or additionally, a force can be applied to the sleeve 602, the shaft 604, or both in a direction away from the vertebra to remove the bone anchor 102 from the vertebra once the bone anchor removal tool 600 is coupled to the bone anchor 102 in order to remove the bone anchor 102 from the vertebra.

Figure 6A:
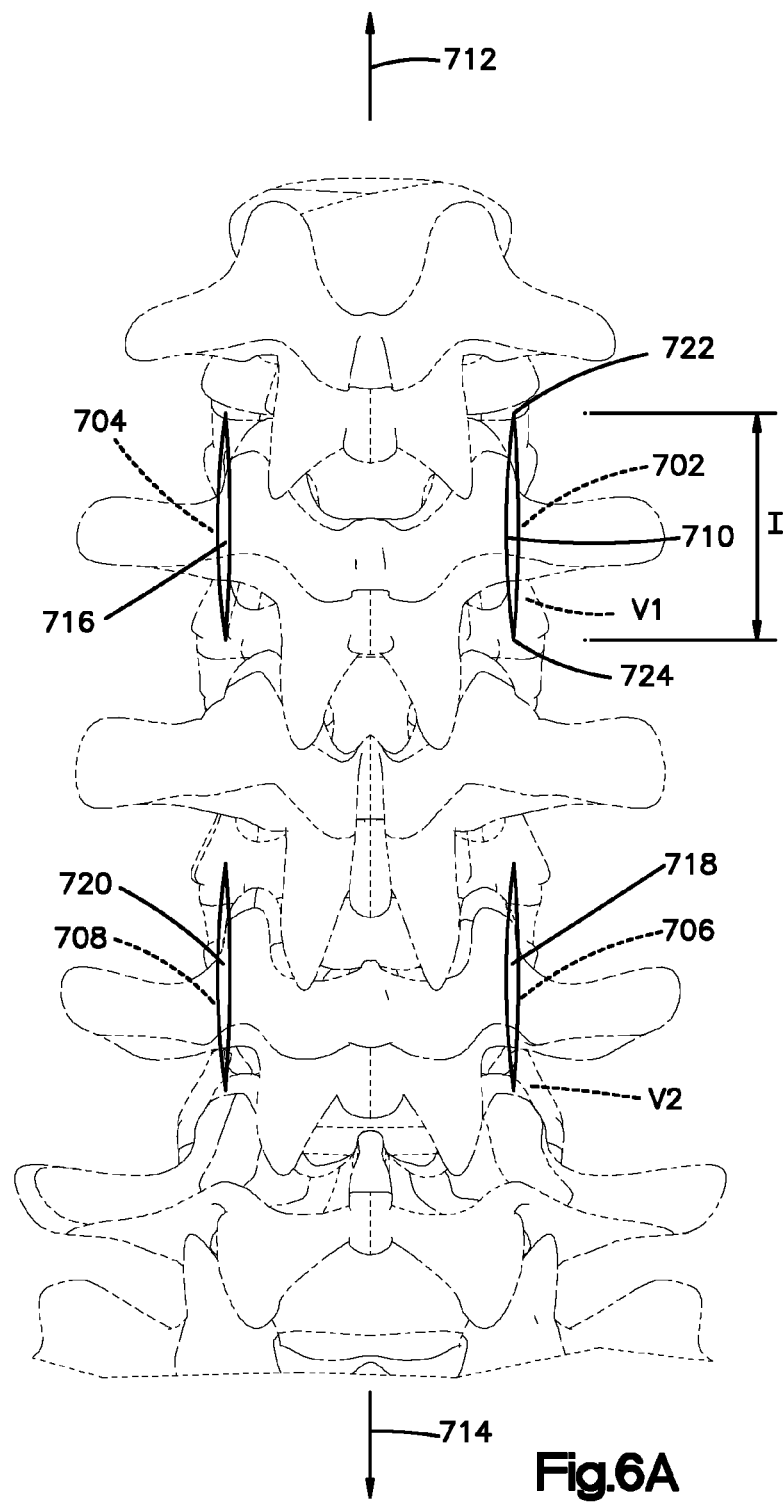
FIG. 6A is a rear view of a spine, showing first and second vertebrae, and incisions sites over the pedicles of the first and second vertebrae.

With reference to FIG. 6A, one or more components of the minimally invasive spinal stabilization system 100 can be used to adjust the spatial relationship between the first vertebra V1 and the second vertebra V2. The method may include one or more of the following steps. For example, the bone screw is attached to the first vertebra. The bone anchor coupler assembly can be coupled to the bone screw such that at least a portion of the bone screw is disposed in the first coupler opening of the bone anchor coupler assembly. A portion of the spine stabilization rod can be positioned in the second in the second coupler opening by advancing the portion of the spine stabilization rod through the top open end. The bone screw is moved relative to the spine stabilization rod to adjust the spatial relation between the first vertebra relative to the second vertebra. The bone screw can be translated or angulated relative to the spine stabilization rod.

The method may further include attaching a second bone screw to the second vertebra. Additionally, the method may include coupling a second bone anchor coupler assembly to the second bone screw. Moreover, a first rod portion of the spine stabilization rod can be coupled to a first bone anchor coupler assembly, and a second rod portion of the spine stabilization rod can be coupled to the second bone anchor coupler assembly. The method may further include attaching a first bone screw to a first pedicle of the first vertebra, and attaching a second bone screw to a second pedicle of the second vertebra.

The method may include locating the first and second vertebrae by, for example, obtaining a radiographic image of the first and second vertebrae. Additionally, a first incision can be made in a patient's skin over the first pedicle, and a second incision can be made in the patient's skin over the second vertebra. The first incision or the second incision can be made by advancing a scalpel into the patient's skin.

For example, the method may include locating a first pedicle 702 and a second pedicle 704 of the first vertebra V1. Additionally, a first pedicle 706 and a second pedicle 708 of the second vertebra V2 can be located. However, it is envisioned that the user may only located one pedicle in each vertebrae. To locate the pedicles of the first vertebra V1 and the second vertebrae V2, a patient may be positioned on a radiolucent operating table in the prone position. Then, a radiographic image of the first vertebra V1, the second vertebra V2, or both, may be obtained using a radiographic imaging apparatus such as an X-ray machine. The first pedicle 702, the second pedicle 704, the third pedicle 706, and the fourth pedicle 708 may be located to identify the incision sites. One or more incisions are made in the patient's skin over one or more of the pedicles 702, 704, 706, and 708. For example, a first percutaneous incision 710 may be made on the patient's skin over the first pedicle 702. A second percutaneous incision 716 may be made in the patient's skin over the second pedicle 704. A third percutaneous incision 718 may be made in the patient's skin over the third pedicle 706. A fourth incision 720 may be made in the patient's skin over the fourth pedicle 708. It is envisioned that fewer or more than four incision may be made one patient's skin. Each of the incisions may be substantially similar or identical. For example, the first percutaneous incision 710 (or any other incision) may be elongate along a cranial direction 712 or a caudal direction 714. In particular, the first percutaneous incision 710 may define a first incision end 722 and a second incision end 724 that is spaced from the first incision end 722 in the cranial direction. The first percutaneous incision 710 (or any other incision) may define an incision length I that extends from the first incision end 722 to the second incision end 724. The incision length I may range between about 20 millimeters and about 25 millimeters. Any of the incisions described herein may define the incision length I as described above. In addition, any of the incisions described above may be made by advancing a scalpel into the patient's skin. Next, for each incision, a subcutaneous tissue portion located the incision and the corresponding pedicle may be bluntly dissected. For instance, the method may include bluntly dissecting a first subcutaneous tissue portion that extends between the first percutaneous incision 710 and the first pedicle 702, and bluntly dissecting a second subcutaneous tissue portion that extends between the third incision 708 and the third pedicle 706. As used herein, percutaneous incisions do not include the large incisions that are necessary for open surgery. The percutaneous incisions described herein refer to the small incisions made during minimally invasive surgery. For example, percutaneous incisions may include an incision length that ranges between about 20 millimeters and about 25 millimeters as discussed above.

As described above, the method may further include bluntly dissecting a first subcutaneous tissue portion that is located between the first incision and the first pedicle, and bluntly dissecting a second subcutaneous tissue portion that is located between the second incision and the second pedicle. Additionally, a first cortex of the first pedicle can be perforated to create a first screw channel in the first pedicle. In particular, a trocar can be at least partially inserted in a cannulated awl so as to couple the trocar to the cannulated awl. At least a portion of the trocar and the cannulated awl can be inserted in a radiolucent sleeve. At least a portion of the trocar and the cannulated awl can be inserted into the first pedicle to create the first screw channel. A second cortex of the second pedicle can be perforated to create a second screw channel in the second pedicle. At least a portion of the first bone screw can be inserted in the first screw channel to attach the first bone screw to the first vertebra. At least a portion of the second bone screw can be inserted in the second screw channel before inserting at least a portion of the first bone screw in the first screw channel.

The method may further include inserting at least a portion of a first guidewire in the first screw channel before inserting at least a portion of the second bone screw in the second screw channel. At least one first dilator can be advanced over the first guidewire to dilate the first subcutaneous tissue portion. It is envisioned that multiple dilators of different cross-sectional dimension can be advanced over the first guidewire to dilate the first subcutaneous tissue portion. The method may further include advancing at least one second dilator over the second guidewire to dilate the second subcutaneous tissue portion. The first dilator or the second dilators can be eccentric dilators.

The method may further include advancing the first bone screw over the first guidewire to position at least a portion of the first bone screw in the first screw channel. The second bone screw can be advanced over the second guidewire to position at least a portion of the second bone screw in the second screw channel. The method may further include coupling the first bone screw to a screwdriver and advancing the first bone screw toward the first pedicle by turning the screwdriver. At least a portion of the first bone anchor coupler assembly can be advanced over the first bone screw such that at least a portion of the first bone screw is disposed in the first coupler opening of the first bone anchor coupler assembly. A first coupler holder can be coupled to the first bone anchor coupler assembly, and the first coupler holder can be advanced toward the first pedicle. The method may further coupling a second coupler holder to the second bone anchor coupler assembly, and advancing the second coupler holder toward the second pedicle. A distance between the first bone anchor coupler assembly and the second anchor coupler assembly can be measured to select the appropriate spine stabilization rod by, for example, placing a rod length indicator between the first coupler holder and the second coupler holder.

The method may further include holding the spine stabilization rod with a rod holder and advancing the rod holder toward the first and second pedicles such that the first rod portion is disposed in the second coupler opening of the first bone anchor coupler assembly. A locking cap can be placed in the second coupler opening of the first bone anchor coupler assembly to lock the first rod portion in the second coupler opening of the first bone anchor coupler assembly. The first locking cap can be held with a fastener guide. Then, the fastener guide can be advanced through the first coupler holder to position the locking cap in the second coupler opening of the first bone anchor coupler assembly. A persuader can be coupled to the coupler holder and the fastener guide. The persuader can be actuated to apply a force to the fastener guide such that the fastener guide advances through the first coupler holder. The persuader can be configured a scissor persuader, a forceps persuader or any other suitable persuader.

The method may further include advancing a screwdriver through the fastener guide to couple the screwdriver to the locking cap. The screwdriver is then turned to tighten the locking cap in the second coupler opening of the first bone anchor coupler assembly. The bone screw can be angulated relative to the spine stabilization rod by coupling a socket wrench to the bone screw and tilting the socket wrench relative to the spine stabilization rod. The socket wrench can be coupled to a nut at least partially disposed in the first coupler opening of the bone anchor coupler assembly. Then, the socket wrench can be turned to turn the nut so as to fix a position of the bone screw relative to the bone anchor coupler assembly. The bone screw can also be manually angulated relative to the spine stabilization rod.

The method may further include coupling forceps to the first and second bone screws, and actuating the forceps to the move the first and second cannulated bone screws toward each other. Also, the method may include coupling forceps to the first and second bone screws, and actuating the forceps to the move the first and second cannulated bone screws away from each other. The method may further include trimming the bone screw to shorten the screw length so that the bone screw does not extend pass the patient's skin. The bone screw can be trimmed by, for example, coupling a bolt cutter to the bone screw, and actuating the bolt cutter to trim the bone screw.

Figure 6B:
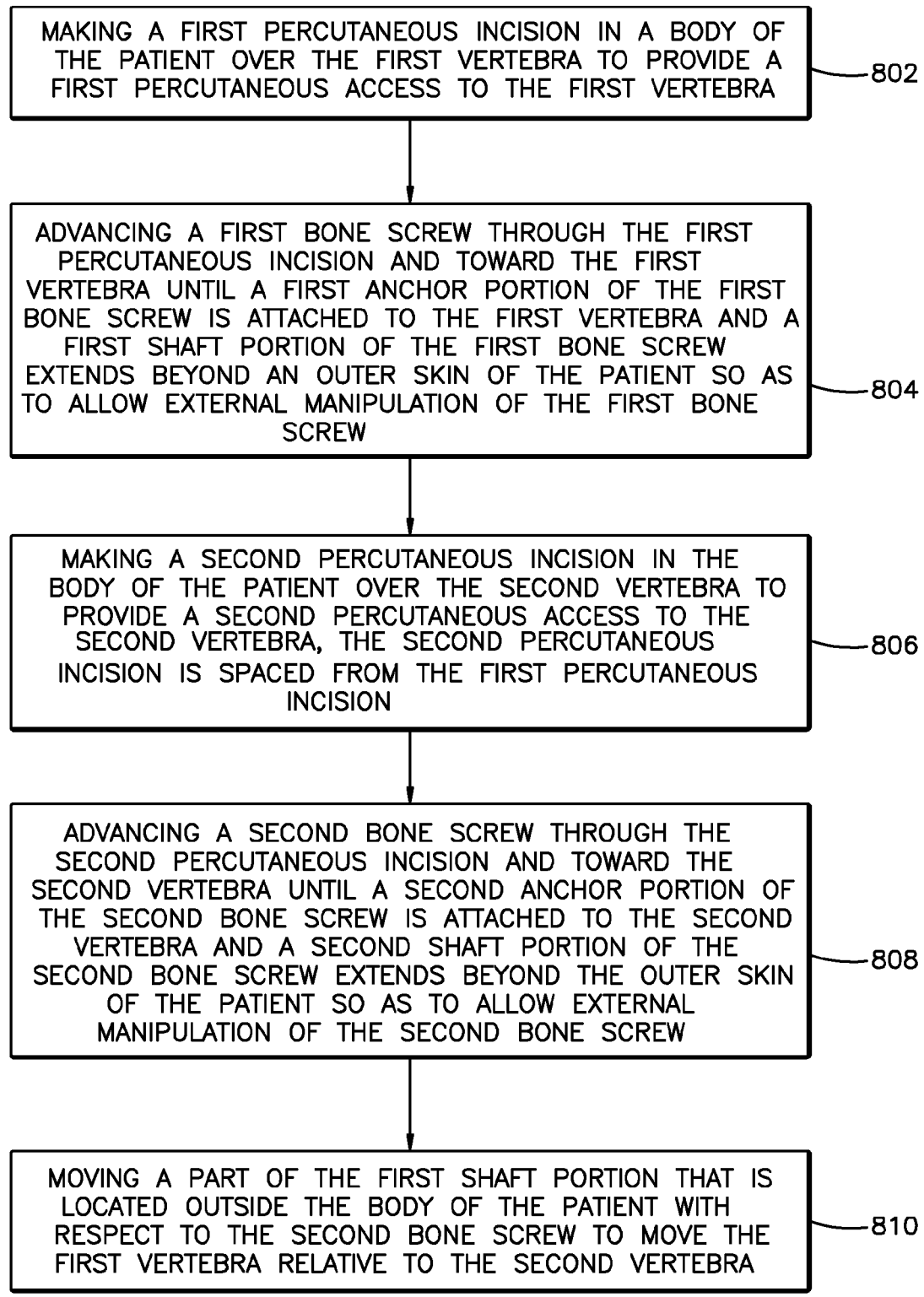
FIG. 6B is a flowchart illustrated a method of adjusting a spatial relation between the first vertebra and the second vertebra shown in FIG. 6A.

With reference to FIG. 6B, a minimally invasive method of adjusting a spatial relation between a first vertebra and a second vertebra of a patient may include one or more of the steps 802, 804, 806, 808, and 810. Step 802 includes making a first percutaneous incision in a body of the patient over the first vertebra to provide a first percutaneous access to the first vertebra. Step 804 includes advancing a first bone screw through the first percutaneous incision and toward the first vertebra until a first anchor portion of the first bone screw is attached to the first vertebra and a first shaft portion of the first bone screw extends beyond an outer skin of the patient so as to allow external manipulation of the first bone screw. Step 806 includes making a second percutaneous incision in the body of the patient over the second vertebra to provide a second percutaneous access to the second vertebra. The second percutaneous incision is spaced from the first percutaneous incision. For example, the second incision can be spaced from the first percutaneous incision along the cranial direction. Step 808 includes advancing a second bone screw through the second percutaneous incision and toward the second vertebra until a second anchor portion of the second bone screw is attached to the second vertebra and a second shaft portion of the second bone screw extends beyond the outer skin of the patient so as to allow external manipulation of the second bone screw. Step 810 includes moving a part of the first shaft portion that is located outside the body of the patient with respect to the second bone screw to move the first vertebra relative to the second vertebra.

The minimally invasive method may further include advancing a spine stabilization rod through the first percutaneous incision and toward the first vertebra; and coupling the spine stabilization rod between the first bone screw and the second bone screw. Additionally, the minimally invasive may include advancing a bone anchor coupler assembly through the first percutaneous incision and coupling the bone anchor coupler assembly to the first bone screw, the bone anchor coupler assembly configured to couple the spine stabilization rod to the first bone screw. The step of advancing the spine stabilization rod may include holding the spine stabilization rod with a rod holder, and advancing at least a portion of the rod holder through the first percutaneous incision and toward the first vertebra. The first percutaneous incision may define a first incision end, a second incision end that is spaced from the first incision end in a cranial direction, and an incision length that extends from the first incision end to the second incision end, and the incision length ranges between about 20 millimeters and about 25 millimeters. The minimally invasive method may further include advancing a guidewire through the first percutaneous incision and toward the first vertebra until a portion of the guidewire is coupled to the first vertebra. The minimally invasive method may further include advancing a dilator over the guidewire and toward the first vertebra to dilate subcutaneous tissue that is between the outer skin and the first vertebra. The step of advancing the first bone screw may include advancing the first bone screw over the guidewire. The minimally invasive method may further include measuring a distance from the first bone screw to the second bone screw, wherein the measuring step includes placing a rod length indicator between portions of the first and second bone screws that are located outside the body of the patient. The minimally invasive method may further include trimming the first bone screw so that the first bone screw does not extend pass the outer skin of the patient. The trimming step may include advancing at least a portion of a bolt cutter through the first percutaneous incision, coupling the bolt cutter to the first bone screw, and actuating the bolt cutter to trim the first bone screw.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A minimally invasive spinal stabilization system configured to move a first vertebra relative to a second vertebra between an initial position and an adjusted position, the minimally invasive spinal stabilization system comprising:
   a bone screw elongate along a screw axis, the bone screw defining a proximal end and a distal end spaced from the proximal end along the screw axis, the distal end configured to be attached to the first vertebra such that the proximal end is positioned outside of an incision to enable manipulation of at least a portion of a spine;
   a coupler that is configured to couple the bone screw to a spine stabilization rod, the coupler including a coupler body that defines a first coupler opening and a second coupler opening that is spaced from the first coupler opening, the first coupler opening configured to receive a portion of the bone screw, the second coupler opening configured to receive a portion of the spine stabilization rod, the coupler is configured to be coupled to the bone screw such that the bone screw is configured to move relative to the spine stabilization rod to move the first vertebra relative to the second vertebra between the initial position and the adjusted position when the distal end of the bone screw is attached to the first vertebra; and
   a coupler holder configured to attach to the coupler so as to position the coupler on the bone screw such that the bone screw is received in the first coupler opening, wherein when the coupler holder is attached to the coupler and the bone screw is received in the first coupler opening, the coupler holder is offset with respect to the screw axis along a direction that is perpendicular to the screw axis, the coupler holder including a hollow body that is elongate along a longitudinal holder axis; and
   a fastener guide configured to be disposed in the hollow body of the coupler holder such that the fastener guide is moveable along the longitudinal holder axis with respect to the coupler holder, the fastener guide having an elongated body that includes at least one ratchet tooth
   wherein the coupler holder further includes a ratchet member supported by the hollow body, the ratchet member includes at least one ratchet tooth, and an internal bore that receives the fastener guide when the fastener guide is inserted into the hollow body of the coupler holder, wherein the ratchet member is configured to move with respect to the hollow body of the coupler holder between a locked position where the at least one ratchet tooth of the ratchet member is engaged with the at least one ratchet tooth of the fastener guide, and an unlocked position where the at least one ratchet tooth of the ratchet member is disengaged from the at least one ratchet tooth of the fastener guide to permit movement of the fastener guide relative to the coupler holder.

2. The minimally invasive spinal stabilization system according to claim 1, wherein the coupler is configured to be coupled to the bone screw such that the bone screw is configured to angularly move relative to the received spine stabilization rod to angularly move the first vertebra relative to the second vertebra.

3. The minimally invasive spinal stabilization system according to claim 1, wherein the coupler is configured to be coupled to the to the bone screw such that the bone screw is configured to translate relative to the received spine stabilization rod to translate the first vertebra relative to the second vertebra between the initial position and the adjusted position.

4. The minimally invasive spinal stabilization system according to claim 3, wherein the first vertebra is closer to the second vertebra in the adjusted position than in the initial position.

5. The minimally invasive spinal stabilization system according to claim 4, wherein the first vertebra is farther from the second vertebra in the adjusted position than in the initial position.

6. The minimally invasive spinal stabilization system according to claim 1, wherein the fastener guide is configured to urge the spine stabilization rod toward the second coupler opening.

7. The minimally invasive spinal stabilization system according to claim 6, wherein the second coupler opening defines a front open end and a rear open end that is spaced from the front open end along a longitudinal direction, and the fastener guide is configured to urge the spine stabilization rod toward the coupler such that the spine stabilization rod is disposed in the second coupler opening and is substantially aligned along the longitudinal direction.

8. The minimally invasive spinal stabilization system according to claim 1, further comprising a bone anchor removal tool that includes a fork that is configured to receive at least a portion of the bone screw, and a sleeve at least partially surrounding the fork, wherein rotation of the fork relative to the sleeve causes the sleeve to translate relative to the fork and apply an inward force to the fork such that the fork tightens about the bone screw.

9. The minimally invasive spinal stabilization system according to claim 1, wherein the bone screw defines a screw length that extends from the proximal end to the distal end along the screw axis, wherein the coupler is configured to be coupled to the bone screw such that the coupler can be coupled at more than one position along the screw length of the bone screw.

10. The bone anchor coupler assembly according to claim 9, wherein the screw length is greater than about 30 mm.

11. The bone anchor coupler assembly according to claim 9, wherein the screw length is between about 30 mm and about 260 mm.

12. The minimally invasive spinal stabilization system according to claim 1, wherein the bone screw is configured to be attached to the first vertebra such that when the bone screw is attached to first vertebra and coupled to the coupler, movement of the bone screw causes the first vertebra to move relative to the second vertebra to correct spondylolisthesis.

13. The minimally invasive spinal stabilization system according to claim 1, wherein the longitudinal holder axis is offset with respect to the screw axis along the direction when the coupler holder is attached to the coupler and the bone screw is received by the first coupler opening.

14. The minimally invasive spinal stabilization system according to claim 1, wherein the coupler body defines a top body surface and a lower body surface that is spaced from the top body surface along a transverse direction, and the first coupler opening is elongate along the transverse direction, and the first coupler opening is spaced from the second coupler opening along a lateral direction that is perpendicular to the transverse direction.

15. The minimally invasive spinal stabilization system according to claim 14, further comprising an angular adjustment member movably coupled to the coupler body such that the bone screw is configured to move relative to the coupler body when 1) the portion of the bone screw is received in the first coupler opening to adjust a position of the first vertebra relative to the second vertebra, and 2) the bone screw is attached to the first vertebra.

16. The minimally invasive spinal stabilization system according to claim 15, wherein the angular adjustment member is a pivot member that is pivotally coupled to the coupler body such that the bone screw is configured to pivot relative to the coupler body when 1) the portion of the bone is received in the first coupler opening to adjust an angular position of the first vertebra relative to the second vertebra, and 2) the bone screw is attached to the first vertebra.

17. The minimally invasive spinal stabilization system according to claim 16, wherein the collet is configured to be coupled to the pivot member such that pivotal movement of the pivot member relative to the coupler body causes a corresponding pivotal movement of the collet relative to the coupler body.

18. The minimally invasive spinal stabilization system according to claim 16, wherein the coupler body defines a top body surface and a lower body surface spaced from the top body surface along the transverse direction, the top body surface having a substantially arc-shape, and the pivot member defines a lower pivot surface that defines a substantially concave shape that substantially corresponds to the substantially arc shape of the top body surface such that the pivot member is configured to move along the top body surface.

19. The minimally invasive spinal stabilization system according to claim 18, further comprising coupler teeth that protrude from the coupler body, the coupler teeth disposed along the top body surface, and the pivot member includes a pivot body and pivot teeth that protrude from pivot body, and the pivot teeth configured to mate with the coupler teeth such that the pivot member is configured to incrementally pivot relative to the coupler body.

20. The minimally invasive spinal stabilization system according to claim 14, wherein the first coupler opening defines a cross-sectional dimension that decreases in the transverse direction.

21. The minimally invasive spinal stabilization system according to claim 1, wherein the coupler holder includes a resilient member, the resilient member being configured to engage the coupler body.

22. The minimally invasive spinal stabilization system according to claim 21, wherein the coupler body defines an outer surface and a recess that extends into the outer surface, wherein the recess is configured and sized to receive a portion of the resilient member.

23. The minimally invasive spinal stabilization system according to claim 21, wherein the coupler body defines a first wall and an opposed second wall, the first and second walls at least partially defining the second coupler opening therebetween, wherein the first coupler opening is spaced from the second wall in a direction away from the first wall.

24. The minimally invasive spinal stabilization system according to claim 23, wherein, the distal end of the coupler holder defines a first distal portion and second opposed distal portion, the first distal portion including the resilient member, wherein the first wall of coupler body is configured to receive the resilient member, and the second wall of the coupler body is configured to engage the second distal portion.

25. The minimally invasive spinal stabilization system according to claim 24, wherein the second distal portion defines a first tine, a second tine spaced from the first tine, and a space between the first tine and the second tine, wherein the space is configured and sized to receive a complementary shaped portion of the second wall.

26. The minimally invasive spinal stabilization system according to claim 1, further comprising a collet at least partially disposed in the first coupler opening, the collet defining an upper end, an opposed lower end, the lower end of the collet configured to abut the coupler body, wherein the collet is configured to receive at least a portion of the bone screw.

27. The minimally invasive spinal stabilization system according to claim 1, wherein the body further comprises a fastener movably coupled to the collet such that rotation of the fastener about the collet causes the collet to move between an unlocked position in which the collet is configured to pivot relative to the coupler body, and a locked position in which the collet is fixed relative to the coupler body to fix a position of the bone screw relative to the coupler body.

28. The minimally invasive spinal stabilization system according to claim 27, wherein the collet includes a compressible portion, and the rotation of the fastener causes the collet to move between the unlocked position and the locked position in which the compressible portion is press-fitted in the first coupler opening.

29. The minimally invasive spinal stabilization system according to claim 1, further comprising a locking cap configured to be at least partially disposed in the second coupler opening to lock at least a portion of the spine stabilization rod in the second coupler opening.

30. The minimally invasive spinal stabilization system according to claim 1, wherein the ratchet body defines opposed first and second walls spaced apart with respect to each other along a transverse axis that is perpendicular to the longitudinal axis, and an internal surface spaced apart from the opposed walls, the internal surface defining the internal bore that extends through the ratchet body along the longitudinal axis, the internal surface include the at least one ratchet tooth.

31. A minimally invasive spinal stabilization system configured to move a first vertebra relative to a second vertebra between an initial position and an adjusted position, the minimally invasive spinal stabilization system comprising:

a bone screw elongate along a longitudinal screw axis, the bone screw defining a proximal end and a distal end spaced from the proximal end along the longitudinal screw axis, the distal end configured to be attached to the first vertebra such that the proximal end is positioned outside of an incision to enable manipulation of at least a portion of a spine;

a coupler that is configured to couple the bone screw to a spine stabilization rod, the coupler including a coupler body that defines a first coupler opening and a second coupler opening that is spaced from the first coupler opening, the first coupler opening configured to receive a portion of the bone screw, the second coupler opening configured to receive a portion of the spine stabilization rod, the coupler being configured to be coupled to the bone screw such that the bone screw is configured to move relative to the spine stabilization rod to move the first vertebra relative to the second vertebra between the initial position and the adjusted position when the distal end of the bone screw is attached to the first vertebra; and a coupler holder configured to attach to the coupler so as to position the coupler on the bone screw such that the bone screw is received in the first coupler opening, wherein when the coupler holder is attached to the coupler and the bone screw is received in the first coupler opening, the coupler holder is offset with respect to the longitudinal screw axis along a direction that is perpendicular to the screw axis, wherein the coupler holder includes a hollow body that is elongate along a longitudinal holder axis, the hollow body defining a proximal end, a distal end spaced from the proximal end along the longitudinal holder axis in a distal direction, the distal end including first and second prongs configured to engage the coupler, wherein the first and second prongs terminate at respective first and second prong ends, wherein the first prong end extends beyond the second prong end in the distal direction through a plane that 1) is perpendicular to the longitudinal holder axis, and 2) intersects a distal-most point on the second prong end.

32. The bone anchor coupler assembly according to claim 31, wherein the first holder prong comprises a resilient member configured to engage the coupler body.

33. The bone anchor coupler assembly according to claim 32, wherein the second holder prong comprises a first tine, a second tine spaced from the first tine to define a tine space between the first tine and the second tine, wherein the tine space is configured to receive a complementary shaped portion of the coupler body.

* * * * *